US 9,515,267 B2

(12) United States Patent
Park et al.

(10) Patent No.: US 9,515,267 B2
(45) Date of Patent: Dec. 6, 2016

(54) ELECTROACTIVE MATERIALS

(75) Inventors: Kyung-Ho Park, Wilmington, DE (US); Nora Sabina Radu, Landenberg, PA (US); Gary A Johansson, Hockessin, DE (US); Adam Fennimore, Wilmington, DE (US); William J Delaney, Bear, DE (US); Daniel David Lecloux, Midland, MI (US)

(73) Assignee: EI DU PONT DE NEMOURS AND COMPANY, Wilmington, DE (US)

( * ) Notice: Subject to any disclaimer, the term of this patent is extended or adjusted under 35 U.S.C. 154(b) by 297 days.

(21) Appl. No.: 13/703,997

(22) PCT Filed: Jun. 16, 2011

(86) PCT No.: PCT/US2011/040650
§ 371 (c)(1),
(2), (4) Date: Dec. 13, 2012

(87) PCT Pub. No.: WO2011/159872
PCT Pub. Date: Dec. 22, 2011

(65) Prior Publication Data
US 2013/0082251 A1    Apr. 4, 2013

Related U.S. Application Data

(60) Provisional application No. 61/355,614, filed on Jun. 17, 2010.

(51) Int. Cl.
*H01L 51/50* (2006.01)
*H01L 51/00* (2006.01)
(Continued)

(52) U.S. Cl.
CPC ......... *H01L 51/0061* (2013.01); *C07C 211/54* (2013.01); *C07C 211/56* (2013.01);
(Continued)

(58) Field of Classification Search
None
See application file for complete search history.

(56) References Cited

U.S. PATENT DOCUMENTS

2004/0135131 A1* 7/2004 Treacher ............. C07C 17/2632
                                                    252/582
2004/0170863 A1*  9/2004 Kim ........................ C07C 13/72
                                                    428/690
2004/0253389 A1* 12/2004 Suzuki et al. ................ 428/1.1

FOREIGN PATENT DOCUMENTS

EP        721935 A1    9/1994
EP       1095931 A1   10/1994
(Continued)

OTHER PUBLICATIONS

Aonuma et al., Material design of hole transport material capable of thich-film formation in organic light emitting diodes, 2007, Applied Physics Letters, vol. 90(18) pp. 183503-1 to 183503-3.*

(Continued)

*Primary Examiner* — Gregory Clark

(57) ABSTRACT

There is disclosed a compound having Formula I or Formula I':

$$R^6 \left[ \left( \underset{f}{\overset{(R^1)_a}{\bigcirc}} \right) \underset{Ar^1}{\overset{}{N}} \left( \underset{}{\overset{(R^2)_b}{\bigcirc}} \right) \left( \underset{g}{\overset{(R^3)_c}{\bigcirc}} \right) \left( \underset{}{\overset{(R^4)_d}{\bigcirc}} \right) \underset{Ar^2}{\overset{}{N}} \left( \underset{h}{\overset{(R^5)_e}{\bigcirc}} \right) \right]_n R^6$$
(I)

(Continued)

-continued

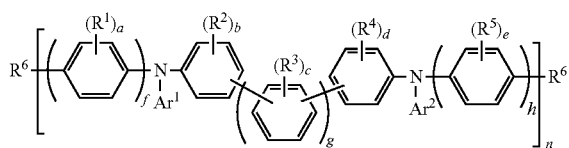

In Formula I and Formula I':
  $Ar^1$ and $Ar^2$ are the same or different and are aryl groups;
  $R^1$ through $R^5$ are independently the same or different at each occurrence and are D, F, alkyl groups, aryl groups, alkoxy groups, silyl groups, or crosslinkable groups;
  $R^6$ is H, D, or halogen;
  a through e are independently an integer from 0 to 4;
  f is 1 or 2;
  g is 0, 1 or 2;
  h is 1 or 2; and
  n is an integer greater than 0.

8 Claims, 1 Drawing Sheet

(51) Int. Cl.
| | | |
|---|---|---|
| C07C 211/54 | (2006.01) | |
| C07C 211/56 | (2006.01) | |
| C08G 73/02 | (2006.01) | |
| C08L 79/02 | (2006.01) | |
| C09K 11/06 | (2006.01) | |
| H05B 33/14 | (2006.01) | |

(52) U.S. Cl.
   CPC ............ *C08G 73/026* (2013.01); *C08L 79/02* (2013.01); *C09K 11/06* (2013.01); *H01L 51/0035* (2013.01); *H05B 33/14* (2013.01); *C09K 2211/1014* (2013.01); *C09K 2211/1433* (2013.01); *H01L 51/006* (2013.01); *H01L 51/0081* (2013.01); *H01L 51/5012* (2013.01)

(56) References Cited

FOREIGN PATENT DOCUMENTS

| EP | 666298 A2 | 2/1995 | |
|---|---|---|---|
| EP | 1136469 A1 | 9/2000 | |
| EP | 1864965 A1 | 12/2007 | |
| JP | 2009/152435 A | 7/2009 | |
| WO | 2009/067419 A1 | 5/2009 | |
| WO | WO 2009067419 | * 5/2009 | ............. H01L 51/00 |

OTHER PUBLICATIONS

International Search Report, PCT/US2011/040650 Filed Jun. 16, 2011.

* cited by examiner

ELECTROACTIVE MATERIALS

RELATED APPLICATION DATA

This application claims priority under 35 U.S.C. §119(e) from U.S. Provisional Application No. 61/355,614 filed on Jun. 17, 2010, which is incorporated by reference herein in its entirety.

BACKGROUND INFORMATION

1. Field of the Disclosure

The present disclosure relates to novel electroactive compounds. The disclosure further relates to electronic devices having at least one active layer comprising such an electroactive compound.

2. Description of the Related Art

In organic photoactive electronic devices, such as organic light emitting diodes ("OLED"), that make up OLED displays, the organic active layer is sandwiched between two electrical contact layers. In an OLED the organic photoactive layer emits light through the light-transmitting electrical contact layer upon application of a voltage across the electrical contact layers.

It is well known to use organic electroluminescent compounds as the photoactive component in light-emitting diodes. Simple organic molecules, conjugated polymers, and organometallic complexes have been used. Devices that use electroluminescent materials frequently include one or more added electroactive layers, which are positioned between the electroluminescent layer and a contact layer. A hole transport layer can be positioned between the electroluminescent layer and the hole-injecting contact layer. The hole-injecting contact layer may also be called the anode. An electron transport layer can be positioned between the electroluminescent layer and the electron-injecting contact layer. The electron-injecting contact layer may also be called the cathode.

There is a continuing need for electroactive materials for use in electronic devices.

SUMMARY

There is provided a compound having Formula I or Formula I':

wherein:

$Ar^1$ and $Ar^2$ are the same or different and are aryl groups;

$R^1$ through $R^5$ are independently the same or different at each occurrence and are selected from the group consisting of D, F, alkyl, aryl, alkoxy, silyl, and a crosslinkable group;

$R^6$ is the same or different at each occurrence and is selected from the group consisting of H, D, and halogen;

a through e are independently an integer from 0 to 4;

f is 1 or 2;

g is 0, 1 or 2;

h is 1 or 2; and n is an integer greater than 0.

There is also provided an electronic device having at least one layer comprising the above compound.

The foregoing general description and the following detailed description are exemplary and explanatory only and are not restrictive of the invention, as defined in the appended claims.

BRIEF DESCRIPTION OF THE DRAWINGS

Embodiments are illustrated in the accompanying figures to improve understanding of concepts as presented herein.

Figure 1:
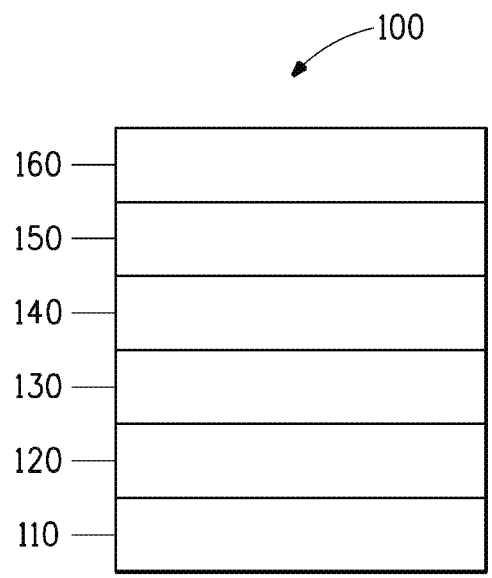
FIG. 1 includes an illustration of one example of an organic electronic device.

Skilled artisans appreciate that objects in the figures are illustrated for simplicity and clarity and have not necessarily been drawn to scale. For example, the dimensions of some of the objects in the figures may be exaggerated relative to other objects to help to improve understanding of embodiments.

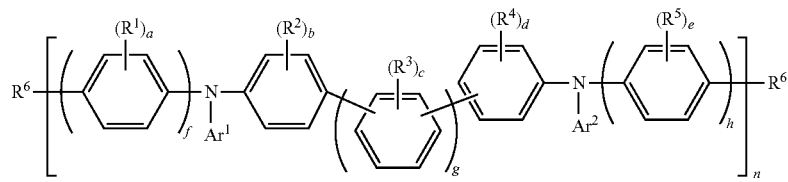

(I)

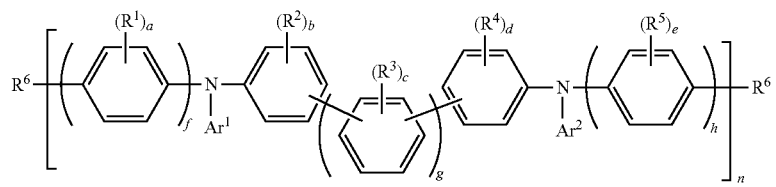

(I')

DETAILED DESCRIPTION

There is provided a compound having Formula I or Formula I':

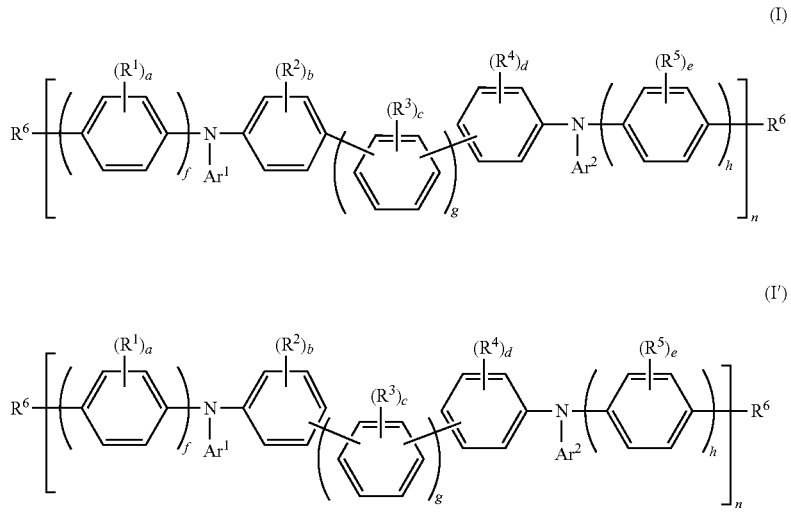

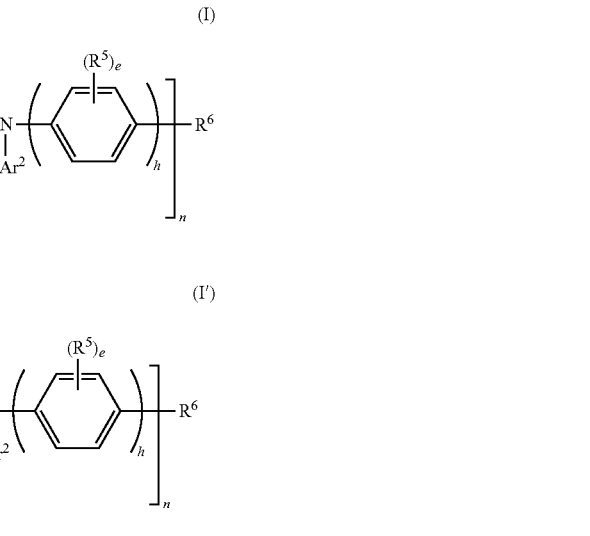

wherein:

$Ar^1$ and $Ar^2$ are the same or different and are aryl groups;

$R^1$ through $R^5$ are independently the same or different at each occurrence and are selected from the group consisting of D, F, alkyl, aryl, alkoxy, silyl, and a cross-linkable group;

$R^6$ is the same or different at each occurrence and is selected from the group consisting of H, D, and halogen;

a through e are independently an integer from 0 to 4;

f is 1 or 2;

g is 0, 1 or 2;

h is 1 or 2; and n is an integer greater than 0.

There is also provided an electronic device having at least one layer comprising the above compound.

Many aspects and embodiments have been described above and are merely exemplary and not limiting. After reading this specification, skilled artisans appreciate that other aspects and embodiments are possible without departing from the scope of the invention.

Other features and benefits of any one or more of the embodiments will be apparent from the following detailed description, and from the claims. The detailed description first addresses Definitions and Clarification of Terms followed by the Electroactive Compound, the Electronic Device, and finally Examples.

1. Definitions and Clarification of Terms

Before addressing details of embodiments described below, some terms are defined or clarified.

As used herein, the term "alkyl" includes branched and straight-chain saturated aliphatic hydrocarbon groups. Unless otherwise indicated, the term is also intended to include cyclic groups. Examples of alkyl groups include methyl, ethyl, propyl, isopropyl, butyl, isobutyl, secbutyl, tertbutyl, pentyl, isopentyl, neopentyl, cyclopentyl, hexyl, cyclohexyl, isohexyl and the like. The term "alkyl" further includes both substituted and unsubstituted hydrocarbon groups. In some embodiments, the alkyl group may be mono-, di- and tri-substituted. One example of a substituted alkyl group is trifluoromethyl. Other substituted alkyl groups are formed from one or more of the substituents described herein. In certain embodiments alkyl groups have 1 to 20 carbon atoms. In other embodiments, the group has 1 to 6 carbon atoms. The term is intended to include heteroalkyl groups. Heteroalkyl groups may have from 1-20 carbon atoms.

The term "aryl" means an aromatic carbocyclic moiety, which may be a single ring (monocyclic) or multiple rings (bicyclic, or more) fused together or linked covalently. Any suitable ring position of the aryl moiety may be covalently linked to the defined chemical structure. Examples of aryl moieties include, but are not limited to, phenyl, 1-naphthyl, 2-naphthyl, dihydronaphthyl, tetrahydronaphthyl, biphenyl. anthryl, phenanthryl, fluorenyl, indanyl, biphenylenyl, acenaphthenyl, acenaphthylenyl, and the like. In some embodiments, aryl groups have 6 to 60 carbon atoms; in some embodiments, 6 to 30 carbon atoms. The term is intended to include heteroaryl groups. Heteroaryl groups may have from 4-50 carbon atoms; in some embodiments, 4-30 carbon atoms.

The term "alkoxy" is intended to mean the group —OR, where R is alkyl.

The term "aryloxy" is intended to mean the group —OR, where R is aryl.

Unless otherwise indicated, all groups can be substituted or unsubstituted.

The term "charge transport," when referring to a layer, material, member, or structure is intended to mean such layer, material, member, or structure facilitates migration of such charge through the thickness of such layer, material, member, or structure with relative efficiency and small loss of charge. Hole transport materials facilitate positive charge; electron transport materials facilitate negative charge. Although light-emitting materials may also have some charge transport properties, the term "charge transport layer, material, member, or structure" is not intended to include a layer, material, member, or structure whose primary function is light emission.

The term "compound" is intended to mean an electrically uncharged substance made up of molecules that further include atoms, wherein the atoms cannot be separated from their corresponding molecules by physical means without breaking chemical bonds. The term is intended to include oligomers and polymers.

The term "crosslinkable group" or "crosslinking group" is intended to mean a group than can lead to crosslinking via thermal treatment or exposure to radiation. In some embodiments, the radiation is UV or visible.

The term "electroactive" as it refers to a layer or a material, is intended to indicate a layer or material which electronically facilitates the operation of the device. Examples of active materials include, but are not limited to, materials which conduct, inject, transport, or block a charge, where the charge can be either an electron or a hole, or materials which emit radiation or exhibit a change in concentration of electron-hole pairs when receiving radiation. Examples of inactive materials include, but are not limited to, planarization materials, insulating materials, and environmental barrier materials.

The prefix "fluoro" is intended to indicate that one or more hydrogens in a group has been replaced with fluorine.

The prefix "hetero" indicates that one or more carbon atoms has been replaced with a different atom. In some embodiments, the heteroatom is O, N, S, or combinations thereof.

The term "liquid composition" is intended to mean a liquid medium in which a material is dissolved to form a solution, a liquid medium in which a material is dispersed to form a dispersion, or a liquid medium in which a material is suspended to form a suspension or an emulsion.

The term "silyl" refers to the group $R_3Si-$, where R is H, C1-20 alkyl, fluoroalkyl, or aryl. In some embodiments, one or more carbons in an R alkyl group are replaced with Si. In some embodiments, the silyl groups are $(hexyl)_2Si(Me)CH_2CH_2Si(Me)_2-$ and $[CF_3(CF_2)CH_2CH_2]_2SiMe-$.

The term "siloxane" refers to the group $(RO)_3Si-$, where R is H, D, C1-20 alkyl, or fluoroalkyl.

The phrase "adjacent to," when used to refer to layers in a device, does not necessarily mean that one layer is immediately next to another layer. On the other hand, the phrase "adjacent R groups," is used to refer to R groups that are next to each other in a chemical formula (i.e., R groups that are on atoms joined by a bond).

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

In this specification, unless explicitly stated otherwise or indicated to the contrary by the context of usage, where an embodiment of the subject matter hereof is stated or described as comprising, including, containing, having, being composed of or being constituted by or of certain features or elements, one or more features or elements in addition to those explicitly stated or described may be present in the embodiment. An alternative embodiment of the disclosed subject matter hereof, is described as consisting essentially of certain features or elements, in which embodiment features or elements that would materially alter the principle of operation or the distinguishing characteristics of the embodiment are not present therein. A further alternative embodiment of the described subject matter hereof is described as consisting of certain features or elements, in which embodiment, or in insubstantial variations thereof, only the features or elements specifically stated or described are present.

Group numbers corresponding to columns within the Periodic Table of the elements use the "New Notation" convention as seen in the *CRC Handbook of Chemistry and Physics*, 81$^{st}$ Edition (2000-2001).

Unless otherwise defined, all technical and scientific terms used herein have the same meaning as commonly understood by one of ordinary skill in the art to which this invention belongs. Although methods and materials similar or equivalent to those described herein can be used in the practice or testing of embodiments of the present invention, suitable methods and materials are described below. All publications, patent applications, patents, and other references mentioned herein are incorporated by reference in their entirety, unless a particular passage is cited. In case of conflict, the present specification, including definitions, will control. In addition, the materials, methods, and examples are illustrative only and not intended to be limiting.

To the extent not described herein, many details regarding specific materials, processing acts, and circuits are conventional and may be found in textbooks and other sources within the organic light-emitting diode display, photodetector, photovoltaic, and semiconductive member arts.

2. Electroactive Compound

The compound described herein has Formula I or Formula I':

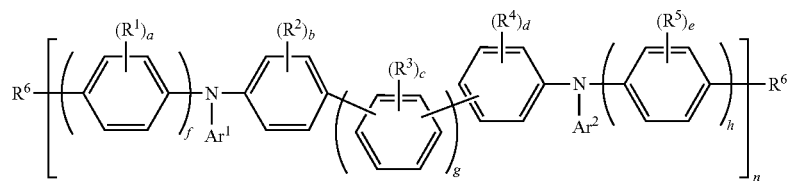

(I)

-continued

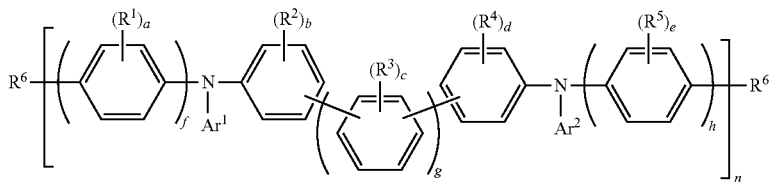
(I')

wherein:

Ar$^1$ and Ar$^2$ are the same or different and are aryl groups;

R$^1$ through R$^5$ are independently the same or different at each occurrence and are selected from the group consisting of D, F, alkyl, aryl, alkoxy, silyl, and a cross-linkable group;

R$^6$ is the same or different at each occurrence and is selected from the group consisting of H, D, and halogen;

a through e are independently an integer from 0 to 4;

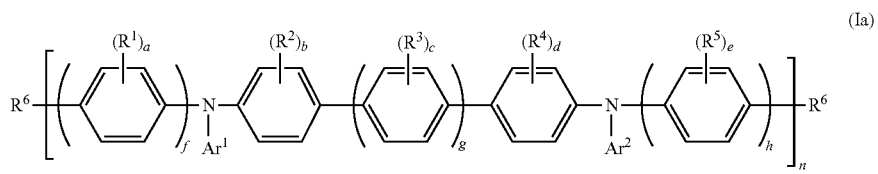
(Ia)

f is 1 or 2;

g is 0, 1 or 2;

h is 1 or 2; and n is an integer greater than 0.

The compound can be a small molecule with n=1, an oligomer, or a polymer. In some embodiments, the compound is a polymer with M$_n$>20,000; in some embodiments, M$_n$>50,000.

In some embodiments, n=1 and R$^6$ is halogen. Such compounds can be useful as monomers for the formation of polymeric compounds. In some embodiments, the halogen is Cl or Br; in some embodiments, Br.

In some embodiments, n=1 and R$^6$ is H or D.

In some embodiments, the compound having Formula I or Formula I' is deuterated. The term "deuterated" is intended to mean that at least one H has been replaced by D. The term "deuterated analog" refers to a structural analog of a compound or group in which one or more available hydrogens have been replaced with deuterium. In a deuterated compound or deuterated analog, the deuterium is present in at least 100 times the natural abundance level. In some embodiments, the compound is at least 10% deuterated. By "% deuterated" or "% deuteration" is meant the ratio of deuterons to the sum of protons plus deuterons, expressed as a percentage. In some embodiments, the compound is at least 20% deuterated; in some embodiments, at least 30% deuterated; in some embodiments, at least 40% deuterated; in some embodiments, at least 50% deuterated; in some embodiments, at least 60% deuterated; in some embodiments, at least 70% deuterated; in some embodiments, at least 80% deuterated; in some embodiments, at least 90% deuterated; in some embodiments, 100% deuterated.

Deuterated materials can be less susceptible to degradation by holes, electrons, exitons, or a combination thereof. Deuteration can potentially inhibit degradation of the compound during device operation, which in turn can lead to improved device lifetime. In general, this improvement is accomplished without sacrificing other device properties. Furthermore, the deuterated compounds frequently have greater air tolerance than the non-deuterated analogs. This can result in greater processing tolerance both for the preparation and purification of the materials and in the formation of electronic devices using the materials.

In some embodiments, the compound of Formula I or Formula I' has Formula Ia:

where R$^1$ through R$^6$, Ar$^1$, Ar$^2$, a-h, and n are as defined above for Formula I.

In some embodiments, Ar$^1$ and Ar$^2$ are aryl groups having no fused rings. In some embodiments, Ar$^1$ and Ar$^2$ have Formula a

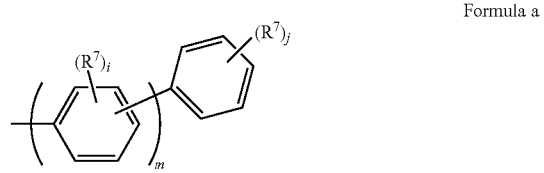
Formula a where:

R$^7$ is the same or different at each occurrence and is selected from the group consisting of D, alkyl, alkoxy, siloxane and silyl;

i is the same or different at each occurrence and is an integer from 0-4;

j is an integer from 0-5; and m is an integer from 1 to 5.

In some embodiments, Ar$^1$ and Ar$^2$ have Formula b

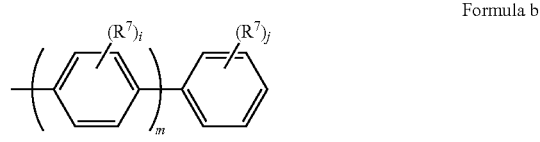
Formula b where:

R$^7$ is the same or different at each occurrence and is selected from the group consisting of D, alkyl, alkoxy, siloxane and silyl;

i is the same or different at each occurrence and is an integer from 0-4;

j is an integer from 0-5; and m is an integer from 1 to 5.

In some embodiments of Formulae a and b, at least one of i and j is not zero. In some embodiments, m=1-3.

In some embodiments, $Ar^1$ and $Ar^2$ are selected from the group consisting of phenyl, biphenyl, terphenyl, deuterated derivatives thereof, and derivatives thereof having one or more substituents selected from the group consisting of alkyl, alkoxy, silyl, and a substituent with a crosslinking group.

In some embodiments, $R^1$ through $R^5$ are D or $C_{1-10}$ alkyl. In some embodiments, the alkyl group is deuterated.

In some embodiments, a=e=0. In some embodiments a=e=4 and $R^1$ and $R^5$ are D.

In some embodiments, b>0 and at least one $R^2$ is alkyl. In some embodiments, the alkyl group is deuterated. In some embodiments, b=4, one $R^2$ is alkyl and the remainder are D.

In some embodiments, c>0 and at least one $R^3$ is alkyl. In some embodiments, the alkyl group is deuterated. In some embodiments, c=4, one $R^3$ is alkyl and the remainder are D. In some embodiments, c=4, two $R^3$ are alkyl and two $R^3$ are D.

In some embodiments, d>0 and at least one $R^4$ is alkyl. In some embodiments, the alkyl group is deuterated. In some embodiments, d=4, one $R^4$ is alkyl and the remainder are D.

In some embodiments, f=h=2.

In some embodiments, g=1.

In some embodiments, the compounds having Formula I or Formula I' have high triplet energies. The term "triplet energy" refers to the lowest excited triplet state of a material, in eV. Triplet energies are reported as positive numbers and represent the energy of the triplet state relative to the ground state, usually a singlet state. Luminescent organometallic materials emit from excited states having mixed singlet and triplet character and are referred to herein as "phosphorescent". When organometallic phosphorescent materials are used in the light-emitting layer, the presence of materials having low triplet energy leads to quenching of phosphorescent emission of >2.0 eV energy. This leads to decreased efficiency. Quenching can occur when the materials are in the electroluminescent layer, such as a host material, or in a layer adjacent to the electroluminescent layer, such as a hole transport layer. In some embodiments, the material having Formula I or Formula I' has a triplet energy level greater than 2.1 eV; in some embodiments, greater than 2.2 eV; in some embodiments, greater than 2.45 eV; in some embodiments, greater than 2.6 eV. The triplet energy can either be calculated a priori, or be measured using pulse radiolysis or low temperature luminescence spectroscopy.

Some non-limiting examples of compounds having Formula I or Formula I' include Compounds A through EE below.

Compound A

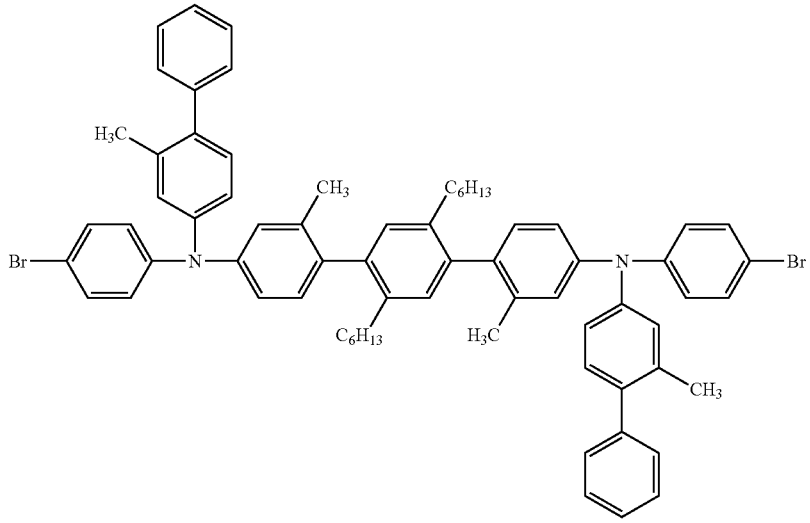

Compound B

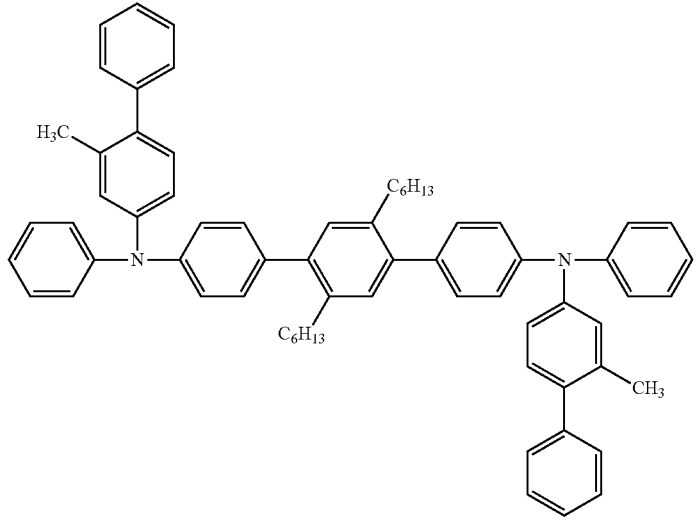

-continued
Compound C
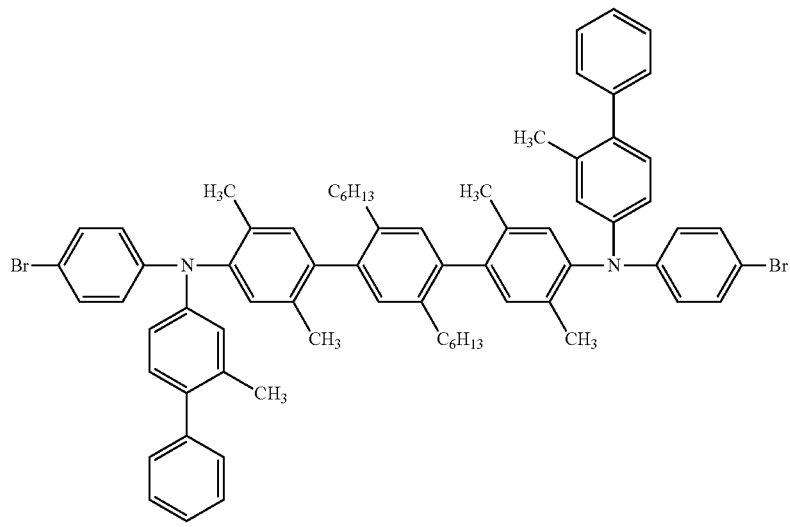
Compound D
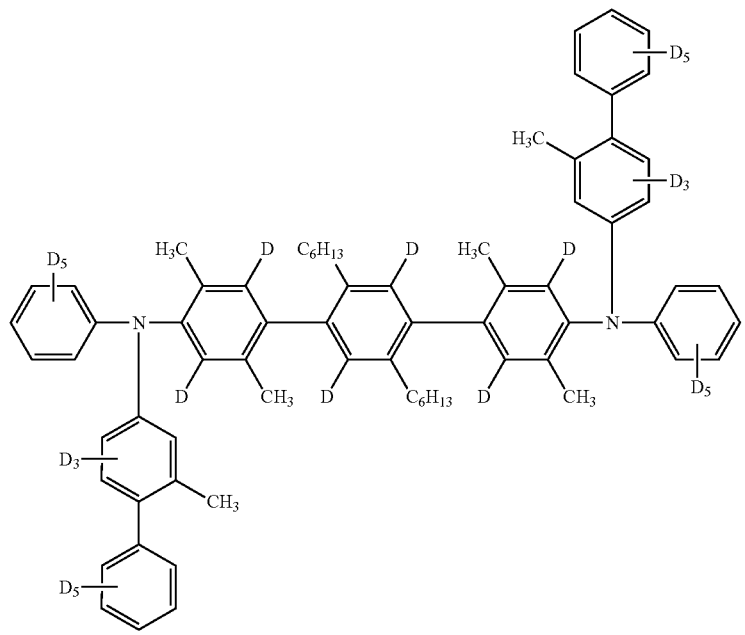
Compound E
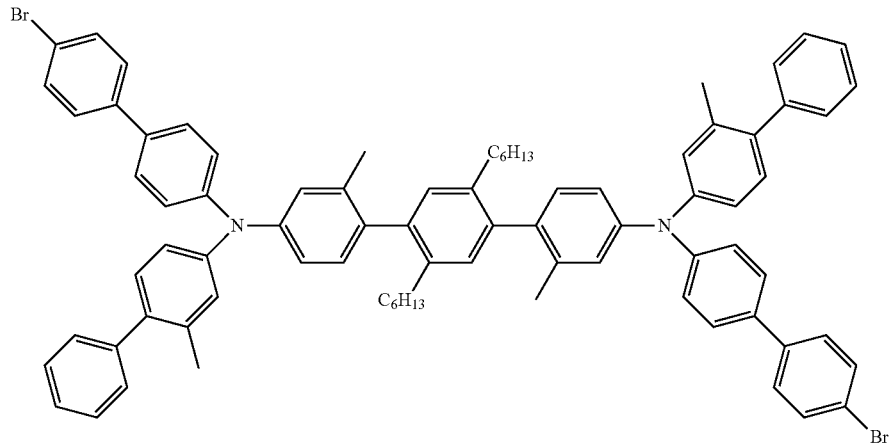

-continued
Compound F
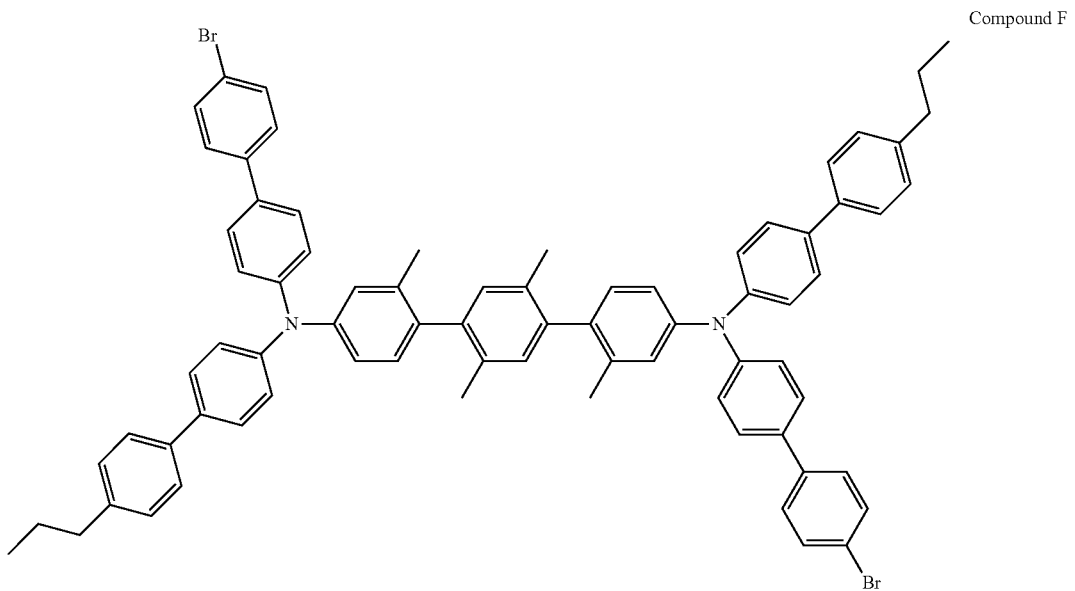
Compound G
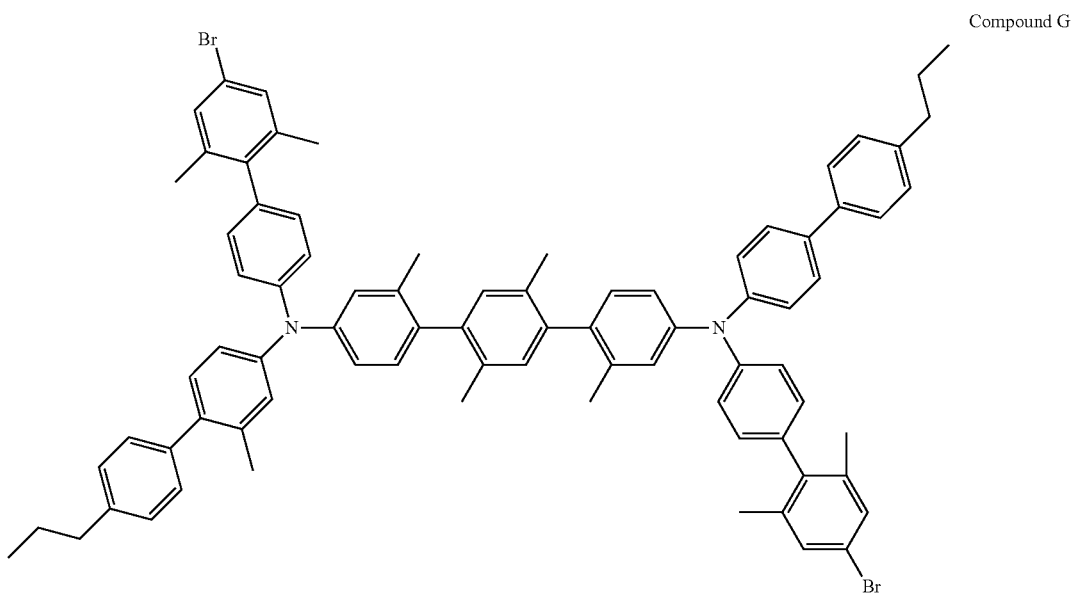

Compound H
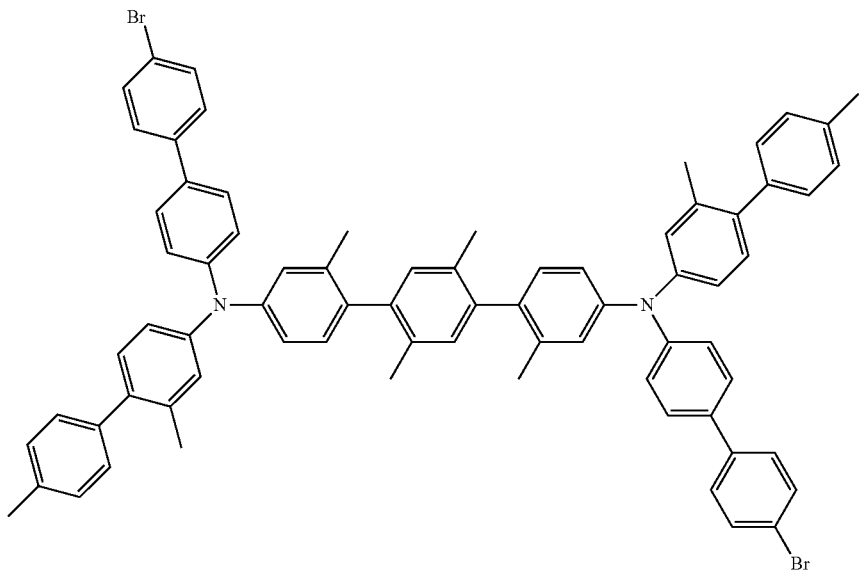
Compound I
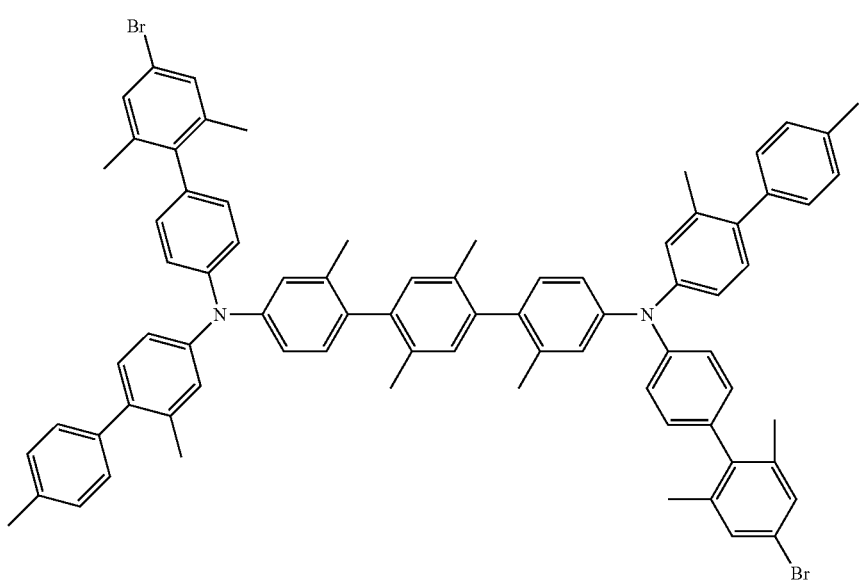

Compound J
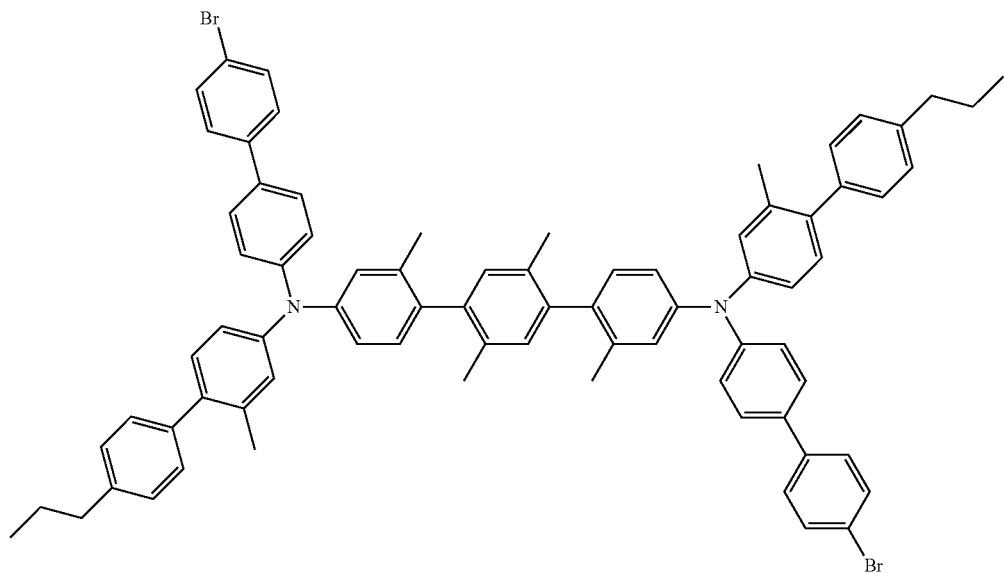
Compound K
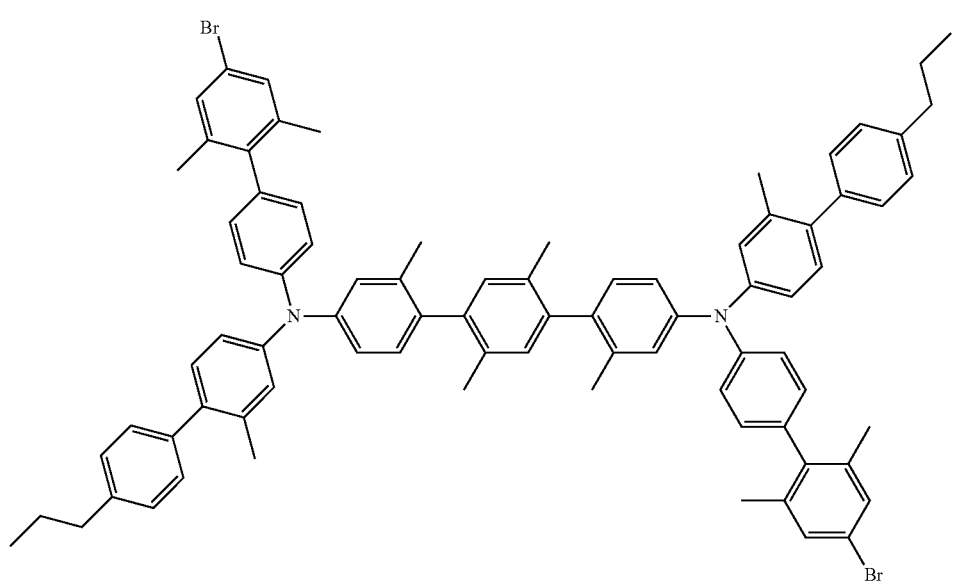

Compound L
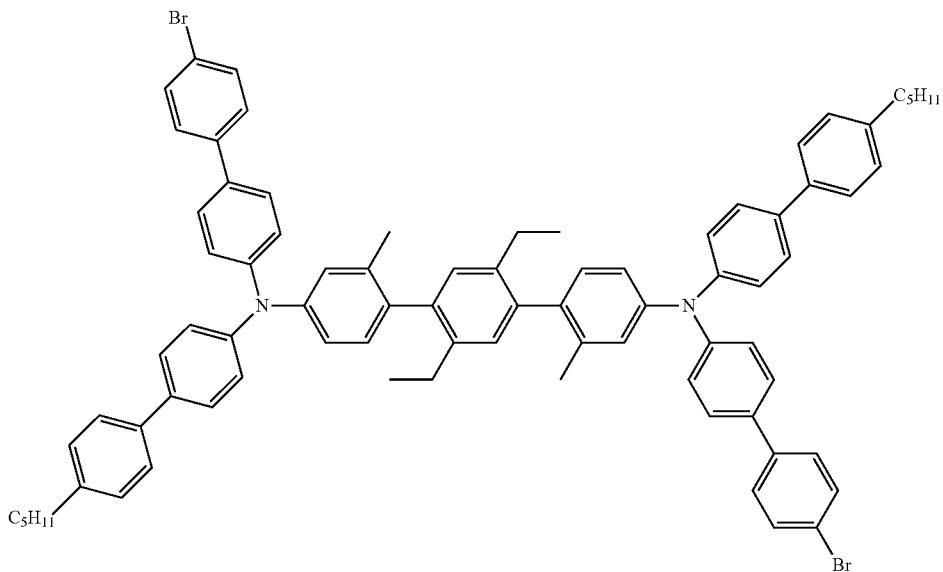
Compound M
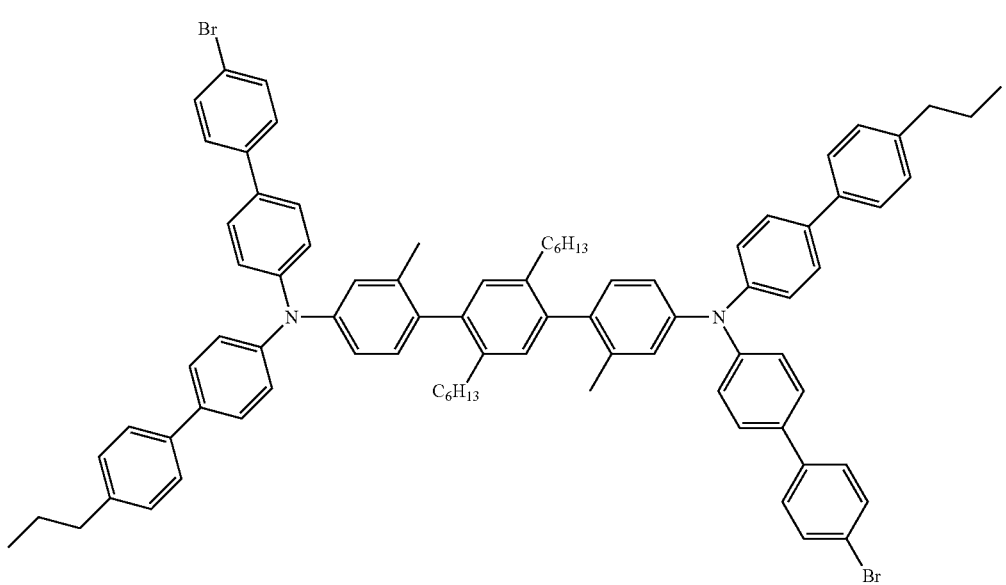

-continued
Compound N
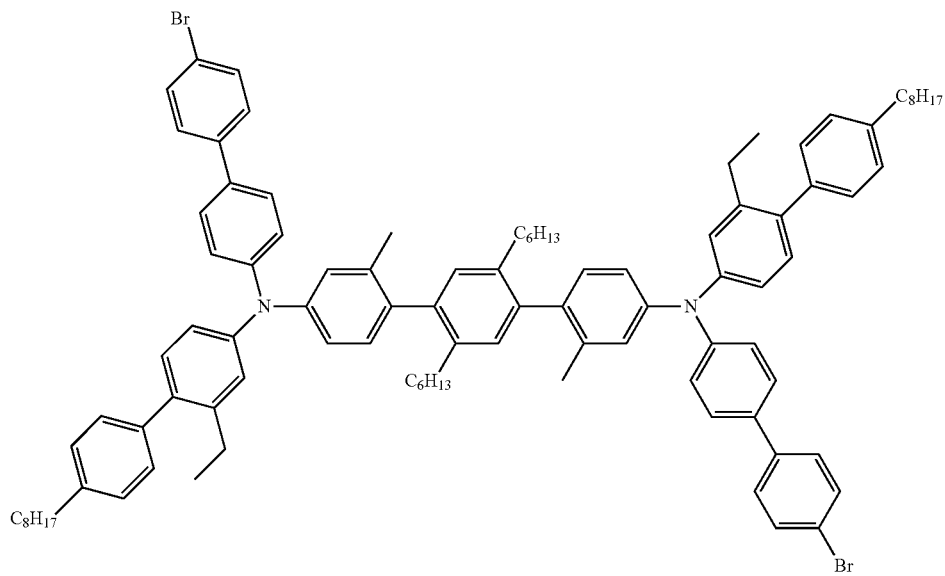
Compound O
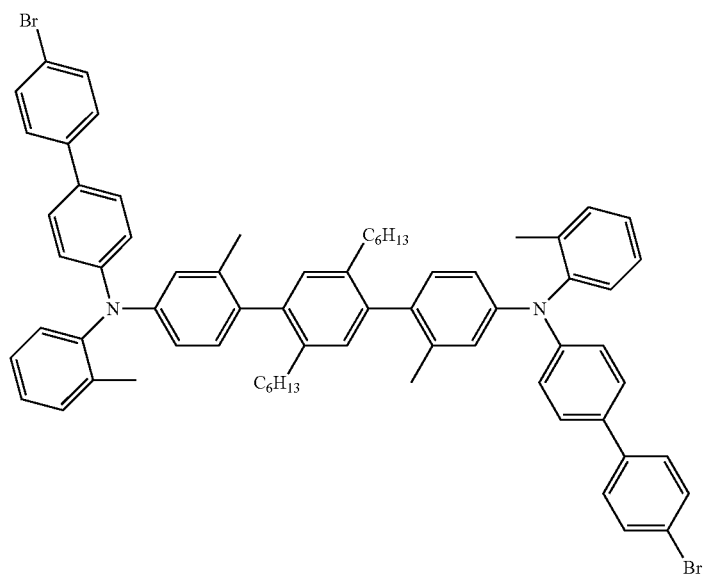
Compound P
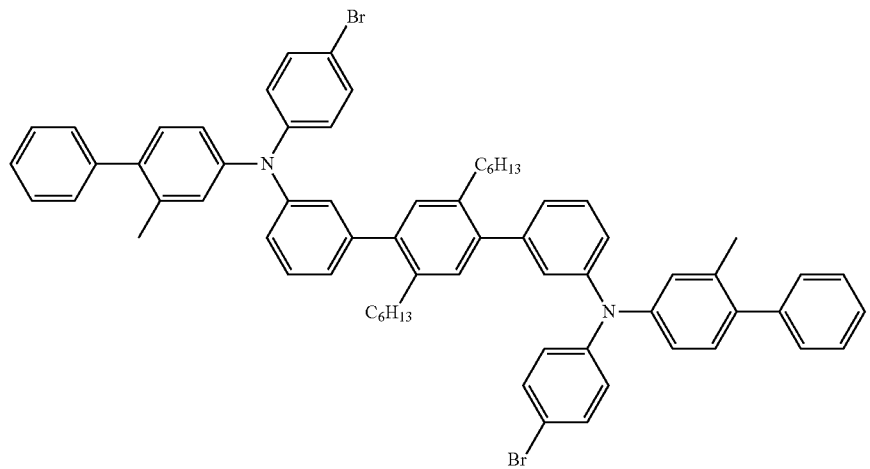

Compound Q
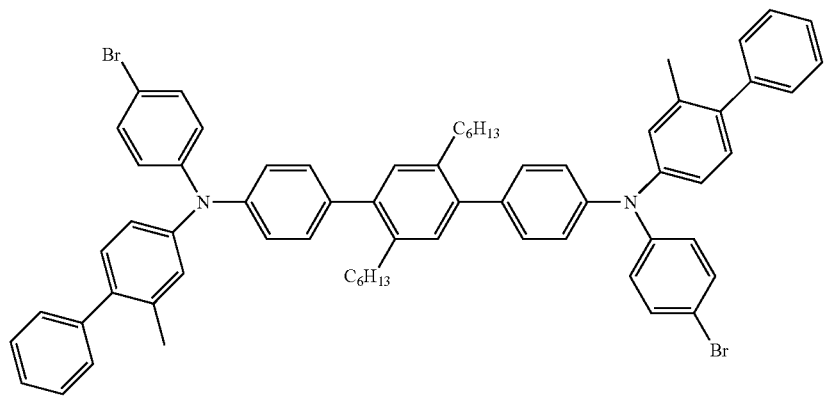
Compound R
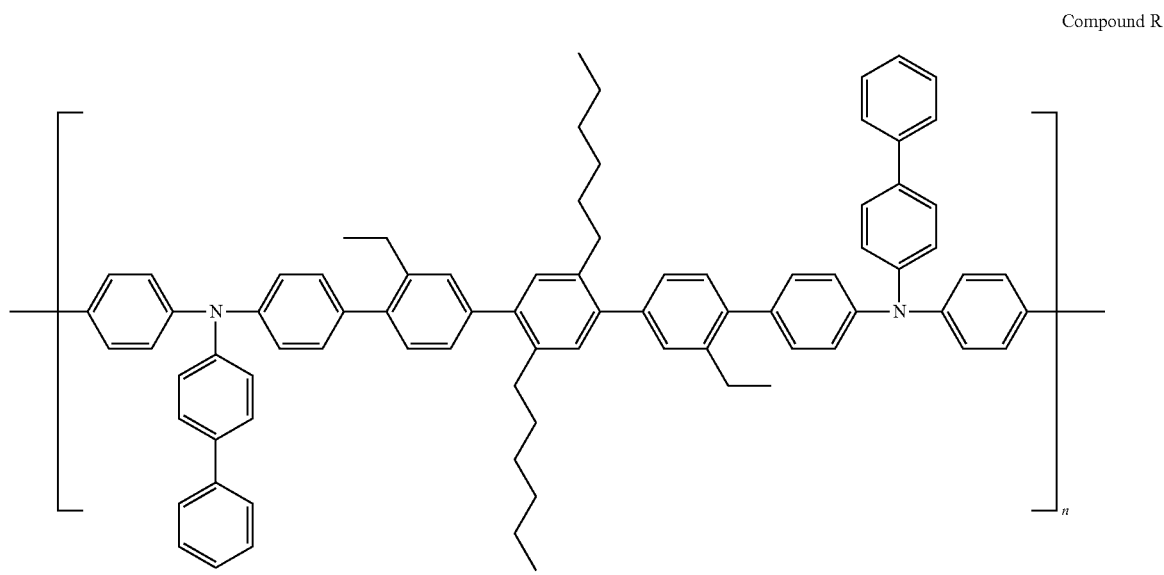
Compound S
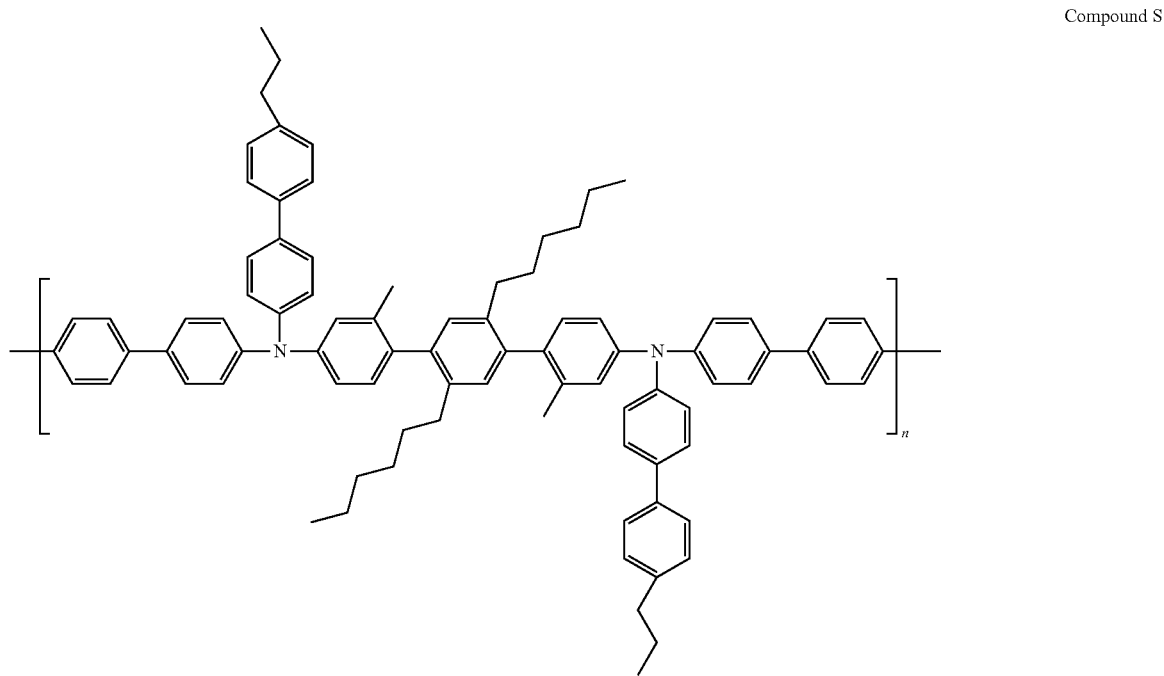

-continued
Compound T
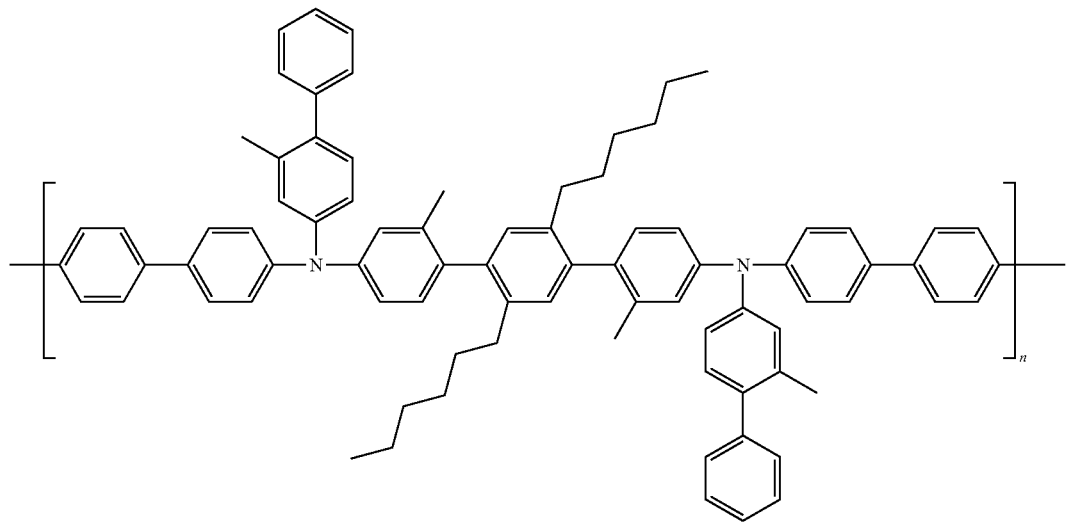
Compound U
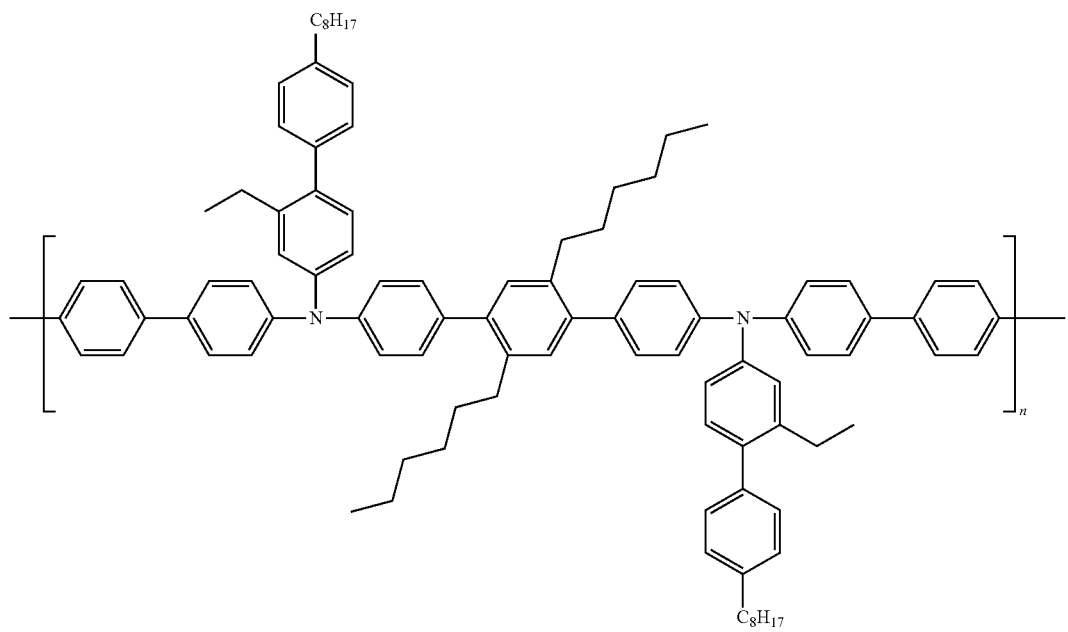
Compound V
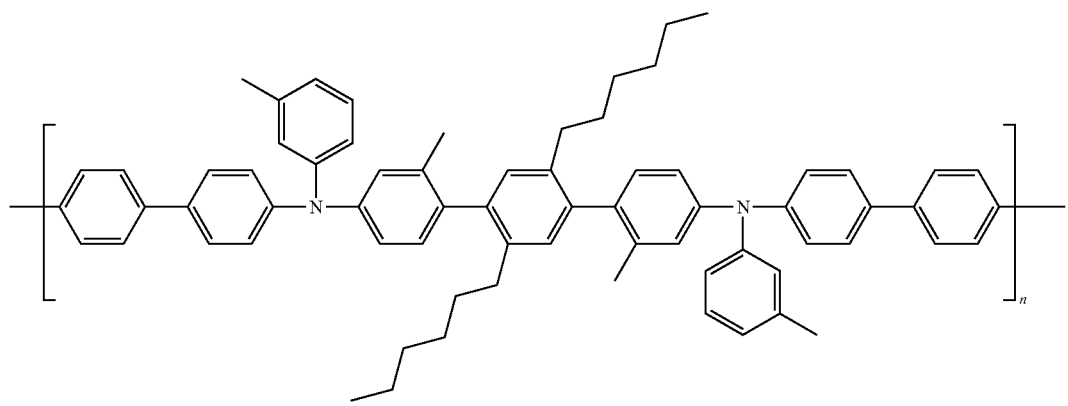

-continued
Compound W
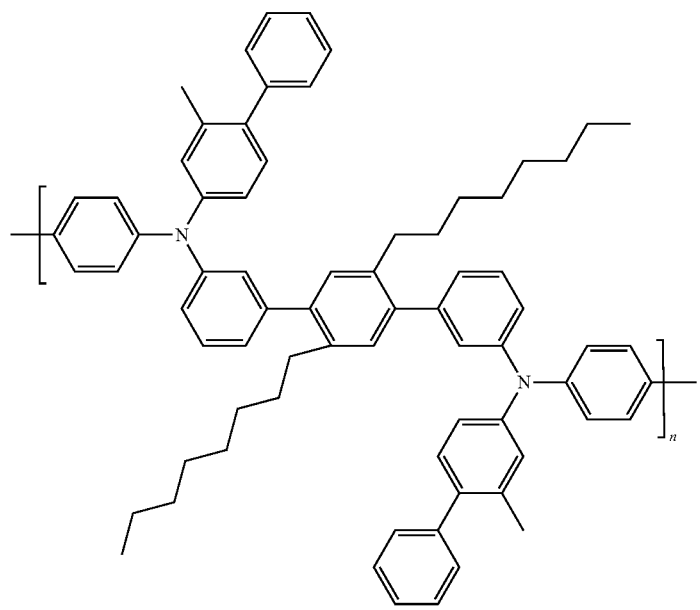
Compound X
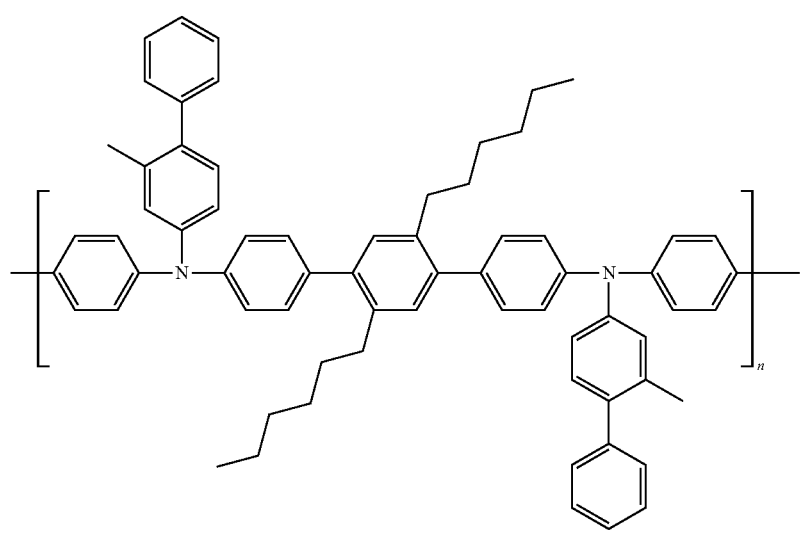

Compound Y
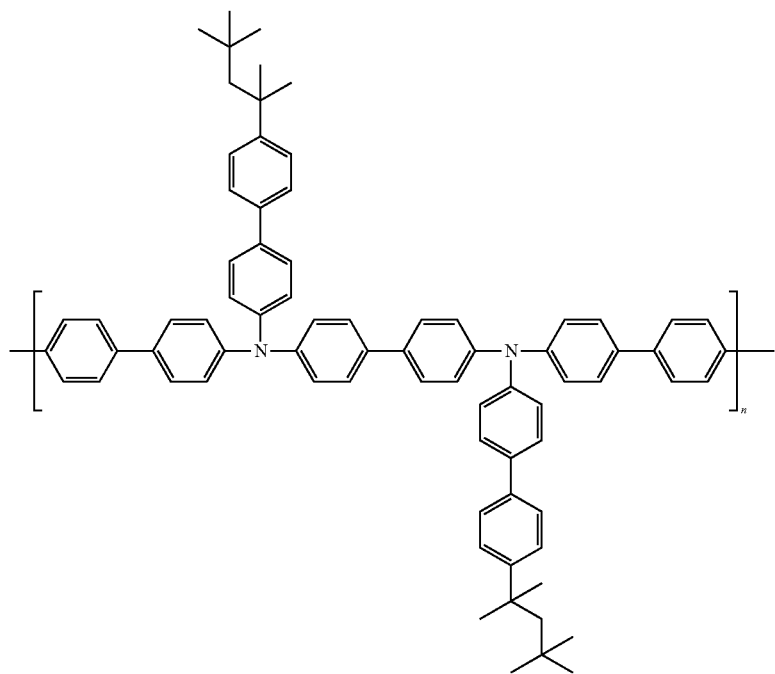
Compound Z
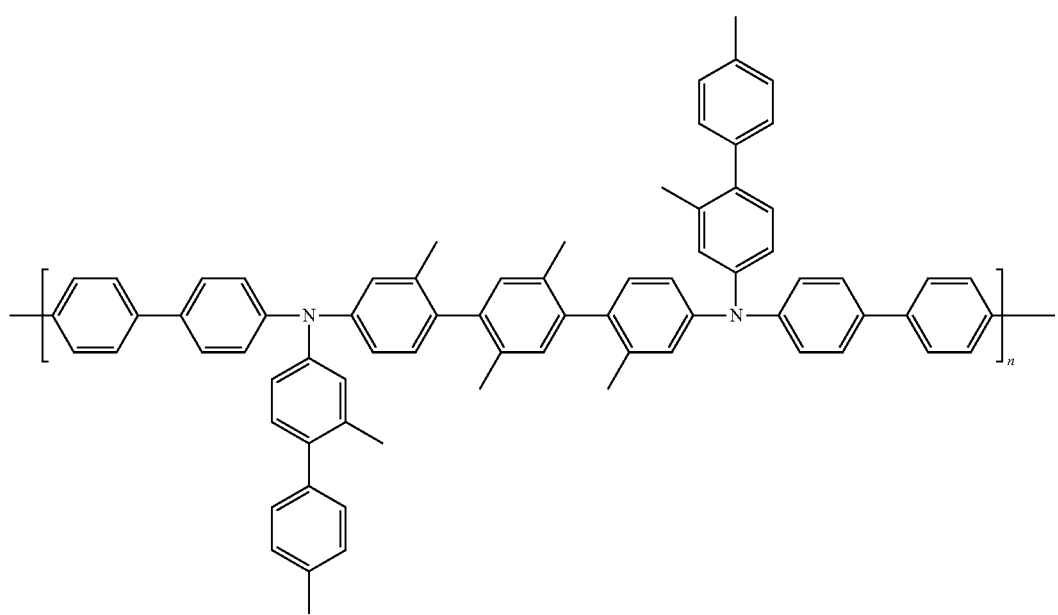

Compound AA
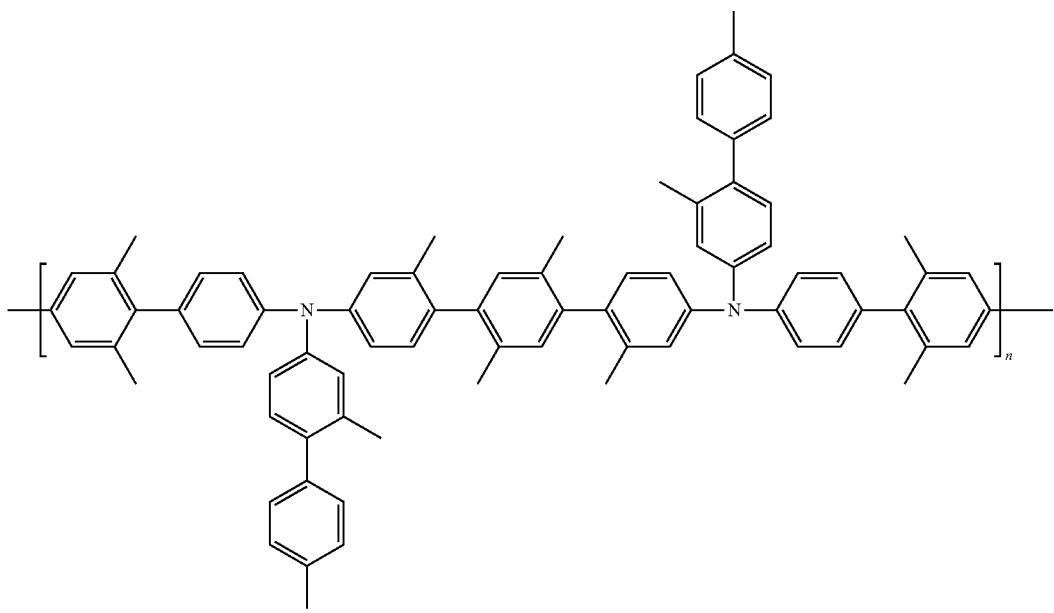
Compound BB
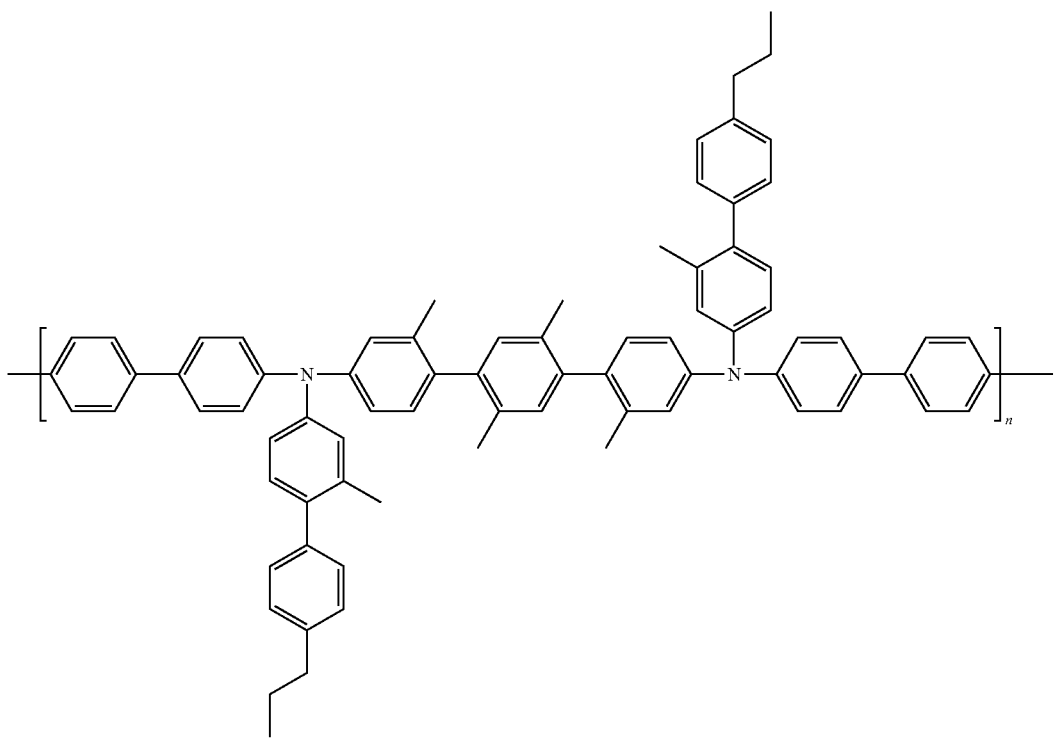

Compound CC
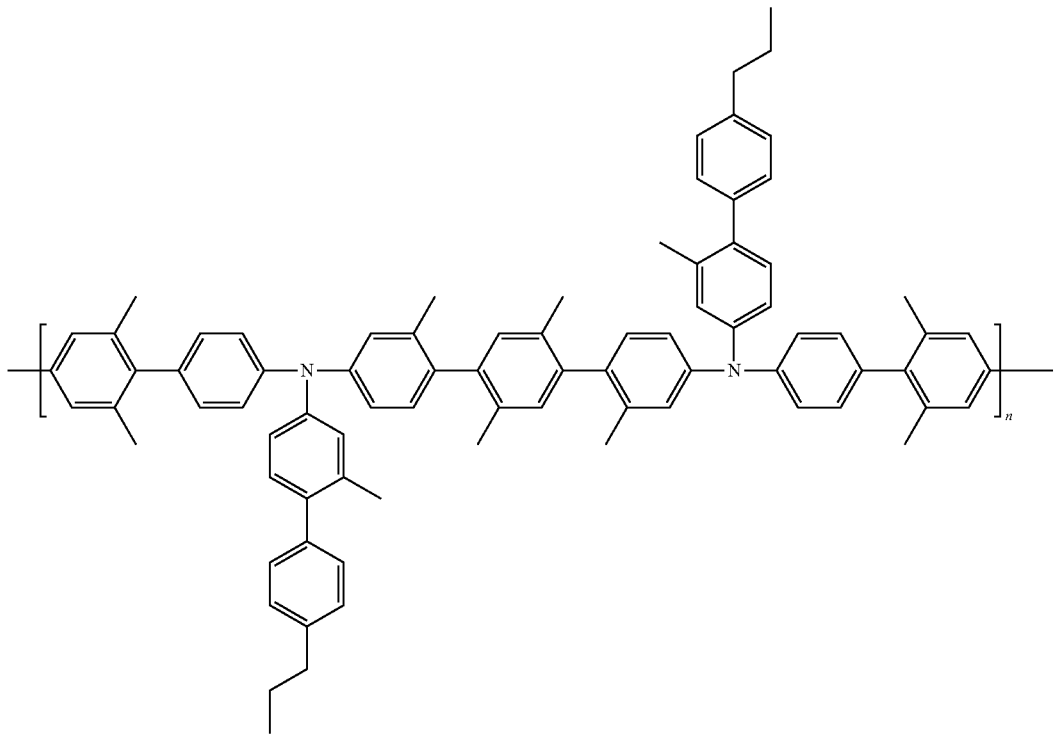
Compound DD
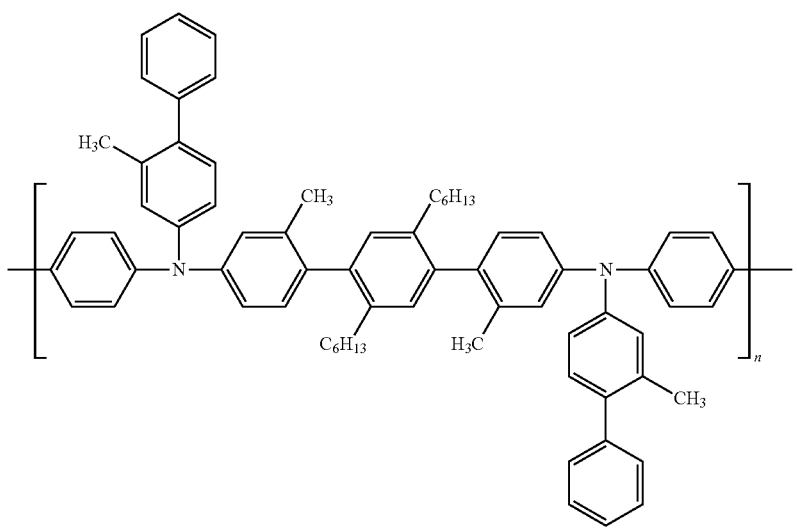

-continued

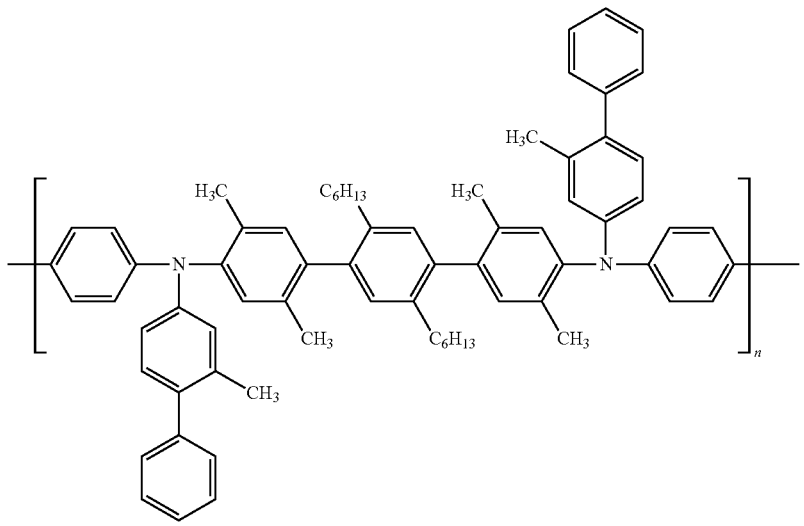

Compound EE

The new compounds can be made using any technique that yield a C—C or C—N bond. A variety of such techniques are known, such as Suzuki, Yamamoto, Stille, and Pd- or Ni-catalyzed C—N couplings. Deuterated compounds can be prepared in a similar manner using deuterated precursor materials or, more generally, by treating the non-deuterated compound with deuterated solvent, such as d6-benzene, in the presence of a Lewis acid H/D exchange catalyst, such as aluminum trichloride or ethyl aluminum dichloride. Exemplary preparations are given in the Examples.

The compounds can be formed into layers using solution processing techniques. The term "layer" is used interchangeably with the term "film" and refers to a coating covering a desired area. The term is not limited by size. The area can be as large as an entire device or as small as a specific functional area such as the actual visual display, or as small as a single sub-pixel. Layers and films can be formed by any conventional deposition technique, including vapor deposition, liquid deposition (continuous and discontinuous techniques), and thermal transfer. Continuous deposition techniques, include but are not limited to, spin coating, gravure coating, curtain coating, dip coating, slot-die coating, spray coating, and continuous nozzle coating. Discontinuous deposition techniques include, but are not limited to, ink jet printing, gravure printing, and screen printing.

The new compounds described herein can be used as hole transport materials, as electroluminescent materials, and as hosts for electroluminescent materials. The new compounds have hole mobilities and HOMO/LUMO energies similar to efficient small molecule hole transport compounds such as N,N'-diphenyl-N,N'-bis(3-methylphenyl)-[1,1'-biphenyl]-4,4'-diamine (TPD). Compounds such as TPD generally must be applied using a vapor deposition technique.

3. Electronic Devices

Organic electronic devices that may benefit from having one or more layers comprising at least one compound as described herein include, but are not limited to, (1) devices that convert electrical energy into radiation (e.g., a light-emitting diode, light emitting diode display, lighting device, luminaire, or diode laser), (2) devices that detect signals through electronics processes (e.g., photodetectors, photoconductive cells, photoresistors, photoswitches, phototransistors, phototubes, IR detectors, biosensors), (3) devices that convert radiation into electrical energy, (e.g., a photovoltaic device or solar cell), and (4) devices that include one or more electronic components that include one or more organic semi-conductor layers (e.g., a transistor or diode). Other uses for the compositions according to the present invention include coating materials for memory storage devices, antistatic films, biosensors, electrochromic devices, solid electrolyte capacitors, energy storage devices such as a rechargeable battery, and electromagnetic shielding applications.

One illustration of an organic electronic device structure is shown in FIG. 1. The device 100 has a first electrical contact layer, an anode layer 110 and a second electrical contact layer, a cathode layer 160, and an electroactive layer 140 between them. In some embodiments, electroactive layer 140 is an electroluminescent layer. Additional layers may optionally be present. Adjacent to the anode may be a hole injection layer 120, sometimes referred to as a buffer layer. Adjacent to the hole injection layer may be a hole transport layer 130, comprising hole transport material. Adjacent to the cathode may be an electron transport layer 150, comprising an electron transport material. As an option, devices may use one or more additional hole injection or hole transport layers (not shown) next to the anode 110 and/or one or more additional electron injection or electron transport layers (not shown) next to the cathode 160. Layers 120 through 150 are individually and collectively referred to as the active layers.

Figure 2:
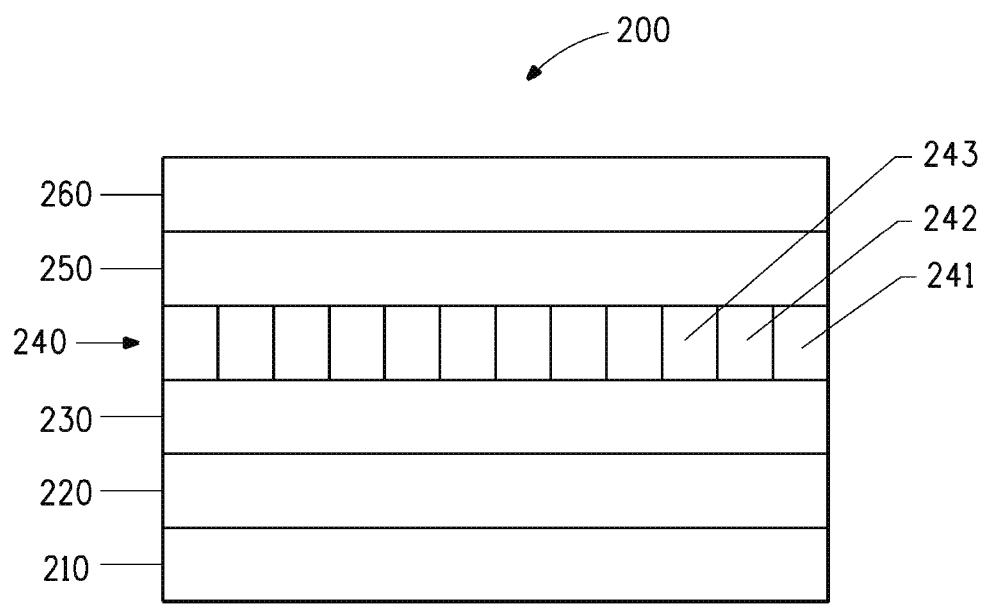
FIG. 2 includes another illustration of an organic electronic device.

In some embodiments, in order to achieve full color, the light-emitting layer is pixelated, with subpixel units for each of the different colors. An illustration of a pixelated device is shown in FIG. 2. The device 200 has anode 210, hole injection layer 220, hole transport layer 230, electroluminescent layer 240, electron transport layer 250, and cathode 260. The electroluminescent layer is divided into subpixels 241, 242, 243, which are repeated across the layer. In some embodiments, the subpixels represent red, blue and green color emission. Although three different subpixel units are depicted in FIG. 2, two or more than three subpixel units may be used.

The different layers will be discussed further herein with reference to FIG. 1. However, the discussion applies to FIG. 2 and other configurations as well.

In one embodiment, the different layers have the following range of thicknesses: anode 110, 500-5000 Å, in one embodiment 1000-2000 Å; hole injection layer 120, 50-2000 Å, in one embodiment 200-1000 Å; hole transport layer 130, 50-2000 Å, in one embodiment 200-1000 Å; electroluminescent layer 140, 10-2000 Å, in one embodiment 100-1000 Å; electron transport layer 150, 50-2000 Å, in one embodiment 100-1000 Å; cathode 160, 200-10000 Å, in one embodiment 300-5000 Å. The desired ratio of layer thicknesses will depend on the exact nature of the materials used.

One or more of the new compounds having Formula I or Formula I' described herein may be present in one or more of the active layers of a device. In some embodiments, the new compounds are useful as hole transport materials in layer 130. In some embodiments, the new compounds are useful as host materials for electroactive dopant materials in electroactive layer 140. The term "dopant" is intended to mean a material, within a layer including a host material, that changes the electronic characteristic(s) or the targeted wavelength(s) of radiation emission, reception, or filtering of the layer compared to the electronic characteristic(s) or the wavelength(s) of radiation emission, reception, or filtering of the layer in the absence of such material. The term "host material" is intended to mean a material to which a dopant is added. The host material may or may not have electronic characteristic(s) or the ability to emit, receive, or filter radiation. In some embodiments, the host material is present in higher concentration.

The anode 110 is an electrode that is particularly efficient for injecting positive charge carriers. It can be made of, for example materials containing a metal, mixed metal, alloy, metal oxide or mixed-metal oxide, or it can be a conducting polymer, and mixtures thereof. Suitable metals include the Group 11 metals, the metals in Groups 4, 5, and 6, and the Group 8-10 transition metals. If the anode is to be light-transmitting, mixed-metal oxides of Groups 12, 13 and 14 metals, such as indium-tin-oxide, are generally used. The anode may also comprise an organic material such as polyaniline as described in "Flexible light-emitting diodes made from soluble conducting polymer," Nature vol. 357, pp 477 479 (11 Jun. 1992). At least one of the anode and cathode should be at least partially transparent to allow the generated light to be observed.

Optional hole injection layer 120 comprises hole injection materials. The term "hole injection layer" or "hole injection material" is intended to mean electrically conductive or semiconductive materials and may have one or more functions in an organic electronic device, including but not limited to, planarization of the underlying layer, charge transport and/or charge injection properties, scavenging of impurities such as oxygen or metal ions, and other aspects to facilitate or to improve the performance of the organic electronic device. Hole injection materials may be polymers, oligomers, or small molecules, and may be in the form of solutions, dispersions, suspensions, emulsions; colloidal mixtures, or other compositions.

The hole injection layer can be formed with polymeric materials, such as polyaniline (PANI) or polyethylenedioxythiophene (PEDOT), which are often doped with protonic acids. The protonic acids can be, for example, poly(styrenesulfonic acid), poly(2-acrylamido-2-methyl-1-propanesulfonic acid), and the like. The hole injection layer 120 can comprise charge transfer compounds, and the like, such as copper phthalocyanine and the tetrathiafulvalene-tetracyanoquinodimethane system (TTF-TCNQ). In one embodiment, the hole injection layer 120 is made from a dispersion of a conducting polymer and a colloid-forming polymeric acid. Such materials have been described in, for example, published U.S. patent applications 2004-0102577, 2004-0127637, and 2005-0205860.

Layer 130 comprises hole transport material. In some embodiments, the hole transport layer comprises a compound having Formula I or Formula I'. In some embodiments, the hole transport layer consists essentially of a compound having Formula I or Formula I'.

In some embodiments, layer 130 comprises other hole transport material. Examples of hole transport materials for the hole transport layer have been summarized for example, in Kirk-Othmer Encyclopedia of Chemical Technology, Fourth Edition, Vol. 18, p. 837-860, 1996, by Y. Wang. Both hole transporting small molecules and polymers can be used. Commonly used hole transporting molecules include, but are not limited to: 4,4',4''-tris(N,N-diphenyl-amino)-triphenylamine (TDATA); 4,4',4''-tris(N-3-methylphenyl-N-phenyl-amino)-triphenylamine (MTDATA); N,N'-diphenyl-N,N'-bis(3-methylphenyl)-[1,1'-biphenyl]-4,4'-diamine (TPD); 4,4'-bis(carbazol-9-yl)biphenyl (CBF); 1,3-bis(carbazol-9-yl)benzene (mCP); 1,1-bis[(di-4-tolylamino)phenyl]cyclohexane (TAPC); N,N'-bis(4-methylphenyl)-N,N'-bis(4-ethylphenyl)-[1,1'-(3,3'-dimethyl)biphenyl]-4,4'-diamine (ETPD); tetrakis-(3-methylphenyl)-N,N,N',N'-2,5-phenylenediamine (FDA); α-phenyl-4-N,N-diphenylaminostyrene (TPS); p-(diethylamino)benzaldehyde diphenylhydrazone (DEH); triphenylamine (TPA); bis[4-(N,N-diethylamino)-2-methylphenyl](4-methylphenyl)methane (MPMP); 1-phenyl-3-[p-(diethylamino)styryl]-5-[p-(diethylamino)phenyl]pyrazoline (PPR or DEASP); 1,2-trans-bis(9H-carbazol-9-yl)cyclobutane (DCZB); N,N,N',N'-tetrakis(4-methylphenyl)-(1,1'-biphenyl)-4,4'-diamine (TTB); N,N'-bis(naphthalen-1-yl)-N,N'-bis-(phenyl)benzidine (α-NPB); and porphyrinic compounds, such as copper phthalocyanine. Commonly used hole transporting polymers include, but are not limited to, polyvinylcarbazole, (phenylmethyl)polysilane, poly(dioxythiophenes), polyanilines, and polypyrroles. It is also possible to obtain hole transporting polymers by doping hole transporting molecules such as those mentioned above into polymers such as polystyrene and polycarbonate. In some cases, triarylamine polymers are used, especially triarylamine-fluorene copolymers. In some cases, the polymers and copolymers are crosslinkable. Examples of crosslinkable hole transport polymers can be found in, for example, published US patent application 2005-0184287 and published PCT application WO 2005/052027. In some embodiments, the hole transport layer is doped with a p-dopant, such as tetrafluorotetracyanoquinodimethane and perylene-3,4,9,10-tetracarboxylic-3,4,9,10-dianhydride.

Depending upon the application of the device, the electroactive layer 140 can be a light-emitting layer that is activated by an applied voltage (such as in a light-emitting diode or light-emitting electrochemical cell), a layer of material that responds to radiant energy and generates a signal with or without an applied bias voltage (such as in a photodetector). In one embodiment, the electroactive layer comprises an organic electroluminescent ("EL") material. Any EL material can be used in the devices, including, but not limited to, small molecule organic fluorescent compounds, fluorescent and phosphorescent metal complexes, conjugated polymers, and mixtures thereof. Examples of fluorescent compounds include, but are not limited to, chrysenes, pyrenes, perylenes, rubrenes, coumarins, anthracenes, thiadiazoles, derivatives thereof, and mixtures thereof. Examples of metal complexes include, but are not limited to, metal chelated oxinoid compounds, such as tris(8-hydroxyquinolato)aluminum (Alq3); cyclometalated iridium and platinum electroluminescent compounds, such as complexes of iridium with phenylpyridine, phenylquinoline, or phenylpyrimidine ligands as disclosed in Petrov et al., U.S. Pat. No. 6,670,645 and Published PCT Applications WO 03/063555 and WO 2004/016710, and organometallic complexes described in, for example, Published PCT Applications WO 03/008424, WO 03/091688, and WO 03/040257, and mixtures thereof. In some cases the small molecule fluorescent or organometallic materials are deposited as a dopant with a host material to improve processing and/or electronic properties. Examples of conjugated polymers include, but are not limited to poly(phenylenevinylenes), polyfluorenes, poly(spirobifluorenes), polythiophenes, poly(p-phenylenes), copolymers thereof, and mixtures thereof.

In some embodiments, electroactive layer 140 comprises an electroluminescent material in a host material having Formula I or Formula I'. In some embodiments, a second host material is also present. In some embodiments, electroactive layer 140 consists essentially of an electroluminescent material and a host material having Formula I or Formula I'. In some embodiment, electroactive layer 140 consists essentially of an electroluminescent material, a first host material having Formula I or Formula I', and a second host material. Examples of second host materials include, but are not limited to, chrysenes, phenanthrenes, triphenylenes, phenanthrolines, naphthalenes, anthracenes, quinolines, isoquinolines, quinoxalines, phenylpyridines, benzodifurans, and metal quinolinate complexes.

Optional layer 150 can function both to facilitate electron transport, and also serve as a hole injection layer or confinement layer to prevent quenching of the exciton at layer interfaces. Preferably, this layer promotes electron mobility and reduces exciton quenching. Examples of electron transport materials which can be used in the optional electron transport layer 150, include metal chelated oxinoid compounds, including metal quinolate derivatives such as tris (8-hydroxyquinolato)aluminum (AlQ), bis(2-methyl-8-quinolinolato)(p-phenylphenolato) aluminum (BAlq), tetrakis-(8-hydroxyquinolato)hafnium (HfQ) and tetrakis-(8-hydroxyquinolato)zirconium (ZrQ); and azole compounds such as 2-(4-biphenylyl)-5-(4-t-butylphenyl)-1,3,4-oxadiazole (PBD), 3-(4-biphenylyl)-4-phenyl-5-(4-t-butylphenyl)-1,2,4-triazole (TAZ), and 1,3,5-tri(phenyl-2-benzimidazole) benzene (TPBI); quinoxaline derivatives such as 2,3-bis(4-fluorophenyl)quinoxaline; phenanthrolines such as 4,7-diphenyl-1,10-phenanthroline (DPA) and 2,9-dimethyl-4,7-diphenyl-1,10-phenanthroline (DDPA); triazines; fullerenes; and mixtures thereof. In some embodiments, the electron transport material is selected from the group consisting of metal quinolates and phenanthroline derivatives. In some embodiments, the electron transport layer further comprises an n-dopant. N-dopant materials are well known. The n-dopants include, but are not limited to, Group 1 and 2 metals; Group 1 and 2 metal salts, such as LiF, CsF, and $Cs_2CO_3$; Group 1 and 2 metal organic compounds, such as Li quinolate; and molecular n-dopants, such as leuco dyes, metal complexes, such as $W_2(hpp)_4$, where hpp=1,3,4,6,7, 8-hexahydro-2H-pyrimido-[1,2-a]-pyrimidine and cobaltocene, tetrathianaphthacene, bis(ethylenedithio)tetrathiafulvalene, heterocyclic radicals or diradicals, and the dimers, oligomers, polymers, dispiro compounds and polycycles of heterocyclic radical or diradicals.

The cathode 160, is an electrode that is particularly efficient for injecting electrons or negative charge carriers. The cathode can be any metal or nonmetal having a lower work function than the anode. Materials for the cathode can be selected from alkali metals of Group 1 (e.g., Li, Cs), the Group 2 (alkaline earth) metals, the Group 12 metals, including the rare earth elements and lanthanides, and the actinides. Materials such as aluminum, indium, calcium, barium, samarium and magnesium, as well as combinations, can be used. Li-containing organometallic compounds, LiF, $Li_2O$, Cs-containing organometallic compounds, CsF, $Cs_2O$, and $Cs_2CO_3$ can also be deposited between the organic layer and the cathode layer to lower the operating voltage. This layer may be referred to as an electron injection layer.

It is known to have other layers in organic electronic devices. For example, there can be a layer (not shown) between the anode 110 and hole injection layer 120 to control the amount of positive charge injected and/or to provide band-gap matching of the layers, or to function as a protective layer. Layers that are known in the art can be used, such as copper phthalocyanine, silicon oxy-nitride, fluorocarbons, silanes, or an ultra-thin layer of a metal, such as Pt. Alternatively, some or all of anode layer 110, active layers 120, 130, 140, and 150, or cathode layer 160, can be surface-treated to increase charge carrier transport efficiency. The choice of materials for each of the component layers is preferably determined by balancing the positive and negative charges in the emitter layer to provide a device with high electroluminescence efficiency.

It is understood that each functional layer can be made up of more than one layer.

The device layers can be formed by any deposition technique, or combinations of techniques, including vapor deposition, liquid deposition, and thermal transfer. Substrates such as glass, plastics, and metals can be used. Conventional vapor deposition techniques can be used, such as thermal evaporation, chemical vapor deposition, and the like. The organic layers can be applied from solutions or dispersions in suitable solvents, using conventional coating or printing techniques, including but not limited to spin-coating, dip-coating, roll-to-roll techniques, ink-jet printing, continuous nozzle printing, screen-printing, gravure printing and the like.

For liquid deposition methods, a suitable solvent for a particular compound or related class of compounds can be readily determined by one skilled in the art. For some applications, it is desirable that the compounds be dissolved in non-aqueous solvents. Such non-aqueous solvents can be relatively polar, such as $C_1$ to $C_{20}$ alcohols, ethers, and acid esters, or can be relatively non-polar such as $C_1$ to $C_{12}$ alkanes or aromatics such as toluene, xylenes, trifluorotoluene and the like. Other suitable liquids for use in making the liquid composition, either as a solution or dispersion as described herein, comprising the new compounds, includes, but not limited to, chlorinated hydrocarbons (such as methylene chloride, chloroform, chlorobenzene), aromatic hydrocarbons (such as substituted and non-substituted toluenes and xylenes), including trifluorotoluene), polar solvents (such as tetrahydrofuran (THP), N-methylpyrrolidone) esters (such as ethylacetate) alcohols (isopropanol), keytones (cyclopentatone) and mixtures thereof. Suitable solvents for electroluminescent materials have been described in, for example, published POT application WO 2007/145979.

In some embodiments, the device is fabricated by liquid deposition of the hole injection layer, the hole transport layer, and the electroactive layer, and by vapor deposition of the anode, the electron transport layer, an electron injection layer and the cathode.

It is understood that the efficiency of devices made with the new compositions described herein, can be further improved by optimizing the other layers in the device. For example, more efficient cathodes such as Ca, Ba or LiF can be used. Shaped substrates and novel hole transport materials that result in a reduction in operating voltage or increase quantum efficiency are also applicable. Additional layers can also be added to tailor the energy levels of the various layers and facilitate electroluminescence.

In one embodiment, the device has the following structure, in order: anode, hole injection layer, hole transport layer, electroactive layer, electron transport layer, electron injection layer, cathode.

Although methods and materials similar or equivalent to those described herein can be used in the practice or testing of the present invention, suitable methods and materials are described below. In addition, the materials, methods, and examples are illustrative only and not intended to be limiting. All publications, patent applications, patents, and other references mentioned herein are incorporated by reference in their entirety.

EXAMPLES

The concepts described herein will be further described in the following examples, which do not limit the scope of the invention described in the claims.

Synthesis Example 1

This example illustrates the preparation of some intermediate compounds.

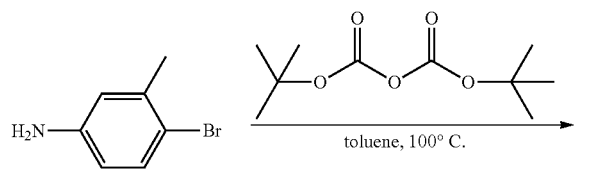

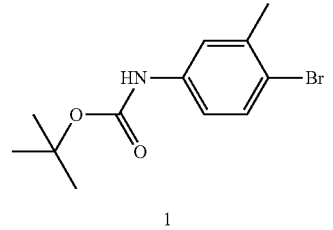

The reaction mixture of 4-bromo-3-methylaniline (11 g, 59.12 mmol) and (Boc)$_2$O (12.9 g, 59.12 mmol) in toluene (110 ml) was stirred at 100° C. for 40 h under nitrogen. After concentration of the reaction mixture under reduced pressure, 15.9 g (94% yield) of boc-NH-4-bromo-3-methylaniline, 1, was obtained as a white solid by column chromatography (5-10% ethyl acetate in hexane),

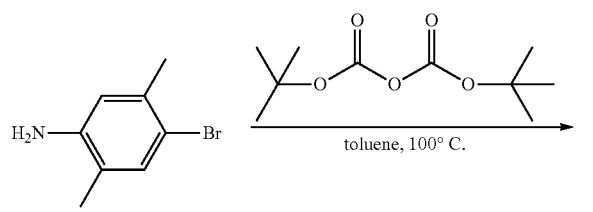

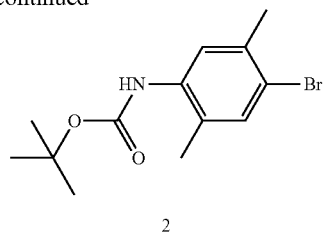

2

The reaction mixture of 4-bromo-2,5-dimethylaniline (5 g, 25 mmol) and (Boc)$_2$O (5.4 g, 25 mmol) in toluene (60 ml) was stirred at 100° C. for 40 hrs under nitrogen. After concentration of the reaction mixture under reduced pressure, 5.82 g (78% yield) of boc-NH-4-bromo-2,5-dimethylaniline, 2, was obtained as a white solid by column chromatography (5-10% ethyl acetate in hexane).

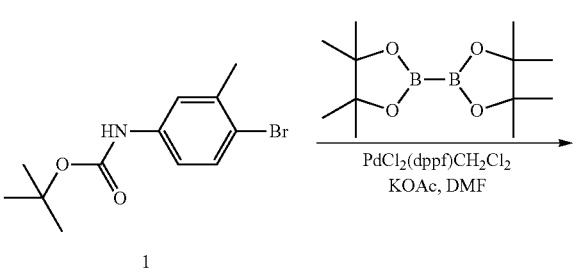

1

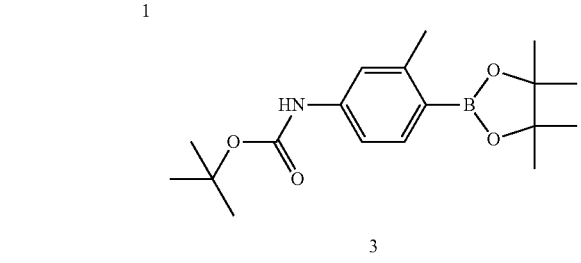

3

In a glove box a mixture of the boc-NH-4-bromo-3-methylaniline, 1, (20.77 g, 72.58 mmol), diboron pinacol ester (22.12 g, 87.09 mmol), 1,1'-bis-(diphenylphosphino) ferrocine palladium dichloride (1.43 g, 1.96 mmol), and potassium acetate (21.37 g, 217.7 mmol) in dry degassed DMF (300 mL) was stirred at 80° C. for 16 hrs in an oil bath. The mixture was cooled to room temperature and concentrated under reduced pressure. DCM (100 mL) was added to the mixture which was filtered through a pad of Celite. The filtrate was concentrated to rusty oil which was purified on a silica gel column chromatography (5-10% EtOAc/hexane) to provide the product, 3, (18.57 g, 77% yield) as a white solid.

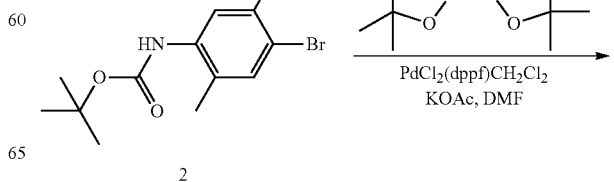

2

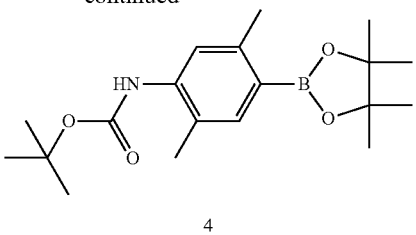

4

In a glove box a mixture of the boc-NH-4-bromo-2,5-dimethylaniline, 2, (5.8 g, 19.32 mmol), diboron pinacol ester (5.88 g, 23.18 mmol), 1,1'-bis-(diphenylphosphino)ferrocine palladium dichloride (0.382 g, 0.522 mmol), and potassium acetate (5.689 g, 57.96 mmol) in dry degassed DMF (300 mL) was stirred at 80° C. for 16 hrs in an oil bath. The mixture was cooled to room temperature and concentrated under reduced pressure. DCM (100 mL) was added to the mixture which was filtered through a pad of Celite. The filtrate was concentrated to give a white solid which was then triturated in hexane to provide the product, 4, (6.45 g, 96% yield) as a white powder.

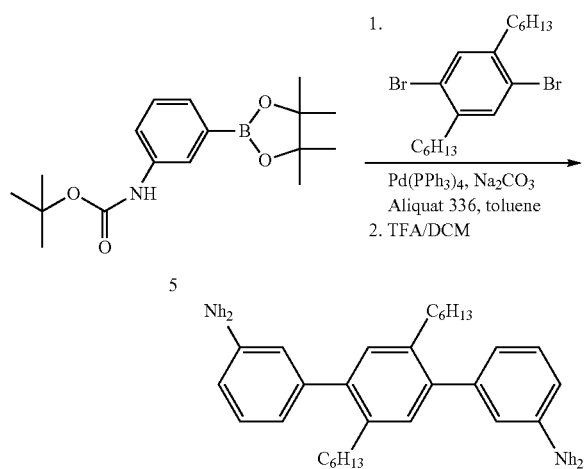

In the dry box the mixture of boronic add 5, (3.69 g, 15.58 mmol), dibromo-2,5-dihexylbenzene (3.15 g, 7.8 mmol), Aliquat 336 (0.8 g), Pd(PPh$_3$)$_4$ (0.858 g, 0.742 mmol) in degassed toluene (50 mL) was prepared. Outside dry box, the degassed Na$_2$CO$_3$(3.93 g, 37.11 mmol in 50 mL of water) solution was added to the former mixture under nitrogen, and then the resultant mixture was stirred at 90° C. for 18 hrs. The organic layer was separated and the aqueous layer was extracted with ethyl acetate. The combined organic layers were dried over anhydrous MgSO$_4$. Filtration, concentration of the filtrate, and then the silica column chromatography (10-50% DCM in hexane) provided the desired product (3.7 g, 80% yield) as a solid. This diboc-protected material was deprotected by the overnight reaction at room temperature with TFA solution (2 mL of TFA in 50 mL of DCM). The reaction mixture was concentrated under reduced pressure followed by the neutralization with saturated NaHCO$_3$. Ethyl acetate extraction, drying over anhydrous MgSO$_4$, concentration of the organic layer under reduced pressure, then silica column chromatography (10-50% ethyl acetate in hexane) provided the desired diamine material, 6, (1.89 g, 75% yield) as a viscous liquid.

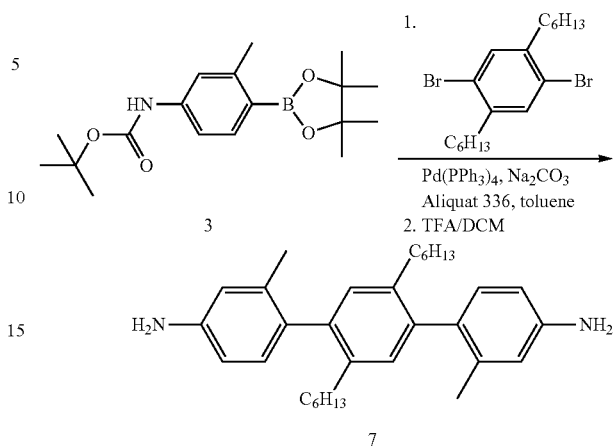

In the dry box the mixture of boronic acid pinacol ester, 3, (5.6 g, 16.82 mmol), 1,4-dibromo-2,5-dihexylbenzene (3.4 g, 8.4 mmol), Aliquat 336 (0.8 g), and Pd(PPh$_3$)$_4$ (0.486 g, 0.421 mmol) in degassed toluene (100 mL) was prepared. Outside dry box, the degassed Na$_2$CO$_3$(2.67 g, 25.23 mmol in 50 mL of water) solution was added to the former mixture under nitrogen, and then the resultant mixture was stirred at 90° C. for 42 hrs. The organic layer was separated and the aqueous layer was extracted with ethyl acetate. The combined organic layers were dried over anhydrous MgSO$_4$. Filtration, concentration of the filtrate, and then the silica column chromatography (0-3% ethyl acetate in hexane) provided the desired product (2.11 g, 38% yield) as a viscous liquid. This diboc-protected material was deprotected by the overnight reaction at room temperature with TFA solution (5 mL of TFA in 50 mL of DCM). The reaction mixture was concentrated under reduced pressure followed by the neutralization with saturated NaHCO$_3$. Ethyl acetate extraction, drying over anhydrous MgSO$_4$, concentration of the organic layer under reduced pressure, then silica column chromatography (30% ethyl acetate in hexane) provided the desired diamine material, 7, (1.16 g, 80% yield) as a viscous liquid.

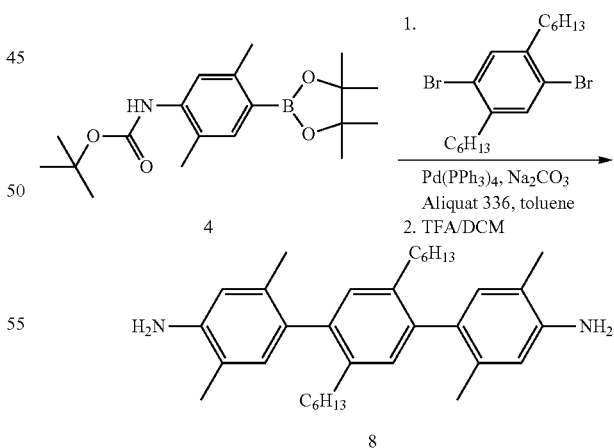

In the dry box the mixture of boronic acid pinacol ester, 4, (6.44 g, 18.55 mmol), 1,4-dibromo-2,5-dihexylbenzene (3.75 g, 9.27 mmol), Aliquat 336 (0.8 g), and Pd(PPh$_3$)$_4$ (0.536 g, 0.464 mmol) in degassed toluene (100 mL) was prepared. Outside dry box, the degassed Na$_2$CO$_3$(2.95 g, 27.83 mmol in 50 mL of water) solution was added to the former mixture under nitrogen, and then the resultant mixture was stirred at 90° C. for 38 hrs. The organic layer was separated and the aqueous layer was extracted with ethyl acetate. The combined organic layers were dried over anhydrous MgSO$_4$. Filtration, concentration of the filtrate, and then the silica column chromatography (0-4% ethyl acetate in hexane) provided the desired product (3.62 g, 60% yield) as a white solid. This diboc-protected material was deprotected by the overnight reaction at room temperature with TFA solution (4 mL of TFA in 30 mL of DCM). The reaction mixture was concentrated under reduced pressure followed by the neutralization with saturated NaHCO$_3$. Ethyl acetate extraction, drying over anhydrous MgSO$_4$, concentration of the organic layer under reduced pressure, then silica column chromatography (30% ethyl acetate in hexane) provided the desired diamine material, 8, (2.5 g, 99% yield).

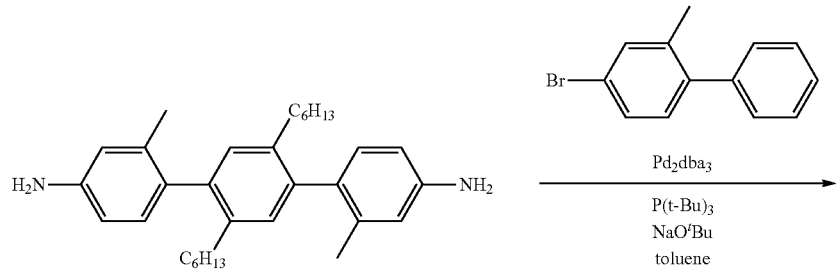

7

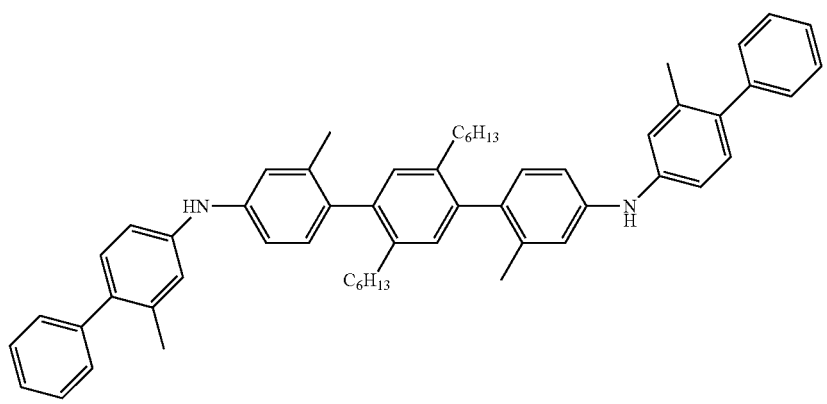

9

To the solution of diamine, 7, (2.77 g, 6.06 mmol) and 2-methyl-4-bromobiphenyl (3.24 g, 12.12 mmol) in toluene (30 mL) was added the solution of pd$_2$ dba$_3$ (362 mg, 0.363 mmol) and P(t-Bu)$_3$ (160 mg, 0.727 mmol) in toluene (20 mL), followed by the addition of NaO$^t$Bu (1.262 g, 12.12 mmol) under nitrogen. The resultant mixture was stirred at room temperature overnight. The mixture was filtered through a short silica bed and the filtrate was concentrated under reduced pressure. By column chromatography (10-30% toluene in hexane) 3.4 g of product 9 was obtained as a solid (71% yield).

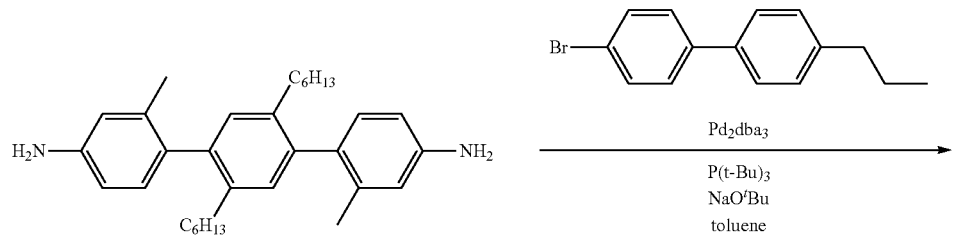

7

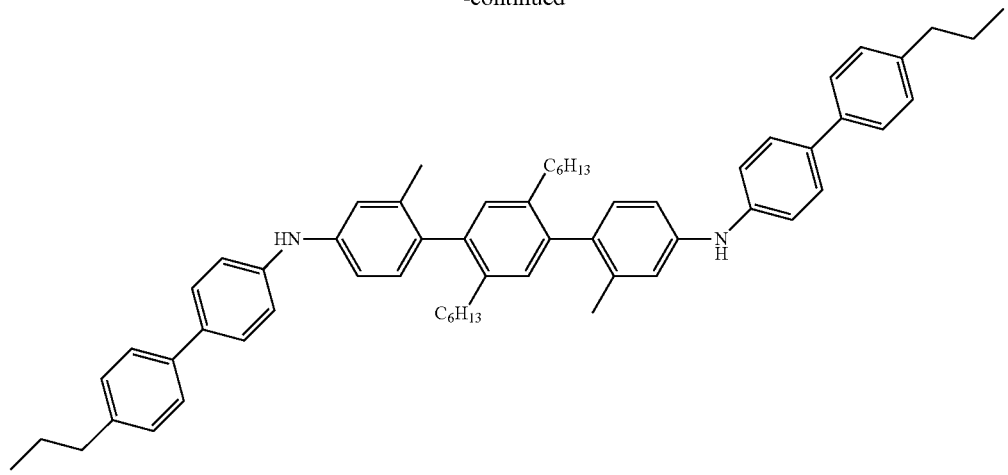

10

To the solution of diamine, 7, (1.06 g, 2.32 mmol) and 4-bromo-4'-propyl-biphenyl (1.28 g, 4.65 mmol) in toluene (20 mL) was added the solution of pd$_2$ dba$_3$ (128 mg, 0.139 mmol) and P(t-Bu)$_3$ (57 mg, 0.278 mmol) in toluene (10 mL), followed by the addition of NaO$^t$Bu (0.45 g, 4.65 mmol) under nitrogen. The resultant mixture was stirred at room temperature overnight. The mixture was filtered through a short silica bed and the filtrate was concentrated under reduced pressure. By column chromatography (10-30% toluene in hexane) 1.35 g of product 10 was obtained as a solid (69% yield).

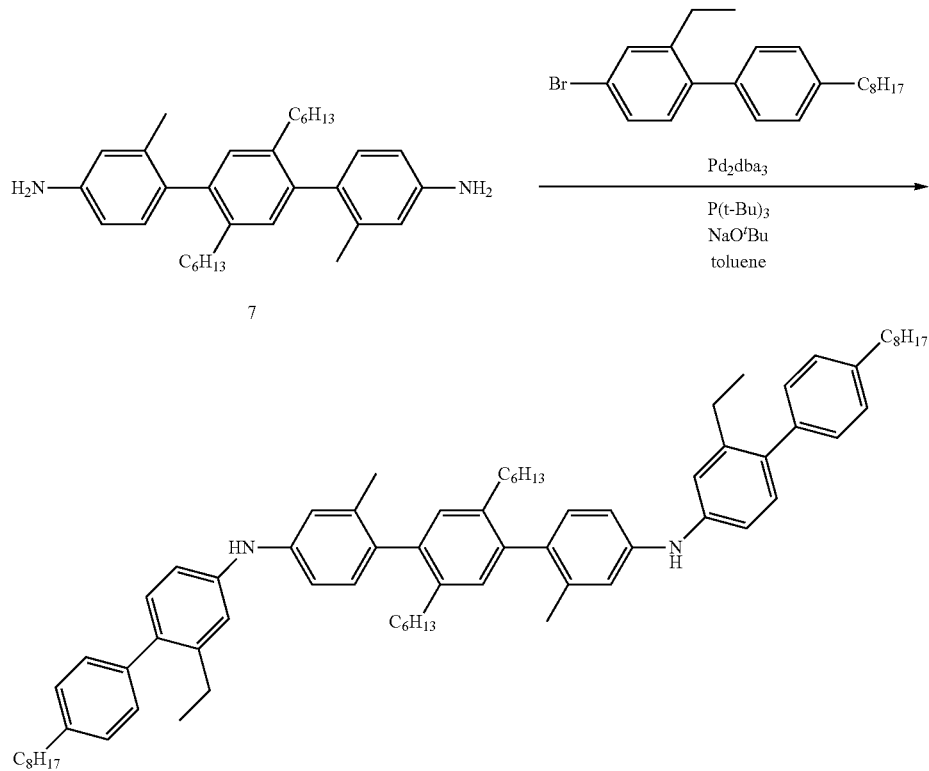

To the solution of diamine, 7, (1 g, 2.19 mmol) and 4-bromo-2-ethyl-4'-octyl-biphenyl (1.635 g, 4.38 mmol) in toluene (30 mL) was added the solution of pd$_2$ dba$_3$ (120 mg, 0.131 mmol) and P(t-Bu)$_3$ (53 mg, 0.262 mmol) in toluene (10 mL), followed by the addition of NaO$^t$Bu (0.421 g, 4.38 mmol) under nitrogen. The resultant mixture was stirred at room temperature overnight. The mixture was filtered through a short silica bed and the filtrate was concentrated under reduced pressure. By column chromatography (5-12% DCM in hexane) 10.34 g of product 11 was obtained as a solid (63% yield).

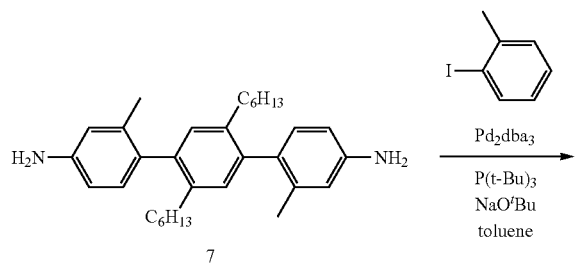

7

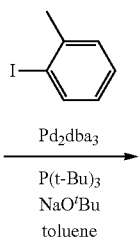

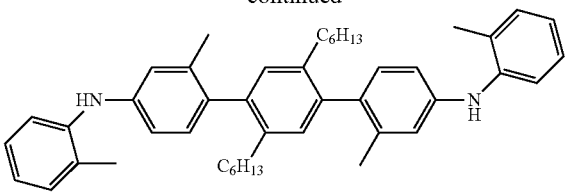

12

To the solution of diamine, 7, (3.16 g, 6.91 mmol) and 2-iodotoluene (3.016 g, 13.83 mmol) in toluene (30 mL) was added the solution of pd$_2$ dba$_3$ (379 mg, 0.414 mmol) and P(t-Bu)$_3$ (167 mg, 0.829 mmol) in toluene (10 mL), followed by the addition of NaO$^t$Bu (1.4 g, 14.51 mmol) under nitrogen. The resultant mixture was stirred at room temperature overnight. The mixture was filtered through a short silica bed and the filtrate was concentrated under reduced pressure. By column chromatography (5-10% toluene in hexane) 3.8 g of product 12 was obtained as a solid (86% yield).

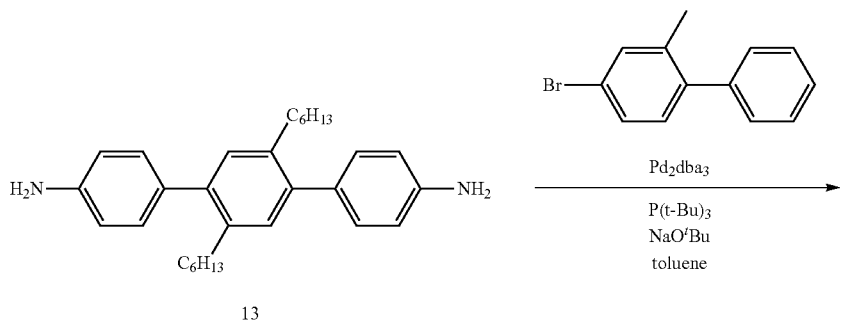

13

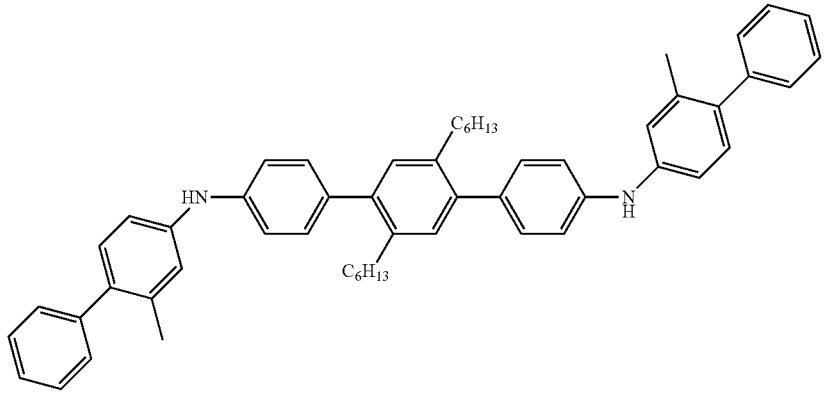

14

To the solution of diamine, 13, (1 g, 2.33 mmol) and 2-methyl-4-bromobiphenyl (1.153 g, 4.66 mmol) in toluene (30 mL) was added the solution of pd$_2$ dba$_3$ (128 mg, 0.14 mmol) and P(t-Bu)$_3$ (57 mg, 0.28 mmol) in toluene (10 mL), followed by the addition of NaO$^t$Bu (0.448 g, 4.66 mmol) under nitrogen. The resultant mixture was stirred at room temperature overnight. The mixture was filtered through a short silica bed and the filtrate was concentrated under reduced pressure. By column chromatography (10-40% toluene in hexane) 1.53 g of product 14 was obtained as a solid (86% yield).

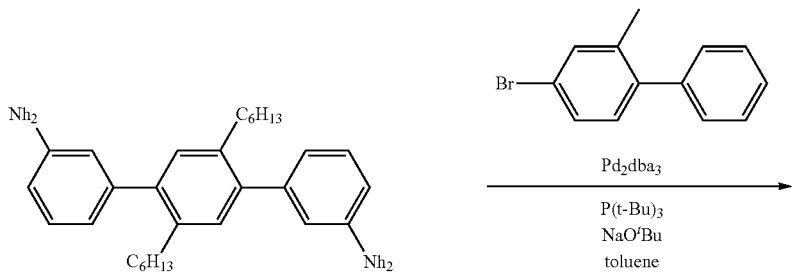

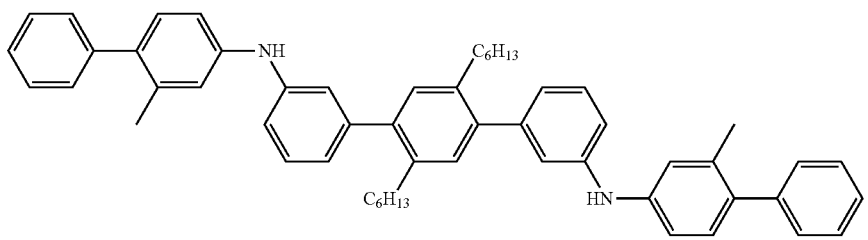

To the solution of diamine, 6, (1 g, 2.33 mmol) and 2-methyl-4-bromobiphenyl (1.153 g, 4.66 mmol) in toluene (30 mL) was added the solution of pd$_2$dba$_3$ (128 mg, 0.14 mmol) and P(t-Bu)$_3$ (57 mg, 0.28 mmol) in toluene (10 mL), followed by the addition of NaO$^t$Bu (0.448 g, 4.66 mmol) under nitrogen. The resultant mixture was stirred at room temperature overnight. The mixture was filtered through a short silica bed and the filtrate was concentrated under reduced pressure. By column chromatography (10-40% toluene in hexane) 1.40 g of product 15 was obtained as a solid (79% yield).

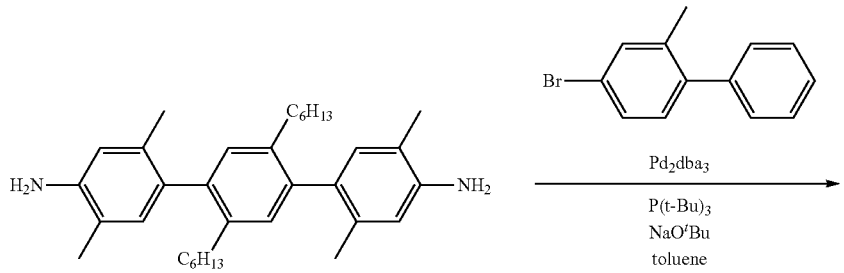

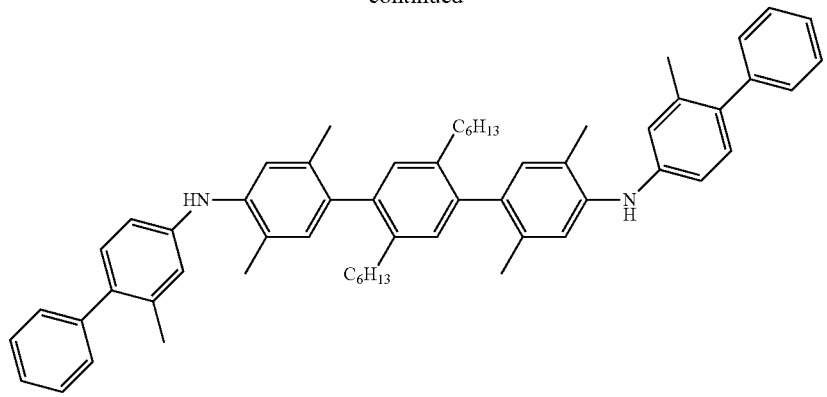

16

To the solution of diamine, 8, (1.52 g, 3.13 mmol) and 2-methyl-4-bromobiphenyl (1.55 g, 6.26 mmol) in toluene (40 mL) was added the solution of pd₂dba₃ (172 mg, 0.188 mmol) and P(t-Bu)₃ (76 mg, 0.376 mmol) in toluene (5 mL), followed by the addition of NaO^tBu (0.603 g, 6.26 mmol) under nitrogen. The resultant mixture was stirred at room temperature overnight. The mixture was filtered through a short silica bed and the filtrate was concentrated under reduced pressure. By column chromatography (0-1% ethyl acetate in hexane) 1.1 g of product, 16, was obtained as a solid (43% yield).

Synthesis Example 2

This example illustrates the synthesis of Compound A.

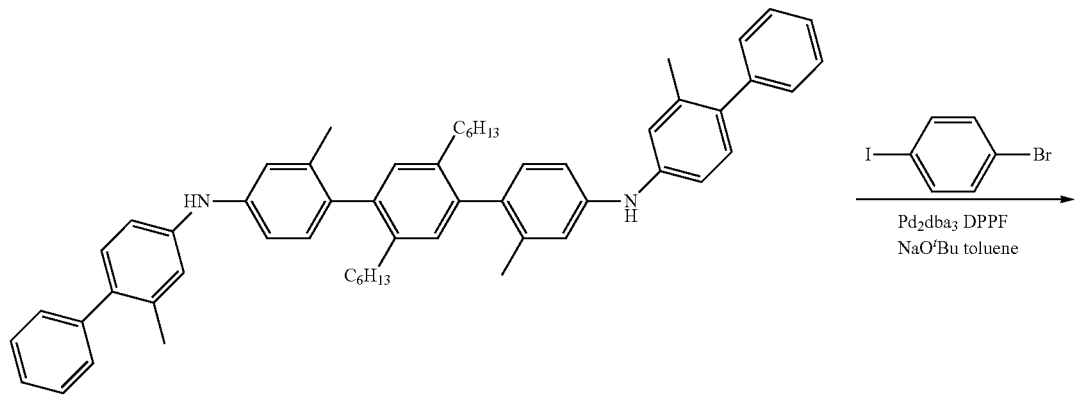

9

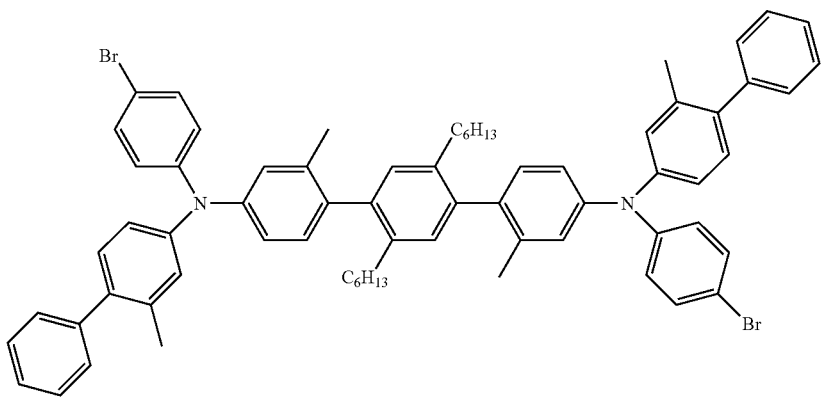

Compound A

To the solution of diamine, 9, (1.2 g, 1.52 mmol) and 1-bromo-4-iodobenzene (1.29 g, 4.56 mmol) in toluene (40 mL) was added the solution of pd$_2$ dba$_3$ (38 mg, 0.041 mmol) and DPPF (45 mg, 0.081 mmol) in toluene (5 mL), followed by the addition of NaO$^t$Bu (0.365 g, 3.80 mmol) under nitrogen. The resultant mixture was stirred at 95° C. for 16 hrs. The mixture was filtered through a short silica bed and the filtrate was concentrated under reduced pressure. By column chromatography (0-10% toluene in hexane) 1.06 g of product, Compound A, was obtained as a solid (63% yield).

The non-brominated analog of Compound A can be prepared in a similar manner by using iodobenzene in place of 1-bromo-4-iodobenzene.

Synthesis Example 3

This example illustrates the synthesis of Compound C.

To the solution of diamine, 16, (1.1 g, 1.34 mmol) and 1-bromo-4-iodobenzene (1.90 g, 6.73 mmol) in toluene (40 mL) was added the solution of pd$_2$ dba$_3$ (65 mg, 0.071 mmol) and DPPF (79 mg, 0.143 mmol) in toluene (5 mL), followed by the addition of NaO$^t$Bu (0.388 g, 4.03 mmol) under nitrogen. The resultant mixture was stirred at 105° C. for 24 hrs. The mixture was filtered through a short silica bed and the filtrate was concentrated under reduced pressure. By column chromatography (0-0.8% toluene in hexane) 1.26 g of product, Compound C, was obtained as a solid (83% yield).

The non-brominated analog of Compound C can be prepared in a similar manner by using iodobenzene in place of 1-bromo-4-iodobenzene.

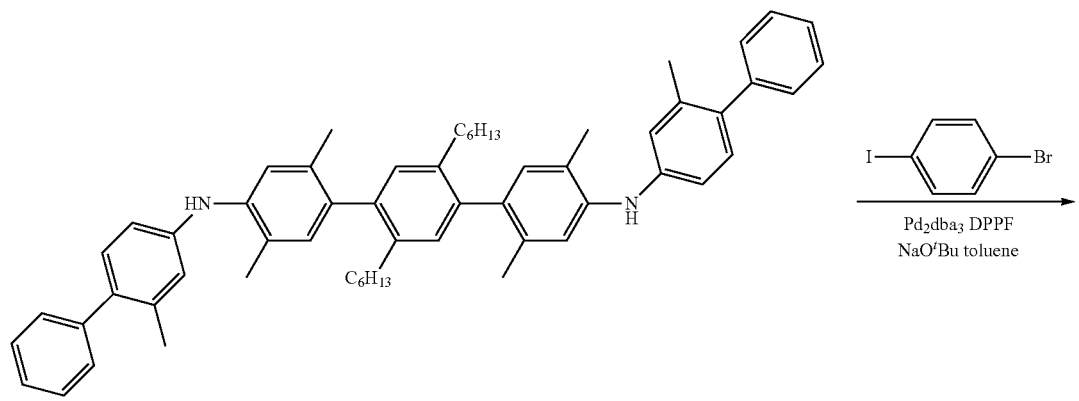

16

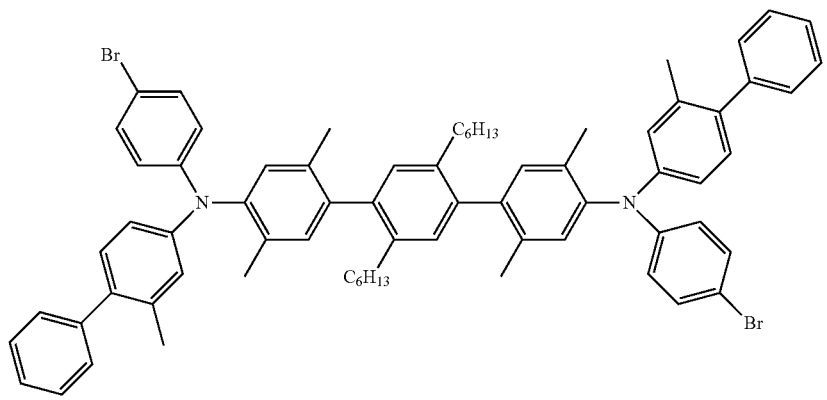

Compound C

Synthesis Example 4

This example illustrates the synthesis of Compound E.

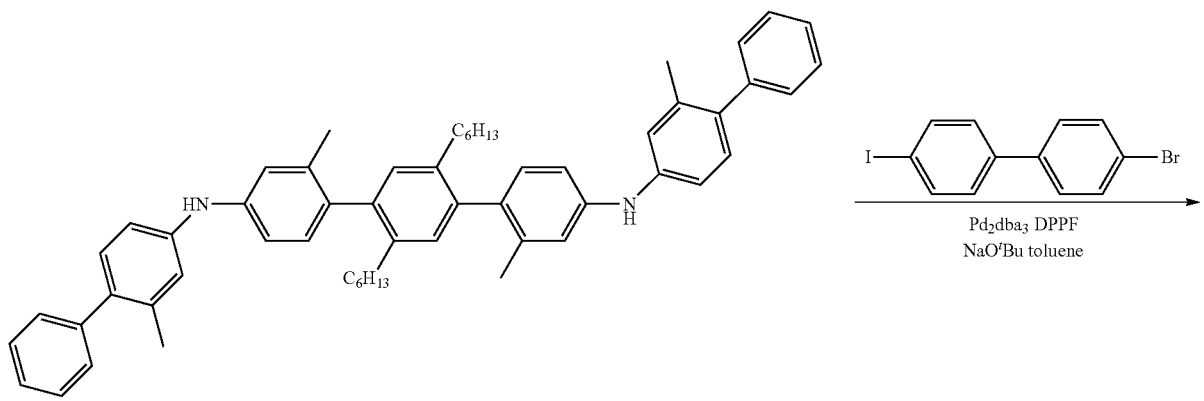

9

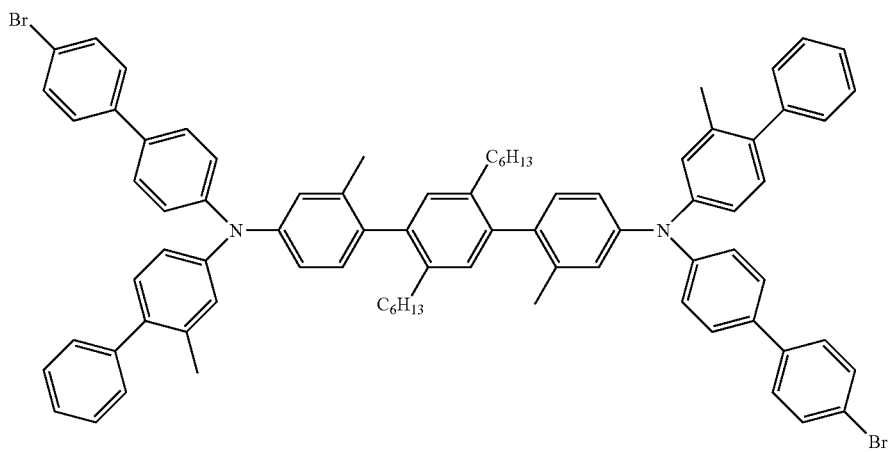

Compound E

To the solution of diamine, 9, (1.6 g, 1.77 mmol) and 4-bromo-4'-iodohiphenyl (1.91 g, 5.32 mmol) in toluene (40 mL) was added the solution of $pd_2$ $dba_3$ (44 mg, 0.048 mmol) and DPPF (52 mg, 0.094 mmol) in toluene (5 mL), followed by the addition of NaO$^t$Bu (0.426 g, 4.44 mmol) under nitrogen. The resultant mixture was stirred at 95° C. for 48 hrs. The mixture was filtered through a short silica bed and the filtrate was concentrated under reduced pressure. By column chromatography (0-10% toluene in hexane) 1.55 g of product, Compound E, was obtained as a solid (70% yield).

The non-brominated analog of Compound E can be prepared in a similar manner by using 4-iodobiphenyl in place of 4-bromo-4'-iodobiphenyl.

Synthesis Example 5

This example illustrates the preparation of some additional intermediate materials.

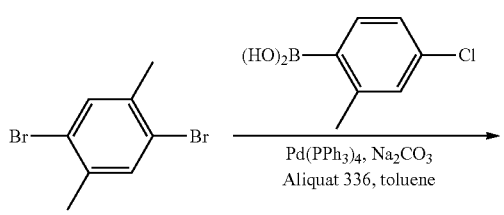

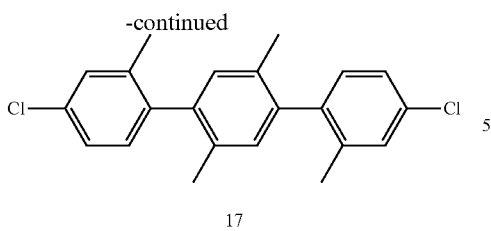

17

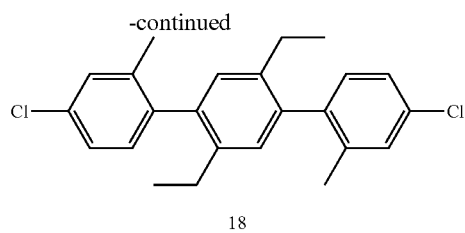

18

In the glove box the mixture of 2,5-dibromo-p-xylene (5.64 g, 21.36 mmol), 4-chloro-2-methylphenylboronic acid (7.28 g, 42.73 mmol), Aliquat 336 (0.45 g), and Pd(PPh$_3$)$_4$ (1.234 g, 1.068 mmol, 0.05 eq), and Na$_2$CO$_3$ (11.32 g, 106.8 mmol) in degassed toluene (200 mL) was prepared. Outside dry box, the degassed water (60 mL) was added to the former mixture under nitrogen, and then the resultant mixture was stirred at 88° C. overnight under nitrogen. The organic layer was separated and the aqueous layer was extracted with ethyl acetate. The combined organic layers were dried over anhydrous MgSO$_4$. Filtration, concentration of the filtrate, and then the silica column chromatography (hexane) provided the desired product, 17, (6.5 g, 85% yield) as a white solid.

In the glove box the mixture of 1,4-dibromo-2,5-diethylbenzene (7.11 g, 24.35 mmol), 4-chloro-2-methylphenylboronic acid (8.3 g, 48.70 mmol), Aliquat 336 (0.5 g), and Pd(PPh$_3$)$_4$ (1.4 g, 1.21 mmol, 0.05 eq), and Na$_2$CO$_3$ (12.9 g, 121.7 mmol) in degassed toluene (200 mL) was prepared. Outside dry box, the degassed water (65 mL) was added to the former mixture under nitrogen, and then the resultant mixture was stirred at 88° C. overnight under nitrogen. The organic layer was separated and the aqueous layer was extracted with ethyl acetate. The combined organic layers were dried over anhydrous MgSO$_4$. Filtration, concentration of the filtrate, and then the silica column chromatography (hexane) provided the desired product, 18, (6.7 g, 72% yield) as a white solid.

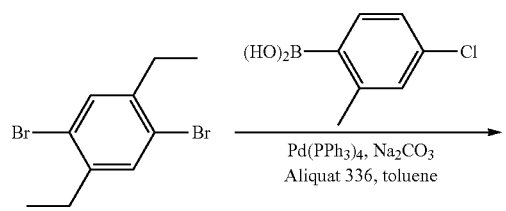

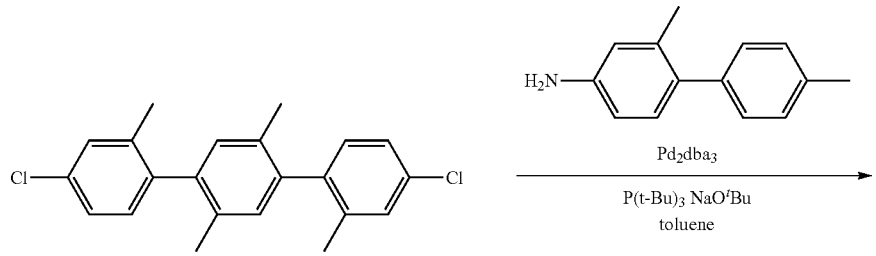

17

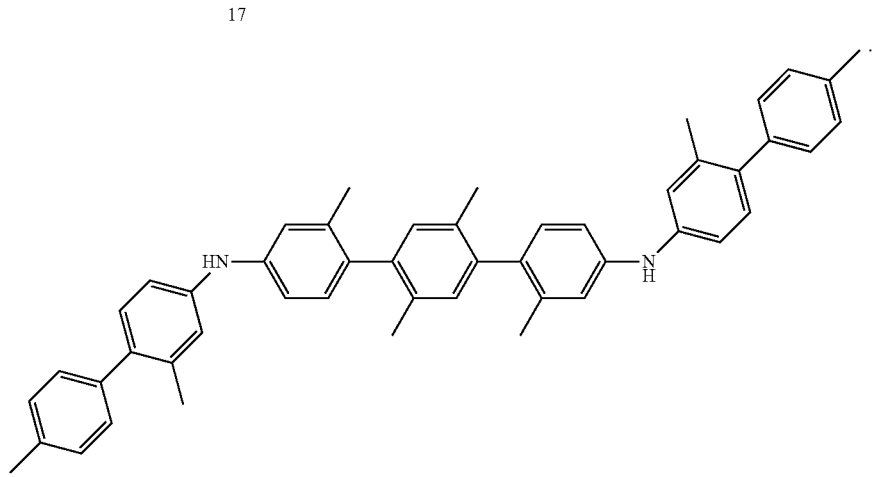

19

To the solution of dichloroterphenyl, 17, (2.0 g, 5.63 mmol) and 2,4-dimethyl-biphenyl-4-ylamine (2.22 g, 11.25 mmol) in toluene (50 mL) was added the solution of pd₂dba₃ (309 mg, 0.338 mmol) and P(t-Bu)₃ (137 mg, 0.675 mmol) in toluene (10 mL), followed by the addition of NaO$^t$Bu (1.35 g, 14.07 mmol) under nitrogen. The resultant mixture was stirred at 80° C. for 6 hrs. The mixture was filtered through a short silica bed and the filtrate was concentrated under reduced pressure. By column chromatography (10-45% DCM in hexane) 2.91 g of product, 19, was obtained as a solid (77% yield).

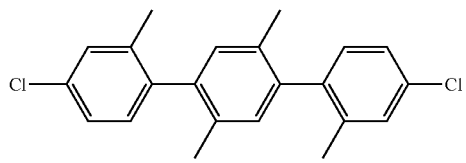

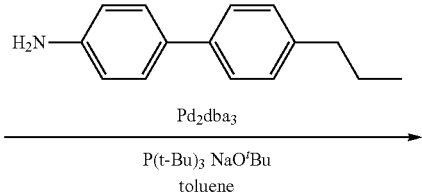

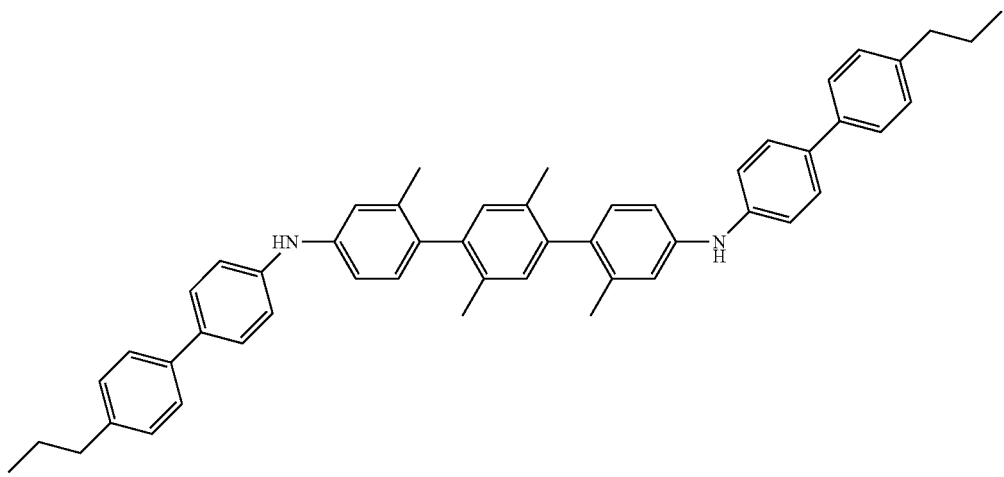

To the solution of dichloroterphenyl, 17, (2.0 g, 5.63 mmol) and 4-amino-4'-propyl-biphenyl (2.38 g, 11.25 mmol) in toluene (50 mL) was added the solution of pd₂dba₃ (309 mg, 0.338 mmol) and P(t-Bu)₃ (137 mg, 0.675 mmol) in toluene (10 mL), followed by the addition of NaO$^t$Bu (1.35 g, 14.07 mmol) under nitrogen. The resultant mixture was stirred at 80° C. for 6 hrs. The mixture was filtered through a short silica bed and the filtrate was concentrated under reduced pressure. By column chromatography (10-45% DCM in hexane) 2.4 g of product, 20, was obtained as a solid (60% yield).

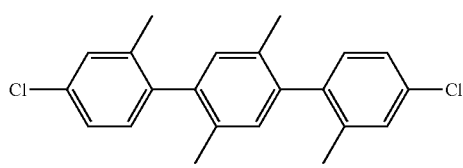

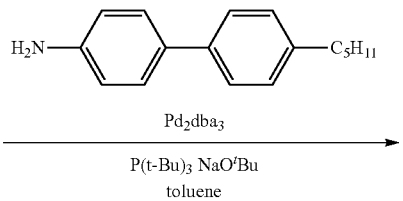

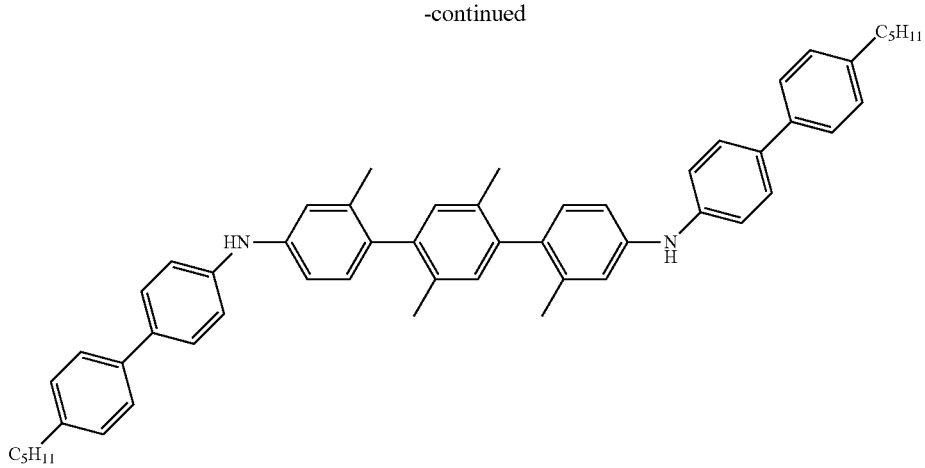

21

To the solution of dichloroterphenyl, 17, (2.6 g, 7.32 mmol) and 4-amino-4'-pentyl-biphenyl (3.50 g, 14.64 mmol) in toluene (45 mL) was added the solution of $pd_2 dba_3$ (402 mg, 0.439 mmol) and $P(t-Bu)_3$ (178 mg, 0.878 mmol) in toluene (10 mL), followed by the addition of NaO$^t$Bu (1.76 g, 18.29 mmol) under nitrogen. The resultant mixture was stirred at 80° C. for 4 hrs. The mixture was filtered through a short silica bed and the filtrate was concentrated under reduced pressure. By column chromatography (10-45% DCM in hexane) 4 g of product, 21, was obtained as a solid (72% yield).

To the solution of dichloroterphenyl, 17, (2.6 g, 7.32 mmol) and 2-methyl-4'-propyl-biphenyl-4-ylamine (3.3 g, 14.64 mmol) in toluene (50 mL) was added the solution of $pd_2 dba_3$ (402 mg, 0.439 mmol) and $P(t-Bu)_3$ (178 mg, 0.878 mmol) in toluene (5 mL), followed by the addition of NaO$^t$Bu (1.76 g, 18.29 mmol) under nitrogen. The resultant mixture was stirred at 80° C. for 4.5 hrs. The mixture was filtered through a short silica bed and the filtrate was concentrated under reduced pressure. By column chromatography (10-45% DCM in hexane) 4.11 g of product, 22, was obtained as a solid (77% yield).

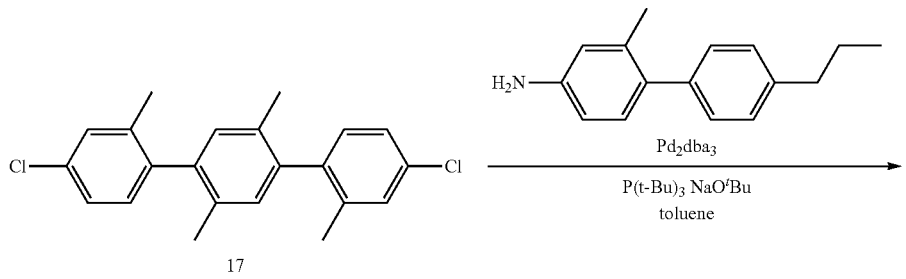

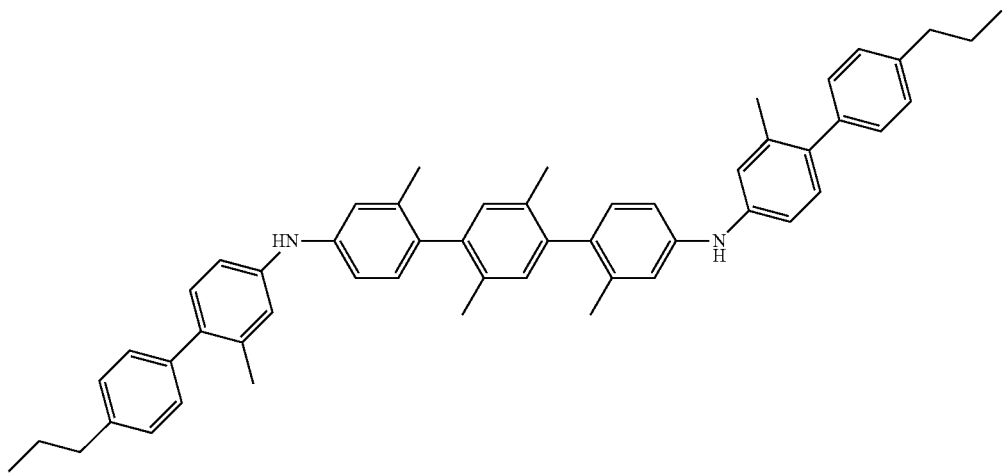

22

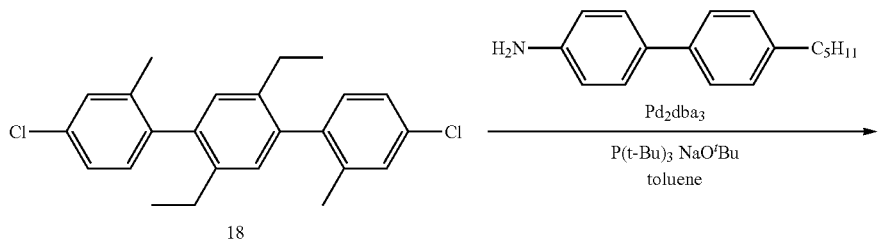

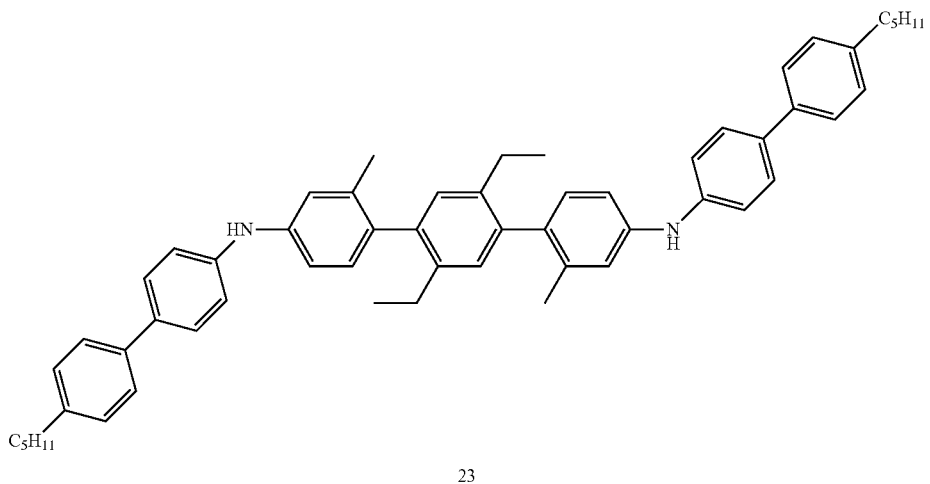

To the solution of dichloroterphenyl, 18, (1.61 g, 4.2 mmol) and 4-amino-4'-pentyl-biphenyl (2.0 g, 8.4 mmol) in toluene (35 mL) was added the solution of pd$_2$ dba$_3$ (229 mg, 0.252 mmol) and P(t-Bu)$_3$ (101 mg, 0.504 mmol) in toluene (10 mL), followed by the addition of NaO$^t$Bu (1.0 g, 10.5 mmol) under nitrogen. The resultant mixture was stirred at 80° C. for 4 hrs. The mixture was filtered through a short silica bed and the filtrate was concentrated under reduced pressure. By column chromatography (10-45% DCM in hexane) 3 g of product, 23, was obtained as a solid (91% yield).

Synthesis Example 6

This example illustrates the synthesis of Compound F.

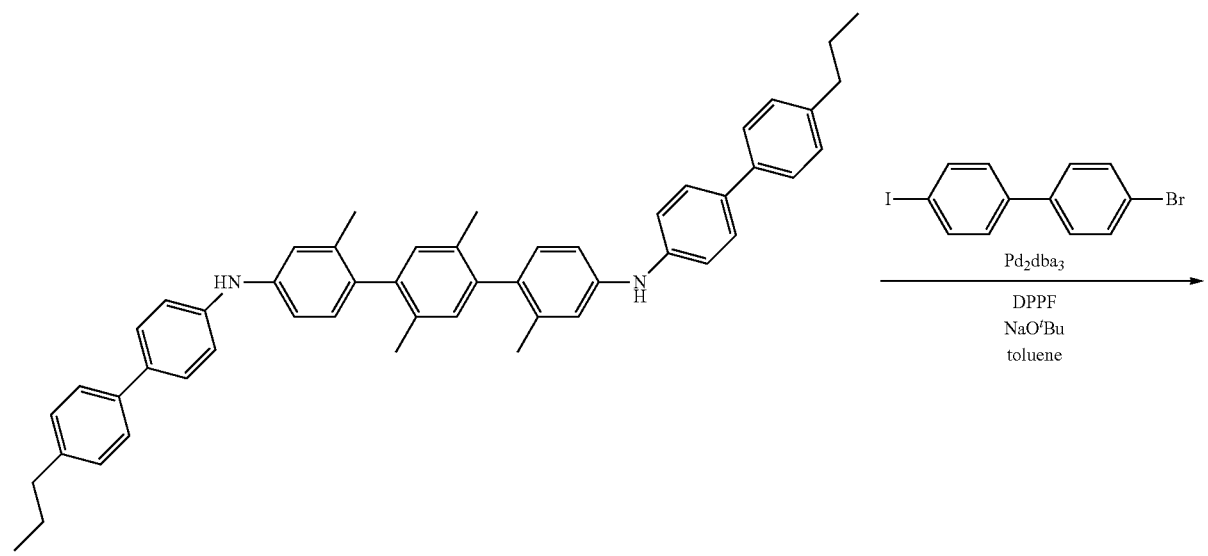

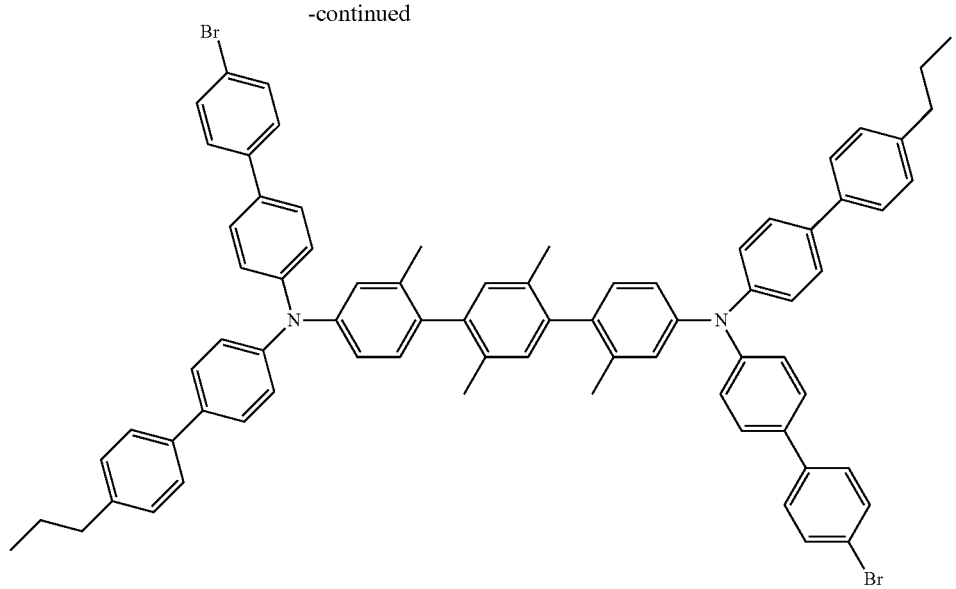

Compound F

To the solution of diamine, 20, (1.18 g, 1.67 mmol) and 4-bromo-4'-iodobiphenyl (1.80 g, 5.02 mmol) in toluene (30 mL) was added the solution of pd$_2$ dba$_3$ (92 mg, 0.1 mmol) and DPPF (112 mg, 0.2 mmol) in toluene (10 mL), followed by the addition of NaO$^t$Bu (0.354 g, 3.67 mmol) under nitrogen. The resultant mixture was stirred at 95° C. for 17 hrs. The mixture was filtered through a short silica bed and the filtrate was concentrated under reduced pressure. By column chromatography (10-20% toluene in hexane) 1.7 g of product, Compound F, was obtained as a solid (87% yield).

The non-brominated analog of Compound F can be prepared in a similar manner by using 4-iodobiphenyl in place of 4-bromo-4'-iodobiphenyl.

Synthesis Example 7

This example illustrates the synthesis of Compound G.

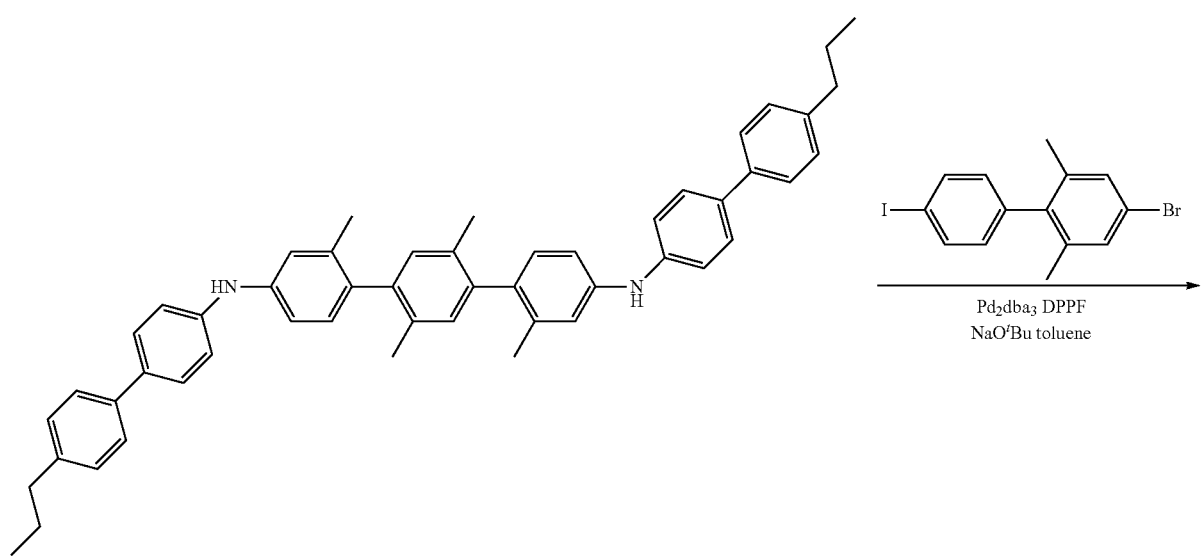

-continued

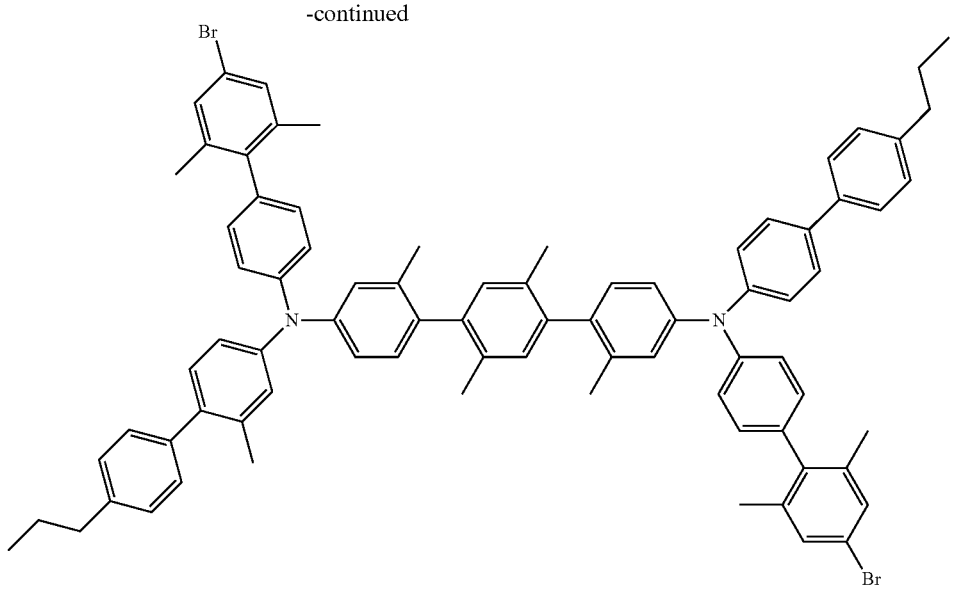

Compound G

To the solution of diamine, 20, (1.18 g, 1.67 mmol) and 4-bromo-4'-iodo-2,6-dimethylbiphenyl (1.94 g, 5.02 mmol) in toluene (30 mL) was added the solution of $pd_2$ $dba_3$ (92 mg, 0.1 mmol) and DPPF (112 mg, 0.2 mmol) in toluene (10 mL), followed by the addition of $NaO^tBu$ (0.354 g, 3.67 mmol) under nitrogen. The resultant mixture was stirred at 95° C. for 17 hrs. The mixture was filtered through a short silica bed and the filtrate was concentrated under reduced pressure. By column chromatography (10-20% toluene in hexane) 1.6 g of product, Compound G, was obtained as a solid (79% yield).

The non-brominated analog of Compound G can be prepared in a similar manner by using 2,6-dimethyl-4"-iodobiphenyl in place of 2,6-dimethyl-4-bromo-4'-iodobiphenyl.

Synthesis Example 8

This example illustrates the synthesis of Compound H.

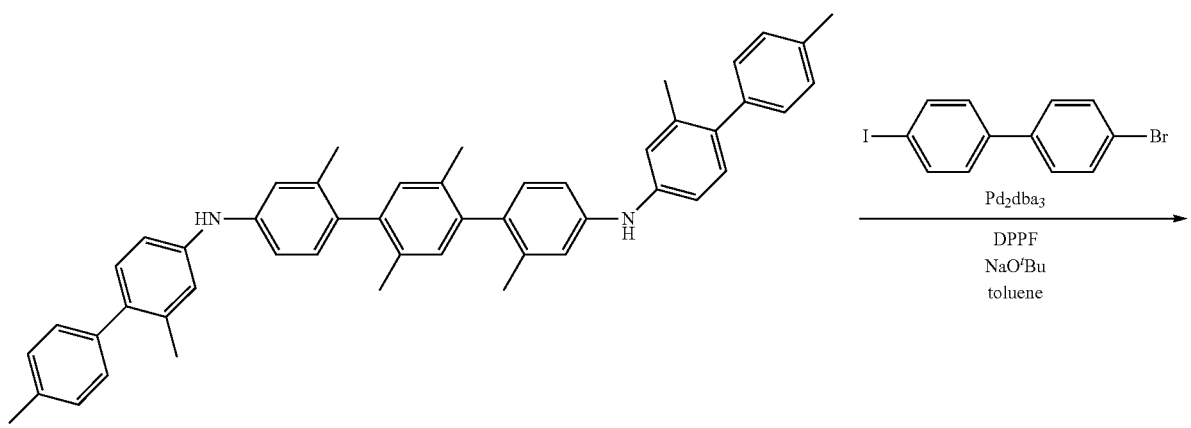

-continued

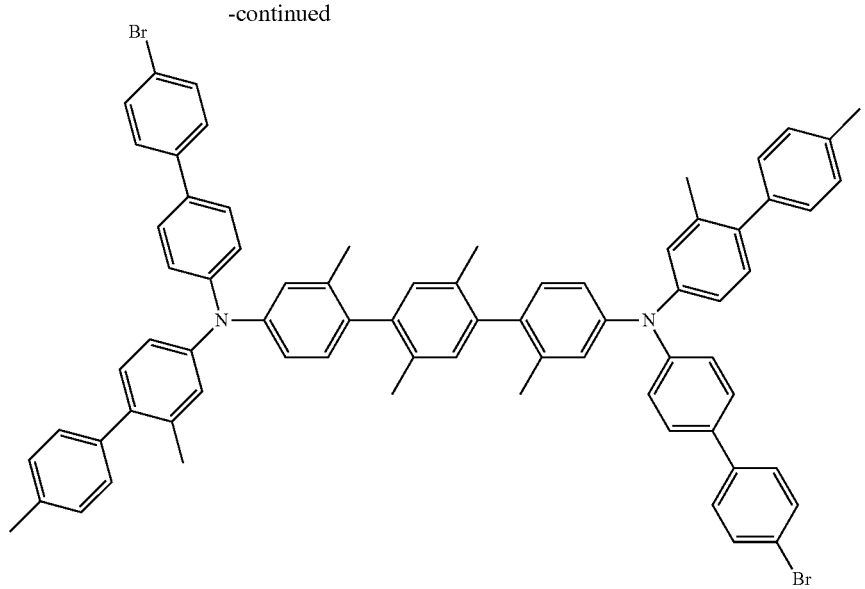

Compound H

To the solution of diamine, 19, (1.3 g, 1.92 mmol) and 4-bromo-4'-iodobiphenyl (2.06 g, 5.76 mmol) in dioxane (40 mL) was added the solution of pd$_2$ dba$_3$ (47 mg, 0.051 mmol) and DPPF (56 mg, 0.102 mmol) in dioxane (10 mL), followed by the addition of NaO$^t$Bu (0.461 g, 4.801 mmol) under nitrogen. The resultant mixture was stirred at 95° C. for 16 hrs. The mixture was filtered through a short silica bed and the filtrate was concentrated under reduced pressure. By column chromatography (3-11% toluene in hexane) 1.0 g of product, Compound H, was obtained as a solid (46% yield).

The non-brominated analog of Compound H can be prepared in a similar manner by using 4-iodobiphenyl in place of 4-bromo-4'-iodobiphenyl.

Synthesis Example 9

This example illustrates the synthesis of Compound I.

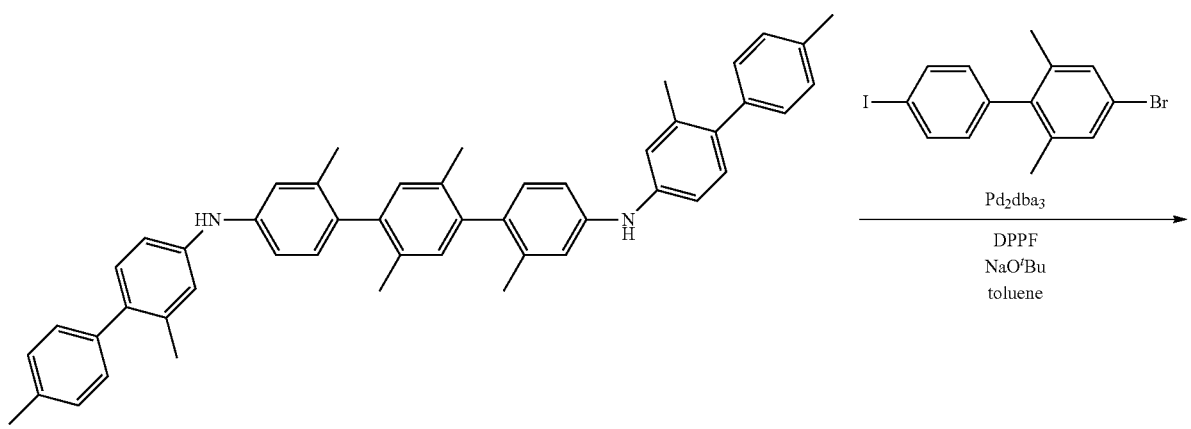

-continued

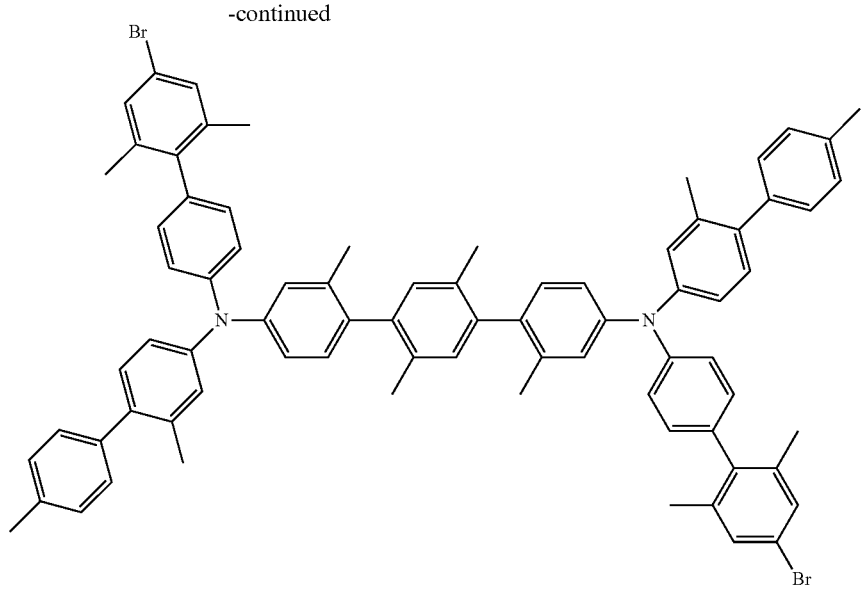

Compound I

To the solution of diamine, 19, (1.2 g, 1.77 mmol) and 4-bromo-4'-iodo-2,6-dimethylbiphenyl (2.06 g, 5.32 mmol) in toluene (40 mL) was added the solution of $pd_2\,dba_3$ (44 mg, 0.048 mmol) and DPPF (52 mg, 0.094 mmol) in toluene (5 mL), followed by the addition of NaO$^t$Bu (0.426 g, 4.432 mmol) under nitrogen. The resultant mixture was stirred at 95° C. for 16 hrs. The mixture was filtered through a short silica bed and the filtrate was concentrated under reduced pressure. By column chromatography (3-20% toluene in hexane) 0.867 g of product, Compound I, was obtained as a solid (41% yield).

The non-brominated analog of Compound I can be prepared in a similar manner by using 2,6-dimethyl-4''-iodobiphenyl in place of 2,6-dimethyl-4-bromo-4'-iodobiphenyl.

Synthesis Example 10

This example illustrates the synthesis of Compound J.

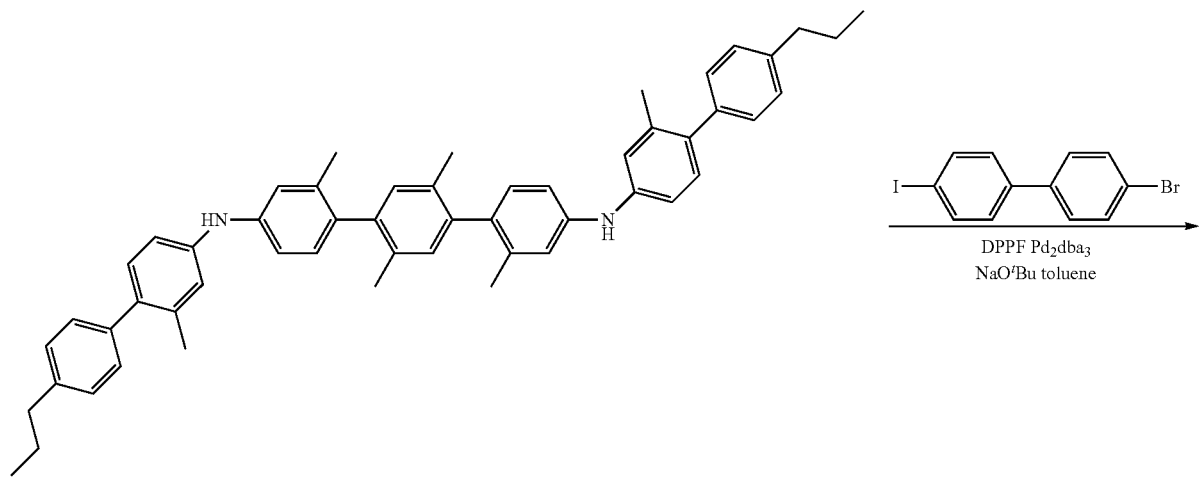

-continued

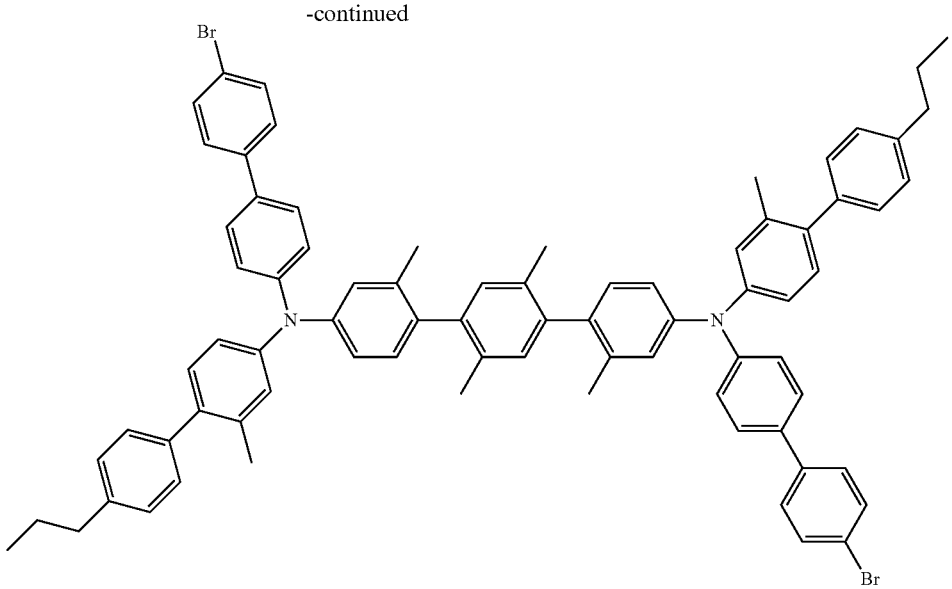

Compound J

To the solution of diamine, 22, (2.1 g, 2.86 mmol) and 4-bromo-4'-iodobiphenyl (3.08 g, 8.6 mmol) in toluene (60 mL) was added the solution of pd$_2$dba$_3$ (71 mg, 0.077 mmol) and DPPF (84 mg, 0.152 mmol) in toluene (10 mL), followed by the addition of NaO$^t$Bu (0,688 g, 7.16 mmol) under nitrogen. The resultant mixture was stirred at 95° C. for 16 hrs. The mixture was filtered through a short silica bed and the filtrate was concentrated under reduced pressure. By column chromatography (5-20% toluene in hexane) 1.33 g of product, Compound J, was obtained as a solid (39% yield).

The non-brominated analog of Compound J can be prepared in a similar manner by using 4-iodobiphenyl in place of 4-bromo-4'-iodobiphenyl.

Synthesis Example 11

This example illustrates the synthesis of Compound K.

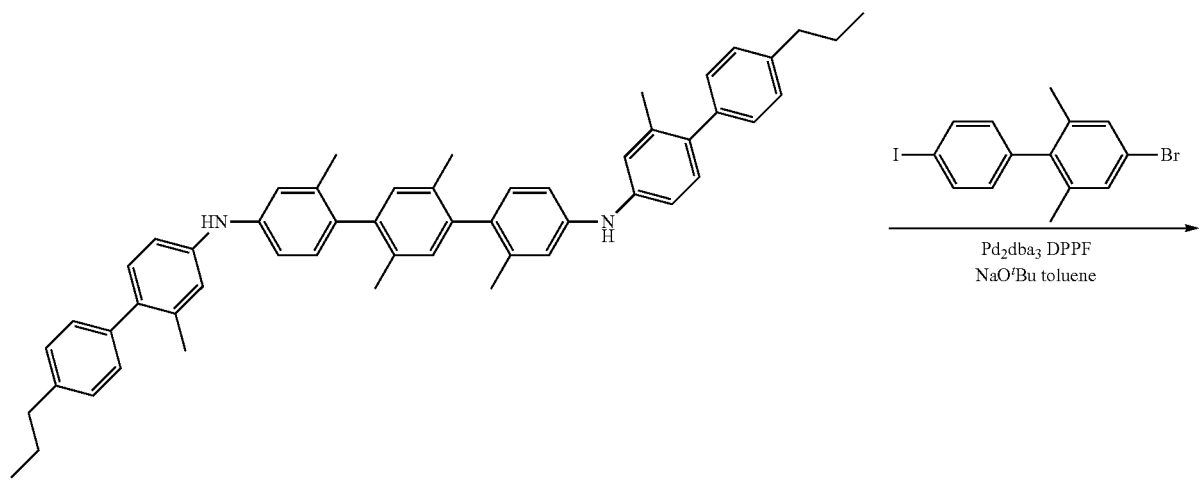

-continued

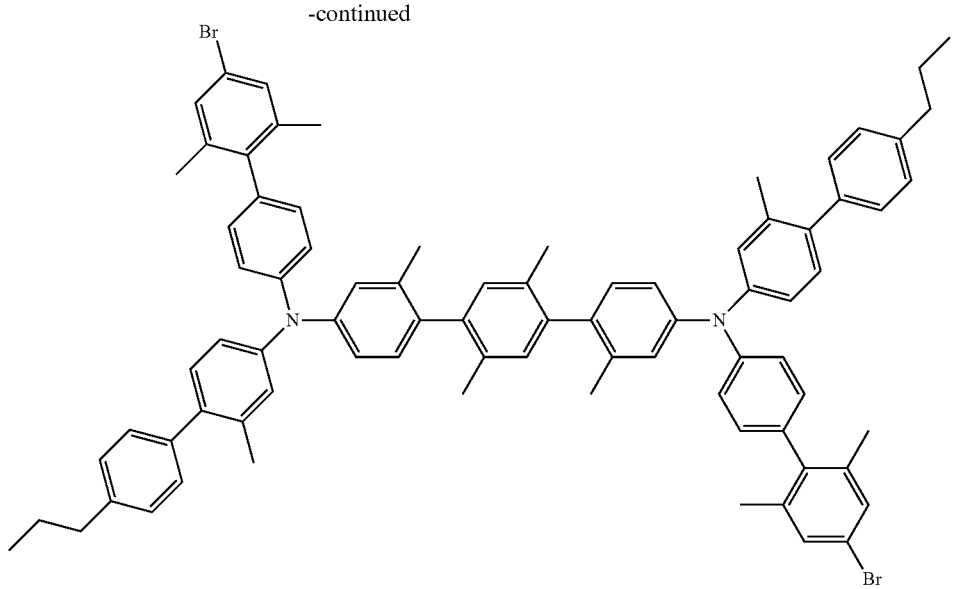

Compound K

To the solution of diamine, 22, (2.0 g, 2.73 mmol) and 4-bromo-4'-iodo-2,6-dimethylbiphenyl (3.17 g, 8.18 mmol) in toluene (50 mL) was added the solution of pd$_2$ dba$_3$ (67 mg, 0.074 mmol) and DPPF (80 mg, 0.145 mmol) in toluene (10 mL), followed by the addition of NaO$^t$Bu (0.655 g, 6.821 mmol) under nitrogen. The resultant mixture was stirred at 95° C. for 16 hrs. The mixture was filtered through a short silica bed and the filtrate was concentrated under reduced pressure. By column chromatography (5-18% toluene in hexane) 0.95 g of product, Compound K, was obtained as a solid (28% yield).

The non-brominated analog of Compound K can be prepared in a similar manner by using 2,6-dimethyl-4'-iodobiphenyl in place of 2,6-dimethyl-4-bromo-4'-iodobiphenyl.

Synthesis Example 12

This example illustrates the synthesis of Compound L.

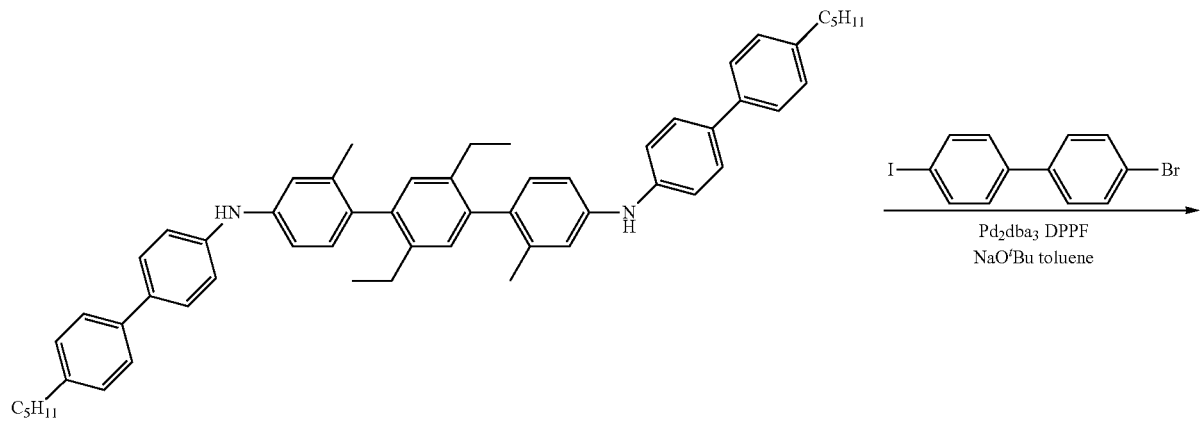

-continued

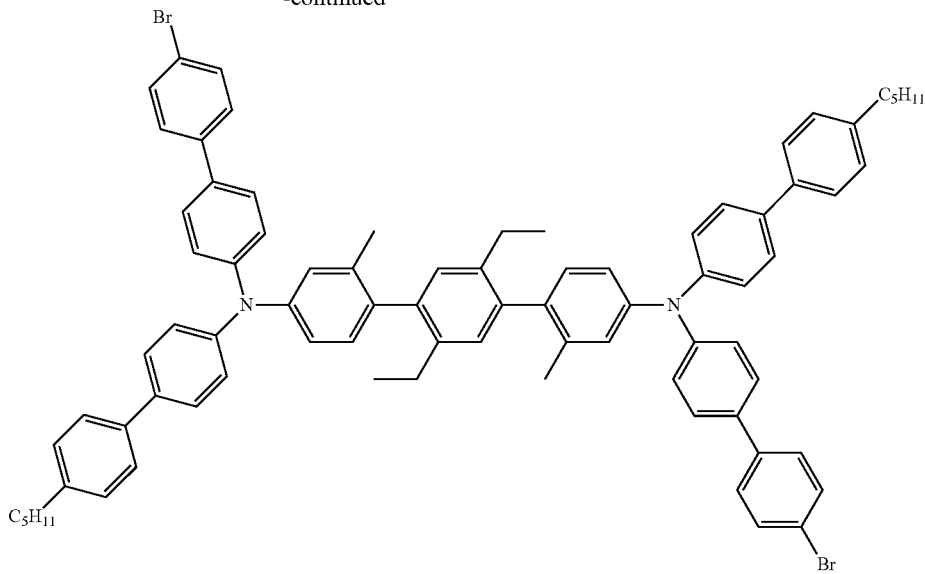

Compound L

To the solution of diamine, 23, (1.45 g, 1.84 mmol) and 4-bromo-4'-iodobiphenyl (1.97 g, 5.51 mmol) in toluene (30 mL) was added the solution of pd$_2$dba$_3$ (100 mg, 0.110 mmol) and DPPF (122 mg, 0.220 mmol) in toluene (10 mL), followed by the addition of NaO$^t$Bu (0.388 g, 4.04 mmol) under nitrogen. The resultant mixture was stirred at 95° C. for 18 hrs. The mixture was filtered through a short silica bed and the filtrate was concentrated under reduced pressure. By column chromatography (3-11% DCM in hexane) 1.52 g of product, Compound L, was obtained as a solid (65% yield).

The non-brominated analog of Compound L can be prepared in a similar manner by using 4-iodobiphenyl in place of 4-bromo-4'-iodobiphenyl.

Synthesis Example 13

This example illustrates the synthesis of Compound M.

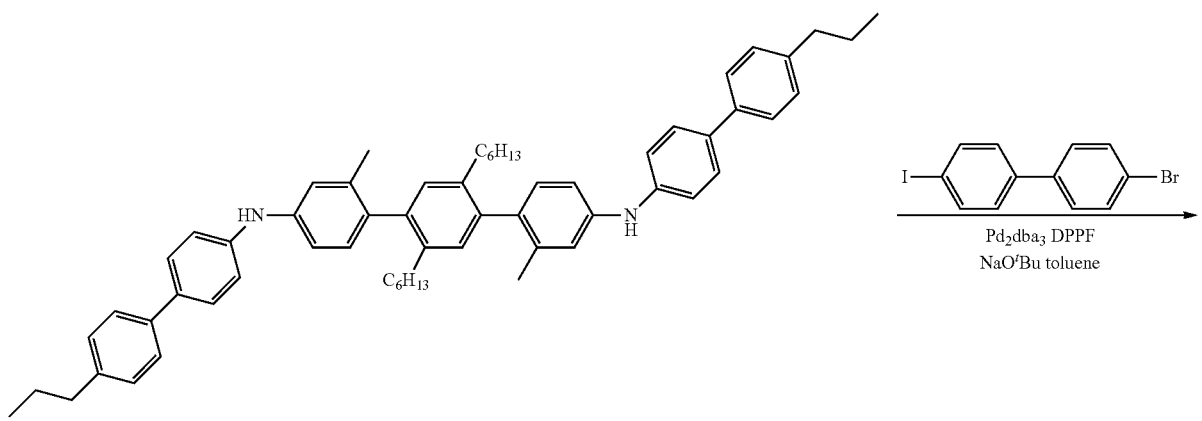

-continued

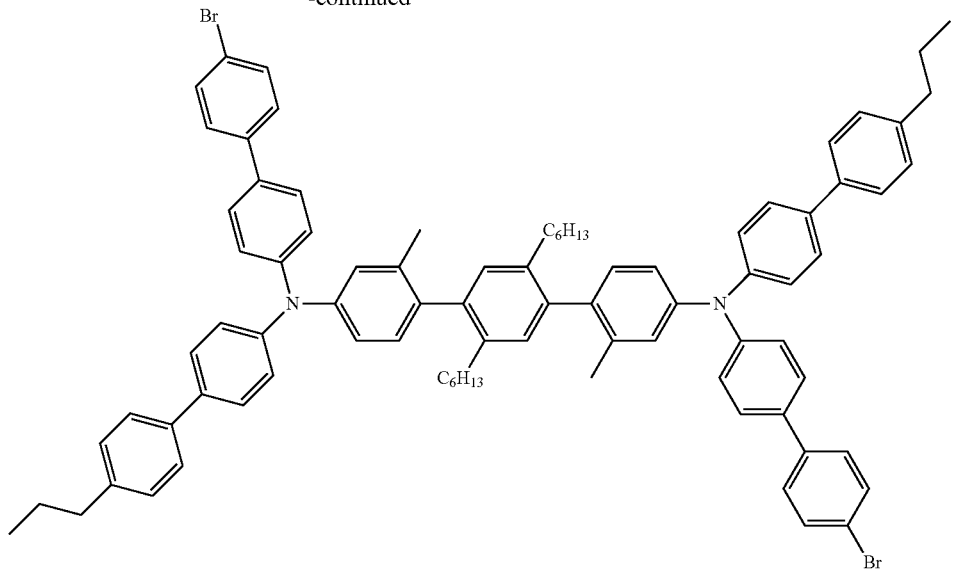

Compound M

To the solution of diamine, 10, (1.25 g, 1.48 mmol) and 4-bromo-4'-iodobiphenyl (1.59 g, 4.44 mmol) in toluene (30 mL) was added the solution of pd$_2$ dba$_3$ (37 mg, 0.04 mmol) and DPPF (43 mg, 0.078 mmol) in toluene (10 mL), followed by the addition of NaO$^t$Bu (0.355 g, 3.70 mmol) under nitrogen. The resultant mixture was stirred at 95° C. for 16 hrs. The mixture was filtered through a short silica bed and the filtrate was concentrated under reduced pressure. By column chromatography (0-12% toluene in hexane) 1.10 g of product, Compound M, was obtained as a solid (57% yield).

The non-brominated analog of Compound M can be prepared in a similar manner by using 4-iodobiphenyl in place of 4-bromo-4'-iodobiphenyl.

Synthesis Example 14

This example illustrates the synthesis of Compound NL.

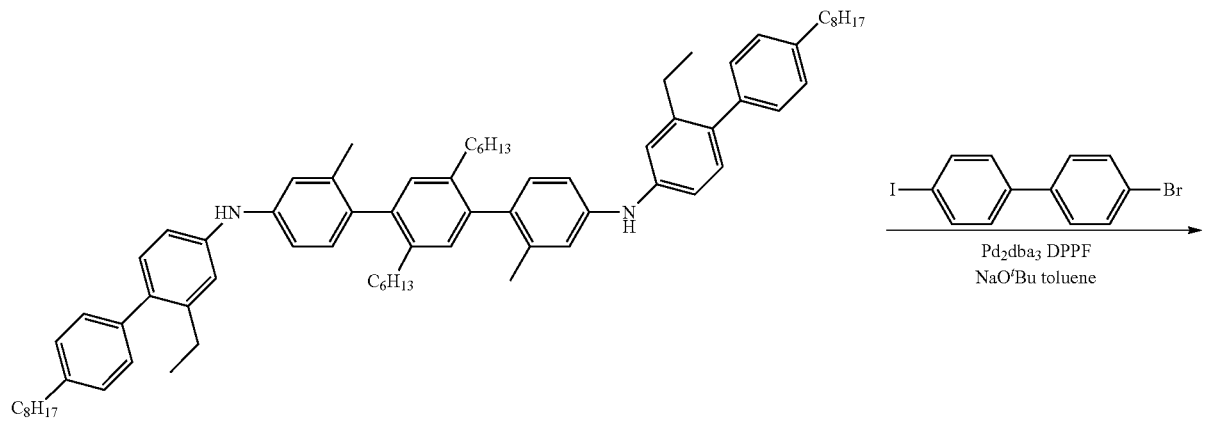

-continued

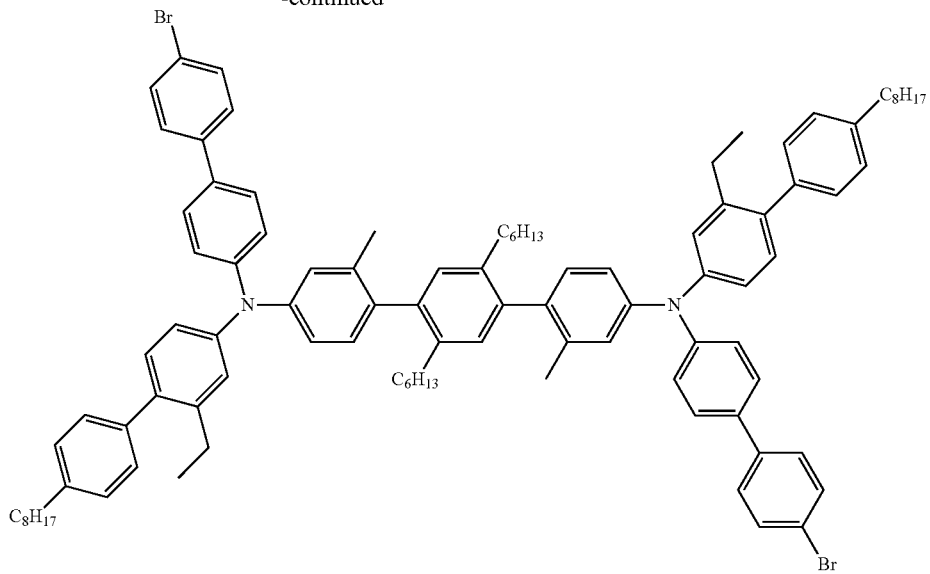

Compound N

To the solution of diamine, 11, (1.42 g, 1.36 mmol) and 4-bromo-4'-iodobiphenyl (1.47 g, 4.09 mmol) in toluene (30 mL) was added the solution of $pd_2\ dba_3$ (34 mg, 0.037 mmol) and DPPF (40 mg, 0.072 mmol) in toluene (10 mL), followed by the addition of NaO$^t$Bu (0.328 g, 3.41 mmol) under nitrogen. The resultant mixture was stirred at 95° C. for 16 hrs. The mixture was filtered through a short silica bed and the filtrate was concentrated under reduced pressure. By column chromatography (0-12% toluene in hexane) 1.33 g of product, Compound N, was obtained as a solid (60% yield).

The non-brominated analog of Compound N can be prepared in a similar manner by using 4-iodobiphenyl in place of 4-bromo-4'-iodobiphenyl.

Synthesis Example 15

This example illustrates the synthesis of Compound O.

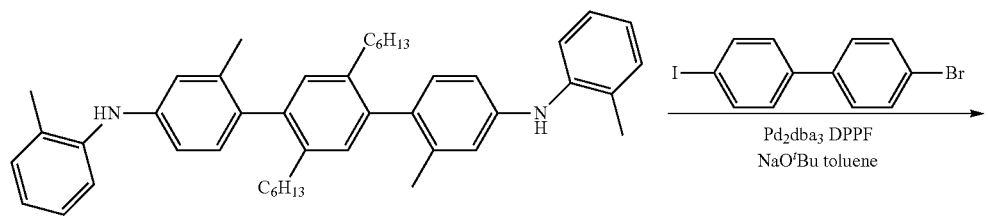

12

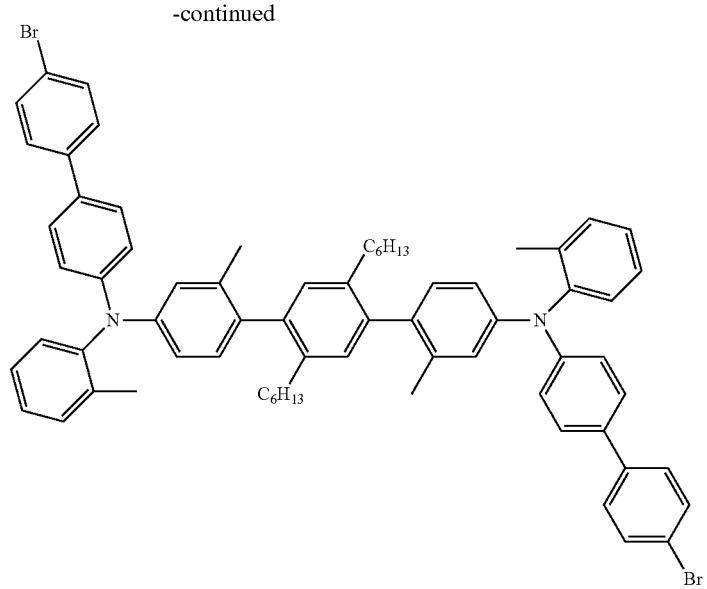

Compound O

To the solution of diamine, 12, (1.5 g, 2.35 mmol) and 4-bromo-4'-iodobiphenyl (2.53 g, 7.06 mmol) in toluene (30 mL) was added the solution of pd$_2$ dba$_3$ (174 mg, 0.191 mmol) and DPPF (211 mg, 0.38 mmol) in toluene (10 mL), followed by the addition of NaO$^t$Bu (0.565 g, 5.88 mmol) under nitrogen. The resultant mixture was stirred at 95° C. for 18 hrs. The mixture was filtered through a short silica bed and the filtrate was concentrated under reduced pressure. By column chromatography (5-10% toluene in hexane) 2.4 g of product, Compound O, was obtained as a solid (93% yield).

The non-brominated analog of Compound O can be prepared in a similar manner by using 4-iodobiphenyl in place of 4-bromo-4'-iodobiphenyl.

Synthesis Example 16

This example illustrates the synthesis of Compound P.

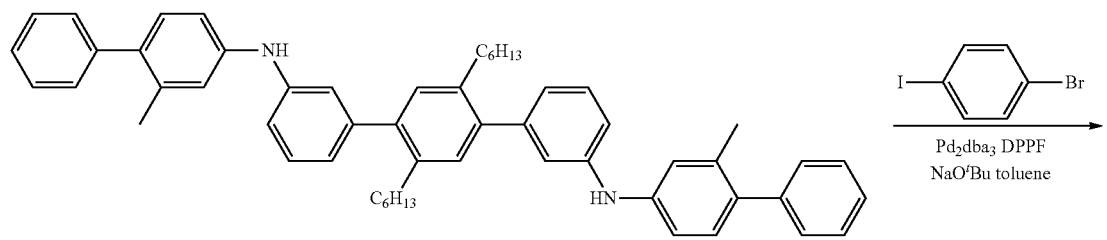

15

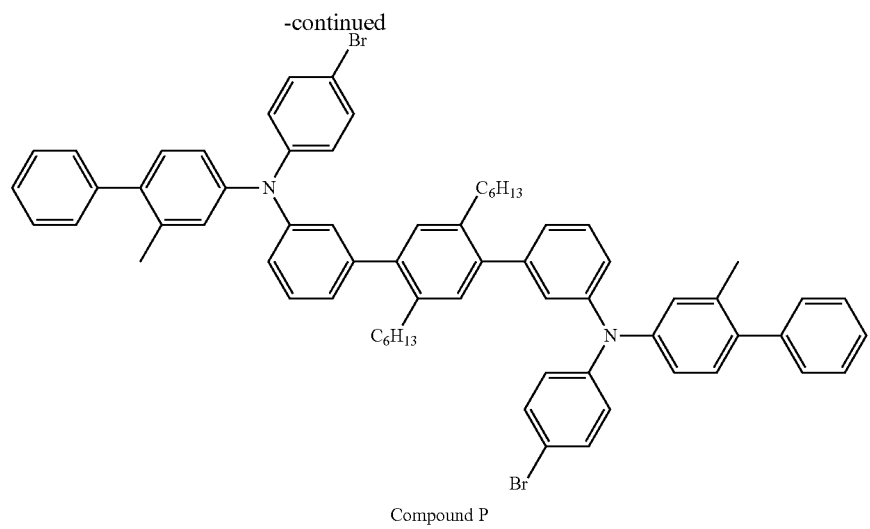

Compound P

To the solution of diamine, 15, (1.39 g, 1.826 mmol) and 1-bromo-4-iodobenzene (1.55 g, 5.48 mmol) in toluene (30 mL) was added the solution of pd$_2$ dba$_3$ (45 mg, 0.049 mmol) and DPPF (54 mg, 0.097 mmol) in toluene (10 mL), followed by the addition of NaO$^t$Bu (0.439 g, 4.56 mmol) under nitrogen. The resultant mixture was stirred at 95° C. for 16 hrs. The mixture was filtered through a short silica bed and the filtrate was concentrated under reduced pressure. By column chromatography (0-3% toluene in hexane) 1.53 g of product, Compound P, was obtained as a solid (78% yield).

The non-brominated analog of Compound P can be prepared in a similar manner by using iodobenzene in place of 1-bromo-4-iodobenzene.

Synthesis Example 17

This example illustrates the synthesis of Compound Q.

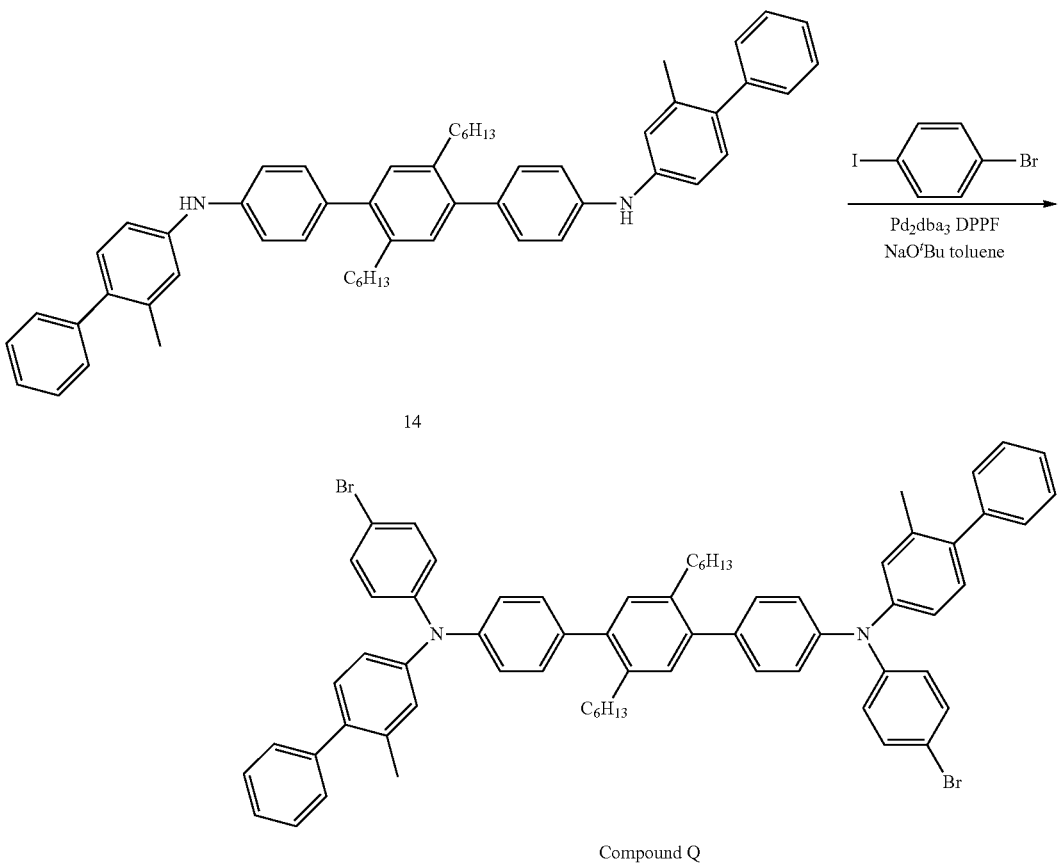

Compound Q

To the solution of diamine, 14, (1.5 g, 1.97 mmol) and 1-bromo-4-iodobenzene (1.67 g, 5.91 mmol) in toluene (30 mL) was added the solution of pd₂ dba₃ (49 mg, 0.053 mmol) and DPPF (58 mg, 0.104 mmol) in toluene (10 mL), followed by the addition of NaO$^t$Bu (0.473 g, 4.93 mmol) under nitrogen. The resultant mixture was stirred at 95° C. for 16 hrs. The mixture was filtered through a short silica bed and the filtrate was concentrated under reduced pressure. By column chromatography (0-10% toluene in hexane) 1.30 g of product, Compound Q, was obtained as a solid (62% yield).

The non-brominated analog of Compound Q can be prepared in a similar manner by using iodobenzene in place of 1-bromo-4-iodobenzene.

Synthesis Example 18

This example illustrates the synthesis of Compound R.

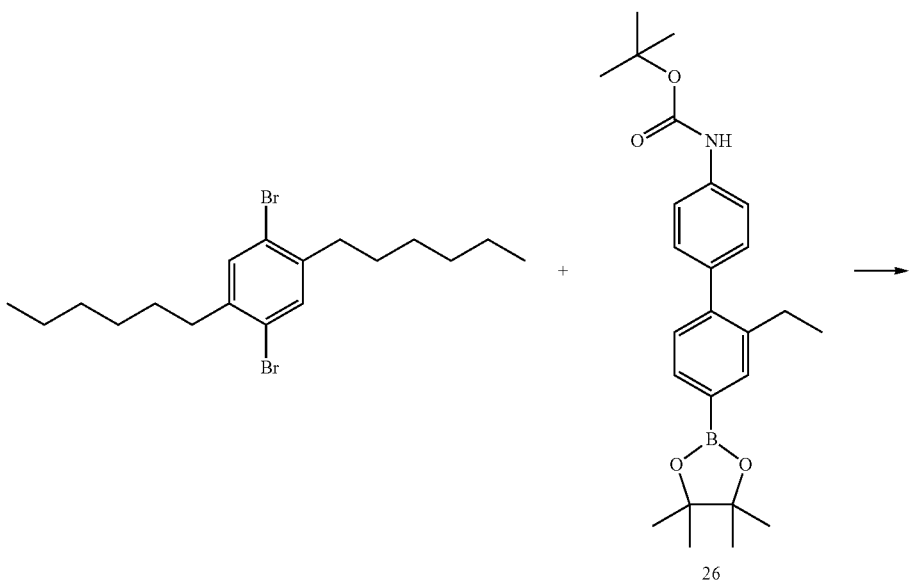

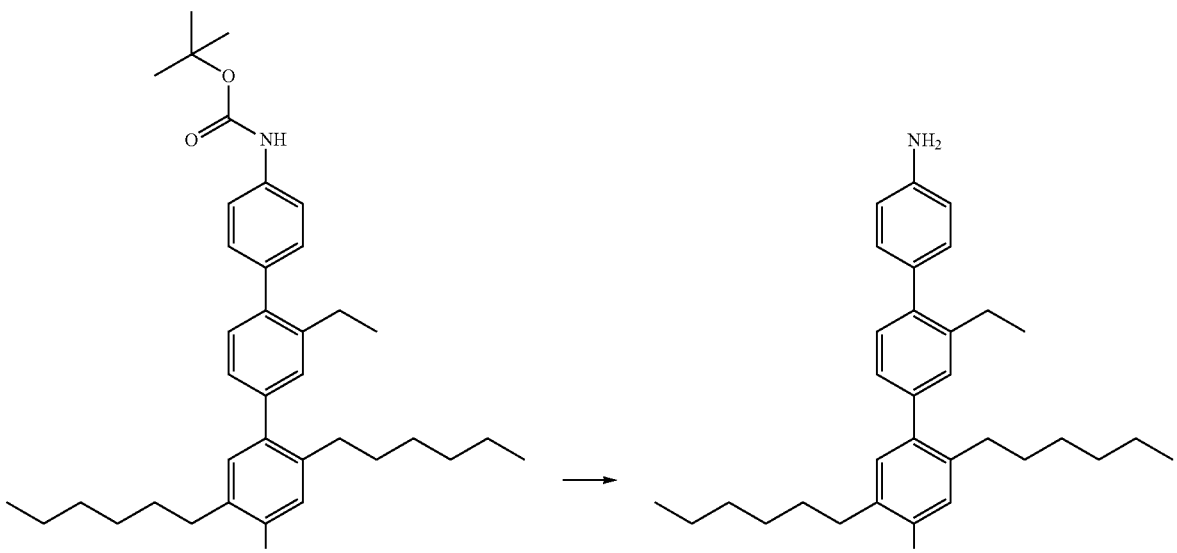

91                                                                                              92

-continued

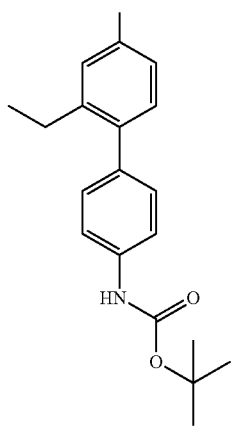

27

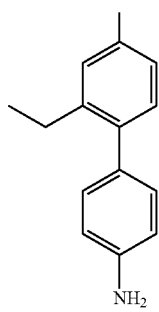

28

Compound R ←

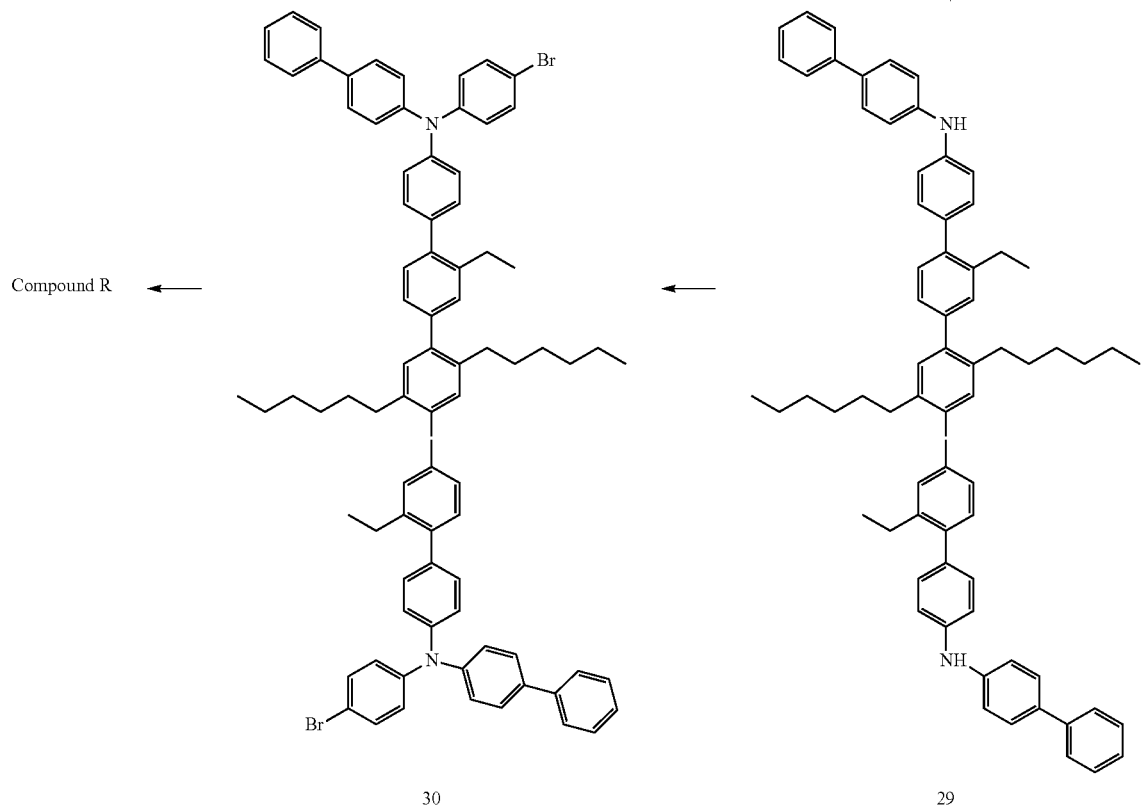

30                                                                                                  29

1,4-dibromo-2,5-dihexyl benzene (8.05 mmoles, 3.255 g), boronic ester 26 (17.7 mmoles, 7.545 g), Na$_2$CO$_3$ (40.3 mmoles, 4.268 g) and Aliquat 336 (0.500 g) were suspended in toluene (100 mL) in a 250 mL two-necked-round-bottom-flask with stir bar and condenser. The reaction mixture degassed and Pd(PPh$_3$)$_4$ (0.403 mmoles, 0.465 g) added followed by addition of degassed water (50 mL). Reaction heated to 90° C. for two days. Resulting reaction mixture diluted with ethyl acetate (150 mL), washed with ethyl acetate (3×100 mL). Organic layer washed with brine (2×100 mL), dried over magnesium sulfate, filtered and concentrated. Purification by column chromatography on silica gel using 1:3 DCM:Hexanes to yield white powder (56%, 3.8 g). $^1$H NMR (500 MHz, CD$_2$Cl$_2$) δ=7.45 (d, J=8.5 Hz, 4H), 7.33-7.31 (m, 5H), 7.26-7.19 (m, 5H), 6.65 (s, 2H), 2.71-2.63 (m, 9H0, 1.54 (s, 18H), 1.31-1.20 (m, 14H), 1.15 (t, J=7.49, 7H), 0.83 (t, J=6.85 Hz, 6H).

Compound 27 (4.54 mmoles, 3.800 g) added to 200 mL round bottom flask and dissolved in dichloromethane (90 mL). Trifluoroacetic acid (45.4 mmoles, 5.175 g) added dropwise to the solution. After one day dichloromethane removed by rotary evaporation and the resulting grey powder was dissolved in ethyl ether (100 mL), Sodium bicarbonate added (100 mL) to neutralize TFA, The layers were separated and the organic layer was washed with water (2×100 mL), followed by brine (2×100 mL). Drying over magnesium sulfate and concentration yielded an off white powder (100%, 2.891 g). $^1$H NMR (500 MHz, CD$_2$Cl$_2$) δ=728 (m, 2H), 7.23-7.18 (m, 6H), 7.16 (d, J=8.47 Hz, 4H), 6.76 (d, J=8.37 Hz, 4H), 3.77 (s, 4H), 2.71-2.63 (m, 6H), 1.3-1.19 (m, 16H), 1.15 (t, J=7.5 Hz, 8H), 0.83 (t, J=6.86 Hz, 6H).

In a 250 mL round bottom flask, diamine 28 (4.539 mmoles, 2.891 g), bromobiphenyl (9.123 amides, 2.127 g) and toluene (65 mL) were added. Followed by Pd$_2$(dba)$_3$ (0.227 mmole, 0.208 g) and P$^t$Bu3 (0.454 mmole, 0.092 g). The reaction mixture stirred for 5 minutes before adding the base, NaO$^t$Bu (9.078 mmoles, 0.845 g). Three days later the resulting reaction mixture was diluted with toluene (100 mL), filtered through a pad of silica and celite washed with toluene (3×100 mL), followed by ethyl acetate (2×100 mL) and concentrated to a brown solid. Purification by column chromatography on silica gel, using eluent 1:6 Ethyl acetate:Hexanes, to yield a white powder (55%, 2.367 g). $^1$H NMR (500 MHz, CD$_2$Cl$_2$) δ=7.61 (d, J=7.24 Hz, 4H), 7.57 (d, J=8.51 Hz, 4H), 7.43 (t, J=7.6 Hz, 4H), 7.34-7.28 (m, 12H), 5.99 (s, 2H), 2.73 (q, J=Hz, 4H), 2.66 (t, J=7.7 Hz, 6H), 1.33-1.17 (m, 20H), 0.84 (t, J=7.2 Hz, 6H).

Compound 29 (2.515 mmoles, 2.367 g) and 1-bromo-4-iodo benzene (3.772 mmoles, 1.067 g), Pd$_2$(dba)$_3$ (0.126 mmoles, 0.115 g) and 1,1-Bis(diphenylphosphino)ferrocene (0.251 mmoles, 0.139 g) were suspended in toluene (100 mL) in a 100 mL two-necked-round-bottom-flask fitted with condenser and stir bar. The mixture was stirred, sodium t-butoxide (2.766 mmoles, 0.266 g) was added. The reaction mixture heated at 90° C. until completion. The resulting reaction mixture was diluted with toluene (50 L), filtered through a pad of silica and celite, washed with toluene (2×200 mL) and concentrated to form brown solid. Purification by column chromatography on silica gel using 1:2 dichloromethane:Hexanes, product fractions washed with MeOH, filtered to give white powder (23%, 0.715 g). $^1$H NMR (500 MHz, CD$_2$Cl$_2$) δ=7.61 (d, J=6.95 Hz, 4H), 7.56 (d, J=8.73 Hz, 4H), 7.46-7.4 (m, 8H), 7.34-7.29 (m, 10H), 7.24-7.18 (m, 12H), 7.08 (d, J=8.89 Hz, 4H), 2.74 (q, J=7.5 Hz, 4H), 2.65 (t J=8.12 Hz, 6H), 1.32-1.18 (m, 22H), 0.83 (t, J=6.88 Hz, 6H).

Compound 30 (0.626 g, 0.50 mmol) was added to a scintillation vial and dissolved in 16 mL toluene. A clean, dry 50 mL. Schlenk tube was charged with bis(1,5-cyclooctadiene)nickel(0) (0.278 g, 1.010 mmol). 2,2'-Dipyridyl (0.158 g, 1.010 mmol) and 1,5-cyclooctadiene (0.109 g, 1.010 mmol) were weighed into a scintillation vial and dissolved in 4 mL N,N'-dimethylformamide. The solution was added to the Schlenk tube. The Schlenk tube was inserted into an aluminum block and the block was heated and stirred on a hotplate/stirrer at a setpoint that resulted in an internal temperature of 60° C. The catalyst system was held at 60° C. for 30 minutes and then raised to 70° C. The monomer solution in toluene was added to the Schlenk tube and the tube was sealed. The polymerization mixture was stirred at 70° C. for 18 h. After 18 h, the Schlenk tube was removed from the block and allowed to cool to room temperature. The tube was removed from the glovebox and the contents were poured into a solution of conc. HCl/MeOH (1.5% v/v conc. HCl). After stirring for 2 h, the polymer was collected by vacuum filtration and dried under high vacuum. The polymer was purified by successive precipitations from toluene into HCl/MeOH (1% v/v conc. HCl), MeOH, toluene (CMOS grade), and ethyl acetate. A white, fibrous polymer (0.27 g, 47% yield) was obtained. The molecular weight of the polymer was determined by GPC (THF mobile phase, polystyrene standards): M$_w$=140,399; M$_n$=47,682. NMR analysis confirmed the structure of Compound R.

Synthesis Example 19

Additional dibromo compounds can be prepared in an analogous manner. Additional polymers can be prepared from the dibromo compounds in a manner analogous to that described in Synthesis Example 18. The molecular weight of some additional polymers is given below in Table 1. The molecular weight was determined by GPO (THF mobile phase, polystyrene standards).

TABLE 1

Polymer Molecular Weights

| Compound | Mn | Mw |
| --- | --- | --- |
| S | 152,561 | 270,588 |
| T | 145,262 | 386,212 |
| U | 252,211 | 535,643 |
| V | 524,354 | 1,099,173 |
| W | 22,778 | 109,105 |
| X | 81,920 | 861,804 |
| AA | 91,314 | 197,397 |
| BB | 111,502 | 356,234 |
| CC | 139,464 | 385,906 |
| DD | 59,391 | 1,058,617 |
| EE | 196,812 | 515,643 |

Device Examples 1-10

These examples illustrate the performance of the new compounds in a device.

(a) Materials:

HIJ-1 is an aqueous dispersion of an electrically conductive polymer and a polymeric fluorinated sulfonic acid. Such materials have been described in, for example, published U.S. patent applications US 2004/0102577, US 2004/0127637, and US 2005/0205860, and published POT application WO 2009/018009.

E-1 is a bis(diarylamino)anthracene compound having blue electroluminescence.

Host-1 is a diarylanthracene compound.

ET-1 is a metal quinolate derivative.

(b) Device

In these examples, devices were made by a combination of solution processing and vapor deposition techniques. A substrate with 50 nm indium tin oxide ("ITO") was used as the anode. HIJ-1 was applied by spin coating from an aqueous dispersion. The hole transport material was applied by spin coating from a 0.38 w/v % solution of toluene. The other materials were applied by evaporative deposition. The device structure was:

anode: ITO (50 nm)
hole injection layer: HIJ-1 (50 nm)
hole transport layer: materials and thicknesses shown in Table 2
electroactive layer: E-1 in Host-1 in a 1:13 ratio (32 nm)
electron transport layer: ET-1 (10 nm)
electron injection layer: CsF (1 nm deposited)
cathode: Al (100 nm)

The OLED samples were characterized by measuring their (1) current-voltage (I-V) curves, (2) electroluminescence radiance versus voltage, and (3) electroluminescence spectra versus voltage. All three measurements were performed at the same time and controlled by a computer. The current efficiency of the device at a certain voltage is determined by dividing the electroluminescence radiance of the LED by the current density needed to run the device. The unit is a cd/A. The external quantum efficiency (EQE) is then calculated from the current efficiency (cd/A) and the electroluminance spectra, assuming a Lambertian distribution of emitted light. The results are shown in Table 3.

TABLE 2

| Hole Transport Layer | | |
|---|---|---|
| Example | Hole Transport Material | HTL Thickness, nm |
| 1A | Compound R | 20 |
| 1B | Compound R | 20 |
| 2A | Compound S | 20 |
| 2B | Compound S | 20 |
| 3A | Compound T | 20 |
| 3B | Compound T | 20 |
| 4A | Compound U | 20 |

TABLE 2-continued

| Hole Transport Layer | | |
|---|---|---|
| Example | Hole Transport Material | HTL Thickness, nm |
| 4B | Compound U | 20 |
| 5A | Compound V | 20 |
| 5B | Compound V | 20 |
| 6A | Compound W | 20 |
| 6B | Compound W | 20 |
| 7A | Compound X | 20 |
| 7B | Compound X | 20 |
| 8A | Compound Y | 16 |
| 8B | Compound Y | 16 |
| 9A | Compound DD | 20 |
| 9B | Compound DD | 20 |
| 10A | Compound EE | 20 |
| 10B | Compound EE | 20 |

TABLE 3

Device Results

| Ex. | x, y | Voltage (V) | E.Q.E. (%) | C.E. (cd/A) | P.E. (lm/W) | Lifetest curr. dens. (mA/cm$^2$) | Lifetest Lum. | Raw T50 (h) | Lifetime T50 (h) |
|---|---|---|---|---|---|---|---|---|---|
| 1A | 0.138, 0.141 | 4.38 | 8.0 | 9.1 | 65. | 122 | 8868 | 93 | 3800 |
| 1B | 0.138, 0.141 | 4.34 | 7.9 | 9.0 | 6.5 | 131 | 9397 | 88 | 3968 |
| 2A | 0.139, 0.116 | 3.22 | 7.2 | 7.1 | 7.0 | 126 | 7084 | 173 | 4829 |
| 2B | 0.138, 0.117 | 3.21 | 7.3 | 7.3 | 7.1 | 122 | 7185 | 203 | 5814 |
| 3A | 0.138, 0.120 | 3.20 | 7.8 | 7.8 | 7.7 | 128 | 7862 | 197 | 6543 |
| 3B | 0.138, 0.119 | 3.19 | 7.8 | 7.8 | 7.7 | 122 | 7603 | 220 | 6916 |
| 4A | 0.138, 0.117 | 4.26 | 8.1 | 8.1 | 6.0 | 127 | 7867 | 155 | 5154 |
| 4B | 0.139, 0.118 | 4.32 | 7.7 | 7.7 | 5.6 | 126 | 7445 | 156 | 4749 |
| 5A | 0.138, 0.117 | 4.16 | 8.2 | 8.2 | 6.2 | 129 | 8154 | 175 | 6183 |
| 5B | 0.138, 0.117 | 4.21 | 8.0 | 8.0 | 6.0 | 123 | 7641 | 184 | 5822 |
| 6A | 0.140, 0.115 | 4.48 | 8.0 | 7.9 | 5.5 | 131 | 7524 | 11 | 345 |
| 6B | 0.140, 0.114 | 4.52 | 8.1 | 8.0 | 5.5 | 122 | 7231 | 11 | 320 |
| 7A | 0.137, 0.119 | 3.91 | 7.8 | 7.8 | 6.3 | 125 | 7699 | 128 | 4125 |
| 7B | 0.137, 0.119 | 3.94 | 7.8 | 7.9 | 6.3 | 118 | 7466 | 131 | 4003 |
| 8A | 0.140, 0.105 | 3.16 | 6.2 | 5.7 | 5.7 | 129 | 4526 | 141 | 1835 |
| 8B | 0.141, 0.105 | 3.17 | 6.2 | 5.7 | 5.6 | 124 | 4364 | 153 | 1867 |
| 9A | 0.139, 0.111 | 4.15 | 7.3 | 7.0 | 5.3 | 132 | 7257 | 73 | 2118 |
| 9B | 0.138, 0.110 | 4.11 | 7.4 | 7.0 | 5.4 | 123 | 6906 | 86 | 2292 |
| 10A | 0.139, 0.113 | 4.65 | 7.7 | 7.5 | 5.1 | 133 | 7460 | 16 | 474 |
| 10B | 0.139, 0.113 | 4.61 | 7.7 | 7.5 | 5.1 | 128 | 7198 | 18 | 524 | x, y = the x and y color coordinates according to the C.I.E. chromaticity scale (Commission Internationale de L'Eclairage, 1931);
EQE = external quantum efficiency;
CE = current efficiency;
PE = power efficiency;
V, E.Q.E., C.E. and P.E. are at 1000 nits
T50 is the time in hours to reach 50% of initial luminance;
Lifetime T50 is calculated using an acceleration factor of 1.7.

Example 11

Triplet energies for some compounds were calculated. The energy calculations were performed with the density functional theory (DFT) methods within the Gaussian 03 suite of programs. (*Gaussian* 03, revision D.01; Gaussian, Inc., Wallingford, Conn., 2004). The molecular structures were first optimized at the BP8616-31G+IrMWB60 level and then used in subsequent analytic vibrational frequency calculations at this same level of computation to ensure that these structures were indeed equilibrium ones. For the excited-state calculations, previous experience has shown that time-dependent DFT (TDDFT) at the B3LYP/6-31G+IrMWB60 level is satisfactory in computing the first seven singlet and triplet energy transitions. In order to obtain HOMO and LUMO values for these molecules, the B31LYP/6-31+G(d)+IrMWB60 level was used.

As a model for the polymeric materials, the central monomeric unit

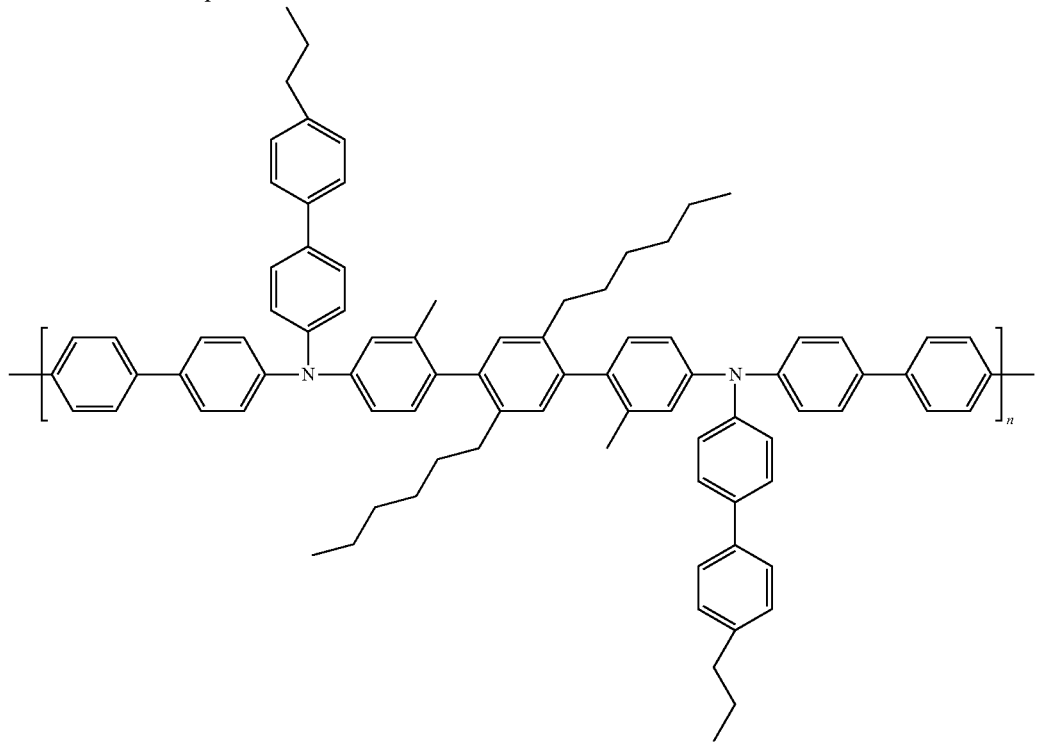

was extended to the next diphenylamino group on each side. So, for example, for Compound S
the calculation was performed on the unit shown below within the brackets.

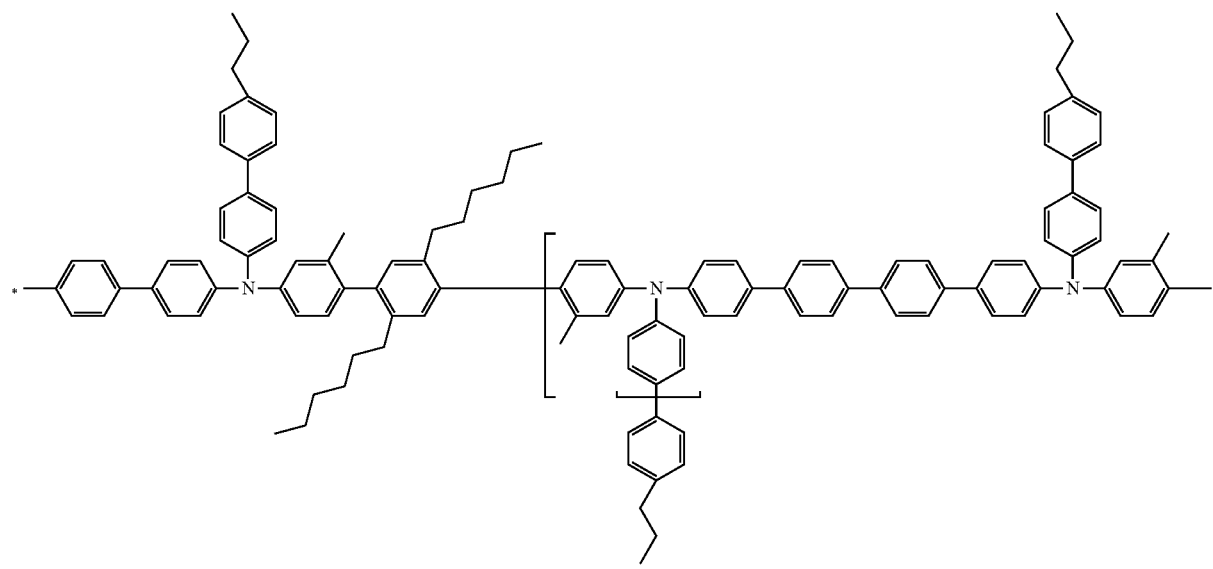

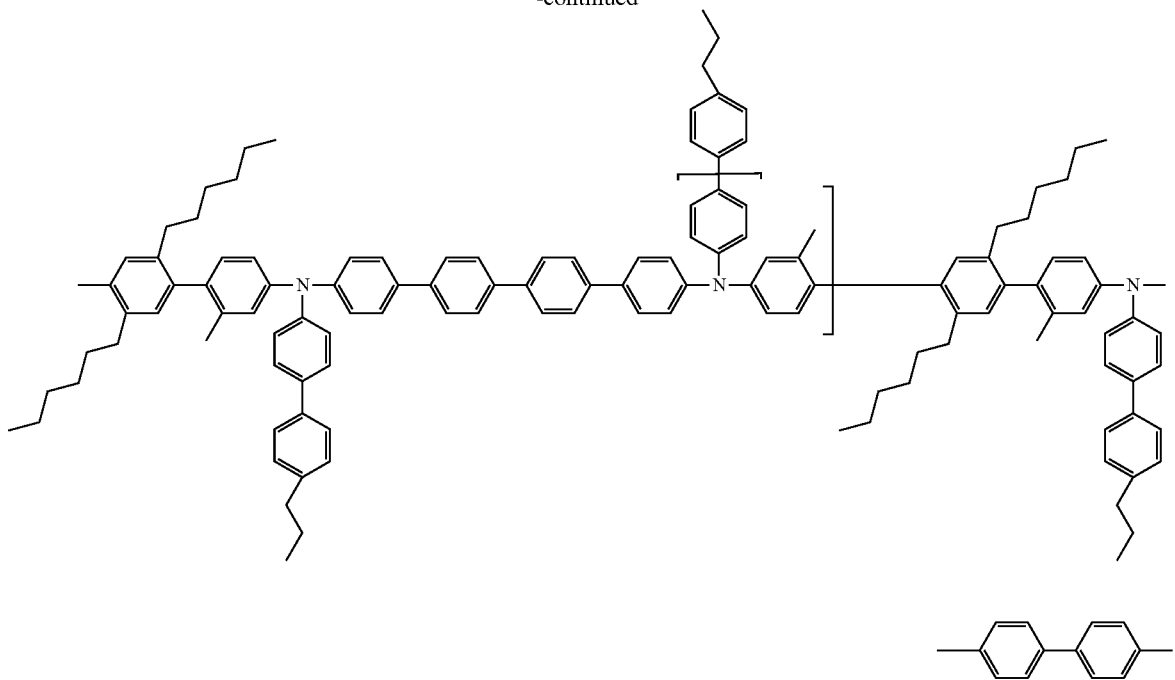
For comparison, the triplet energy for comparative compound Comp-1 was also calculated. Materials such as Comp-1 have been described in published PCT application WO2009/067419.
Comp-1
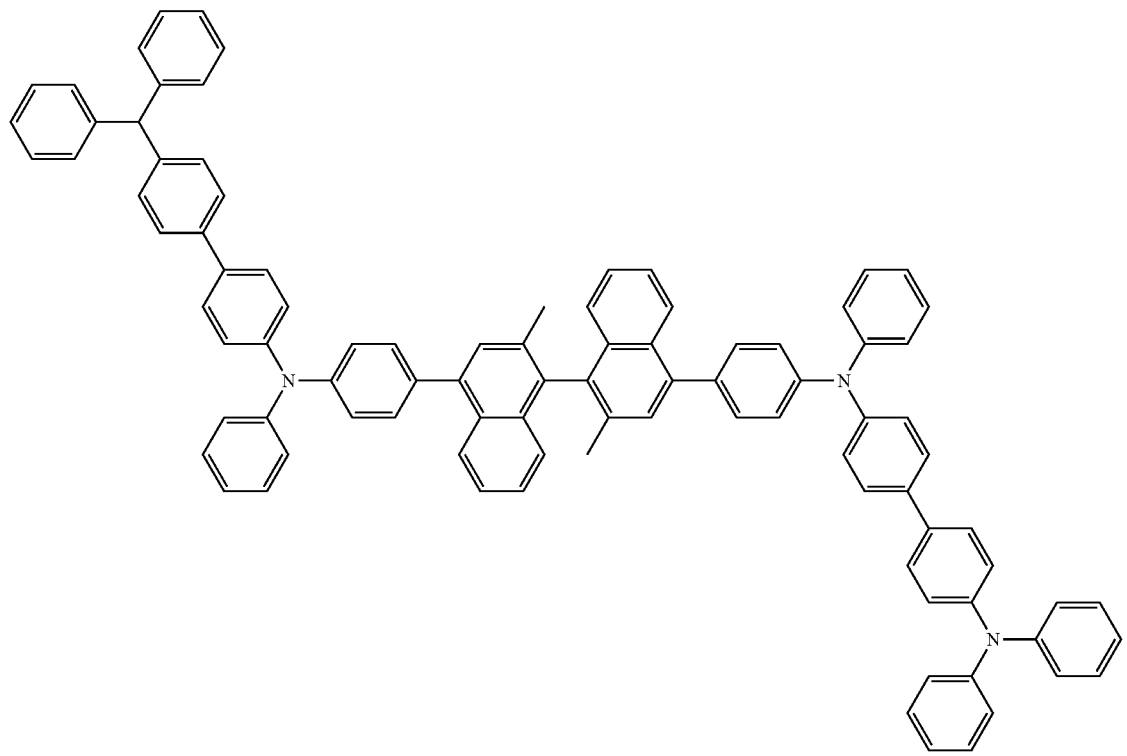

The calculated triplet energies are given in Table 4.

TABLE 4

Triplet energies

| Compound | Triplet Energy, eV |
|---|---|
| Comp-1 | 2.41 |
| Compound S | 2.50 |
| Compound T | 2.50 |
| Compound U | 2.50 |
| Compound W | 2.57 |
| Compound X | 2.56 |
| Compound Z | 2.50 |
| Compound AA | 2.99 |
| Compound BB | 2.50 |
| Compound CC | 2.90 |
| Compound DD | 2.50 |
| Compound EE | 2.60 |

Device Examples 12-13 and Comparative A

These examples illustrate the performance of the new compounds in a device where the light-emitting material is a phosphorescent organometallic complex.
(a) Materials:
E-2 is a tris-cyclometalated iridium complex having blue-green emission.
H-2 is an indolocarbazole compound.
Comparative Compound Comp-2 is a hole transport polymer having the structure below.

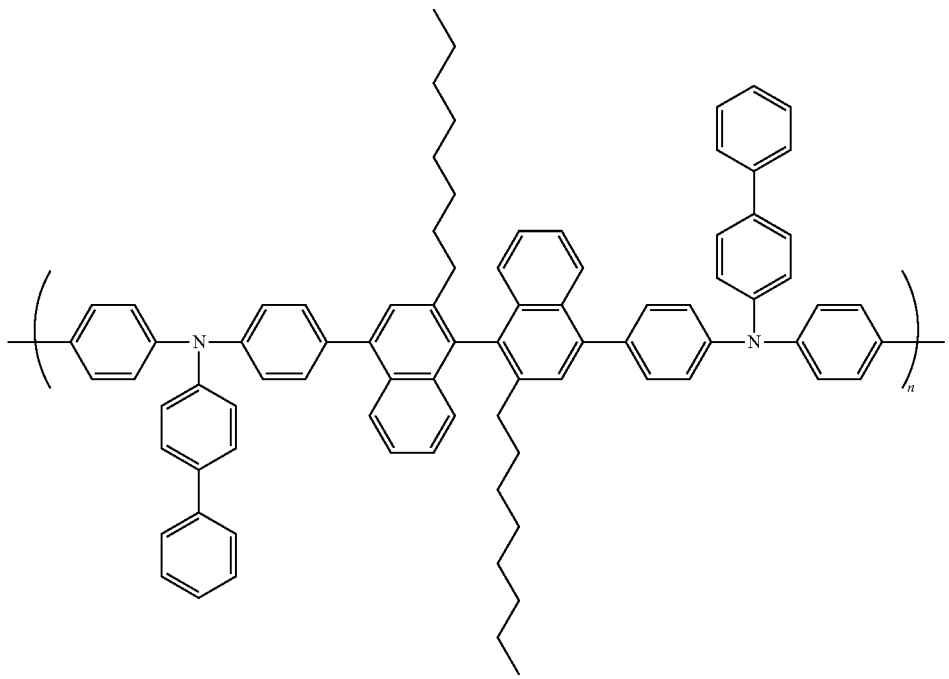

HIJ-1 and ET-1 are described above.
(b) Device
The devices were made as described in Device Examples 1-10. The device structure was:
   anode: ITO (50 nm)
   hole injection layer: HIJ-1 (50 nm)
   hole transport layer (all 20 nm):
   Ex. 12: Compound T
   Ex. 13: Compound AA
   Comparative A: Comp-2
   electroactive layer: E-2 in Host-2 in a 16:84 ratio (60 nm)
   electron transport layer: ET-1 (10 nm)
   electron injection layer: CsF (1 nm deposited)
   cathode: Al (100 nm)
The devices were characterized as described above. The results are given in Table 5.

TABLE 5

| | | | | | | Lifetest | | Raw | Lifetime |
| | | | | | | curr. | | T50 | T50 |
| | | Voltage | E.Q.E. | C.E. | P.E. | dens. | Lifetest | T50 | T50 |
| Ex. | x, y | (V) | (%) | (cd/A) | (lm/W) | (mA/cm$^2$) | Lum. | (h) | (h) |
|---|---|---|---|---|---|---|---|---|---|
| Comp. Ex. A | 0.227, 0.585 | 3.49 | 13.4 | 40.6 | 36.5 | 122 | 12260 | 176 | 15984 |
| Comp. Ex. A | 0.226, 0.584 | 3.49 | 12.9 | 39.0 | 35.1 | 34 | 11510 | 187 | 15216 |
| 12A | 0.225, 0.585 | 3.30 | 16.4 | 49.6 | 47.3 | 36 | 14610 | 140 | 17416 |
| 12B | 0.221, 0.581 | 3.28 | 16.4 | 49.2 | 47.1 | 35 | 14160 | 144 | 17013 |
| 13A | 0.214, 0.573 | 3.37 | 19.8 | 58.1 | 54.2 | 37 | 17890 | 58 | 10450 |
| 13B | 0.214, 0.575 | 3.37 | 20.9 | 61.3 | 57.2 | 33 | 16820 | 65 | 10429 | x, y = the x and y color coordinates according to the C.I.E. chromaticity scale (Commission Internationale de L'Eclairage, 1931);
EQE = external quantum efficiency;
CE = current efficiency;
PE = power efficiency;
V, E.Q.E., C.E. and P.E. are at 1000 nits
T50 is the time in hours to reach 50% of initial luminance;
Lifetime T50 is calculated using an acceleration factor of 1.8.

The triplet energy of Comp-2 can estimated to be about the same as that calculated for Comp-1. Thus, the triplet energies increase as follows:

Comp-2<Compound T<Compound AA

It can be seen that the device efficiency with the phosphorescent emitter increases as the triplet energy increases.

Comp. Ex. A<Ex. 12<Ex. 13

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any subcombination. The use of numerical values in the various ranges specified herein is stated as approximations as though the minimum and maximum values within the stated ranges were both being preceded by the word "about." In this manner, slight variations above and below the stated ranges can be used to achieve substantially the same results as values within the ranges. Also, the disclosure of these ranges is intended as a continuous range including every value between the minimum and maximum average values including fractional values that can result when some of components of one value are mixed with those of different value. Moreover, when broader and narrower ranges are disclosed, it is within the contemplation of this invention to match a minimum value from one range with a maximum value from another range and vice versa.

What is claimed is:
1. A polymer selected from the group consisting of Compound S through Compound X, and Compound Z through Compound EE

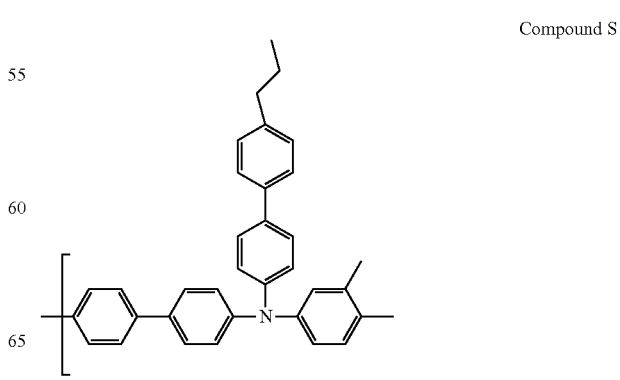

Compound S

105
-continued
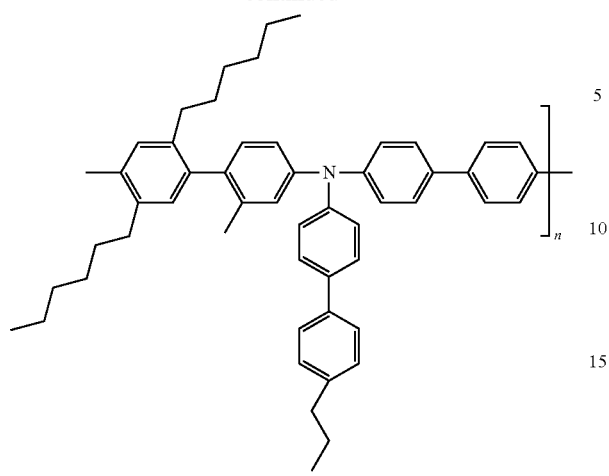
106
-continued
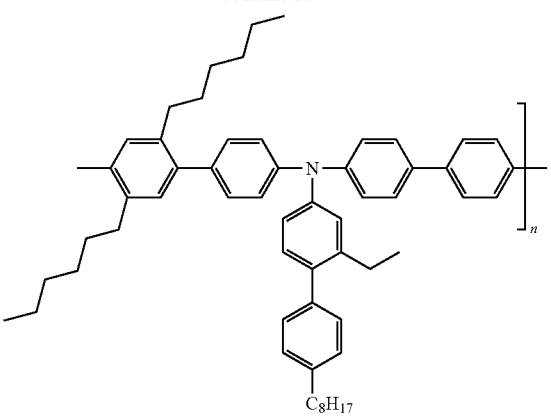
Compound V
Compound T
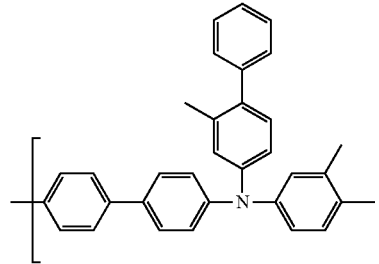
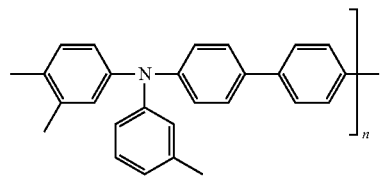
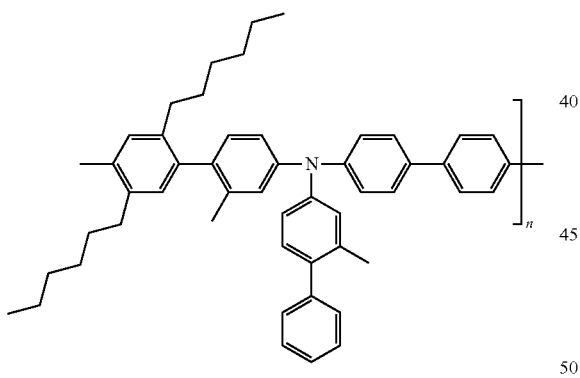
Compound W
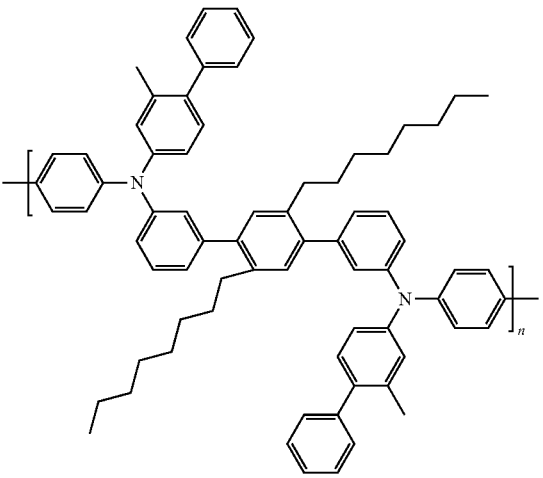
Compound U
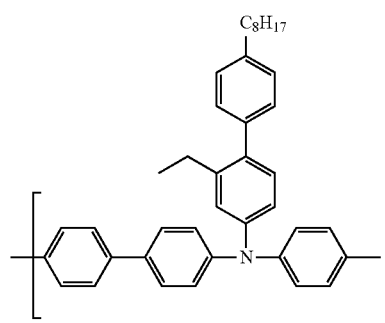

-continued
Compound X
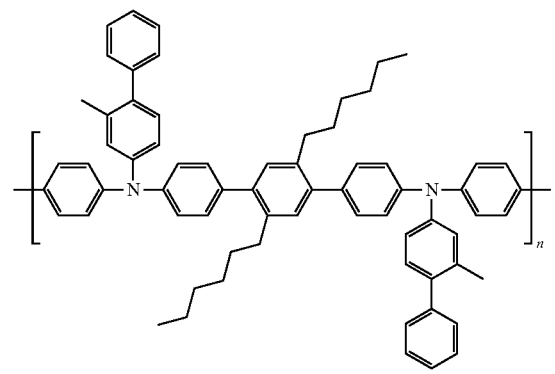
Compound Z
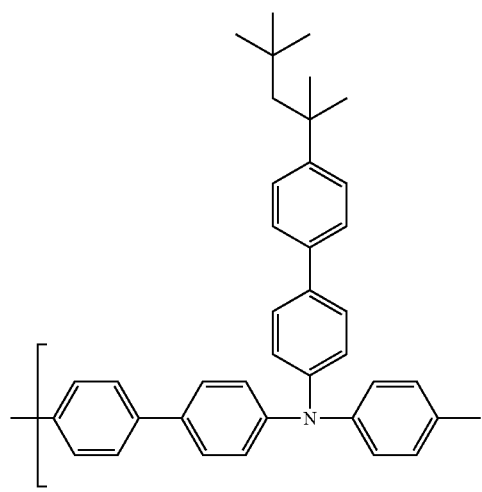
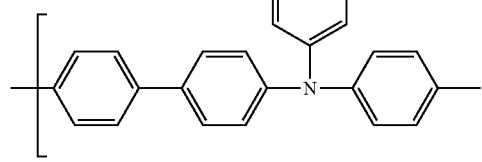
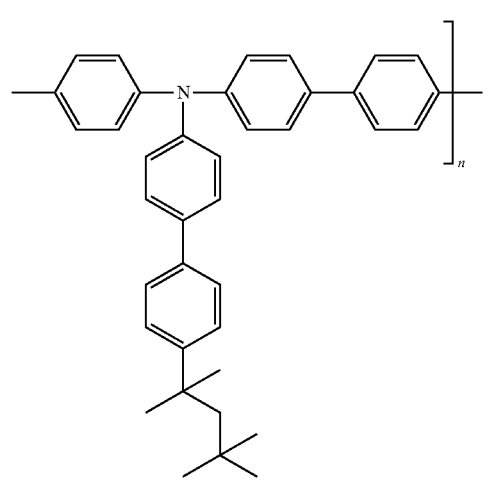
-continued
Compound AA
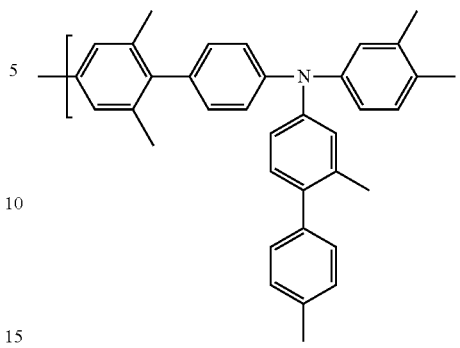
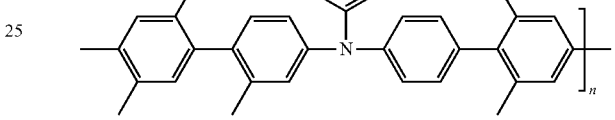
Compound BB
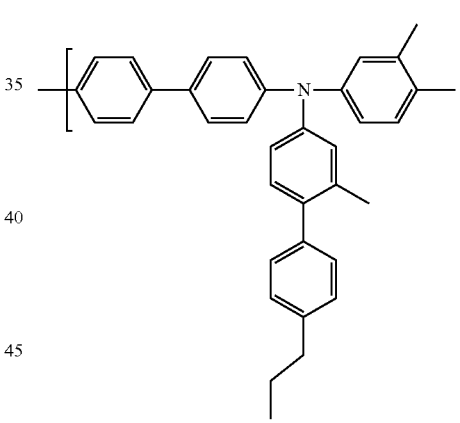
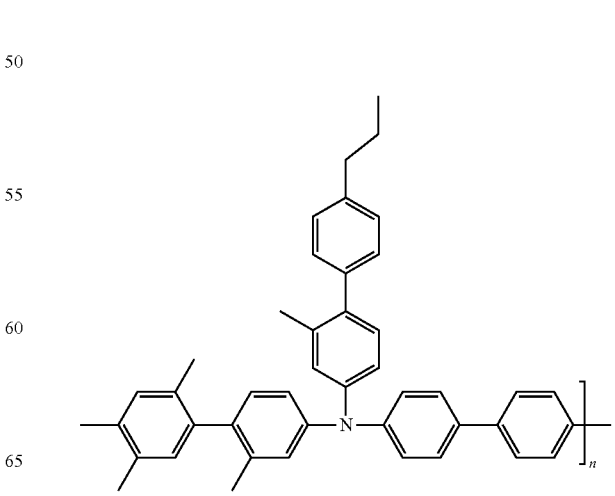

-continued

Compound CC

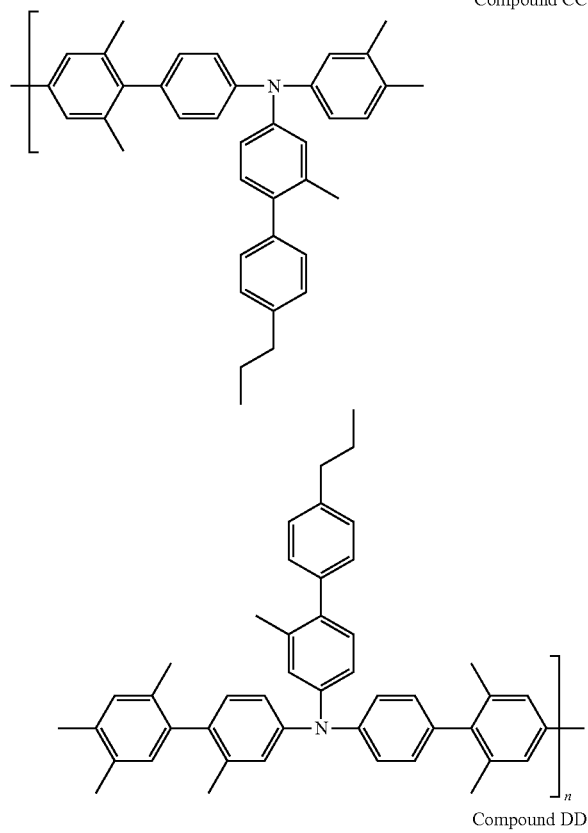

Compound DD

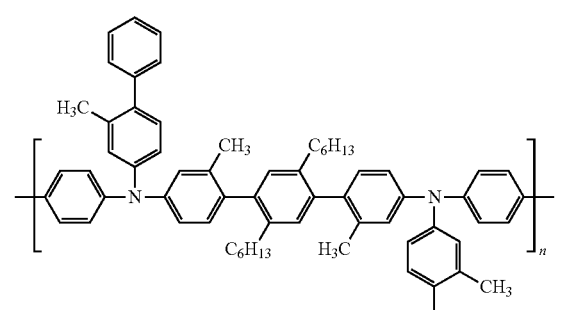

Compound EE

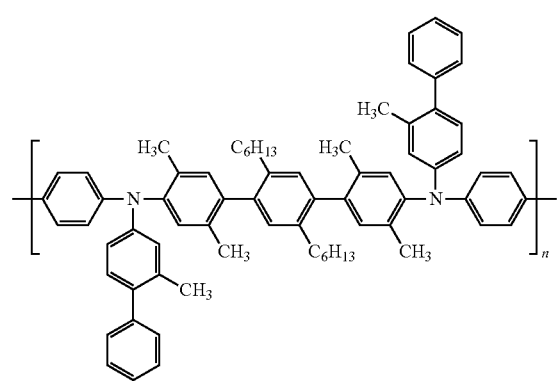

2. A compound having the Formula:

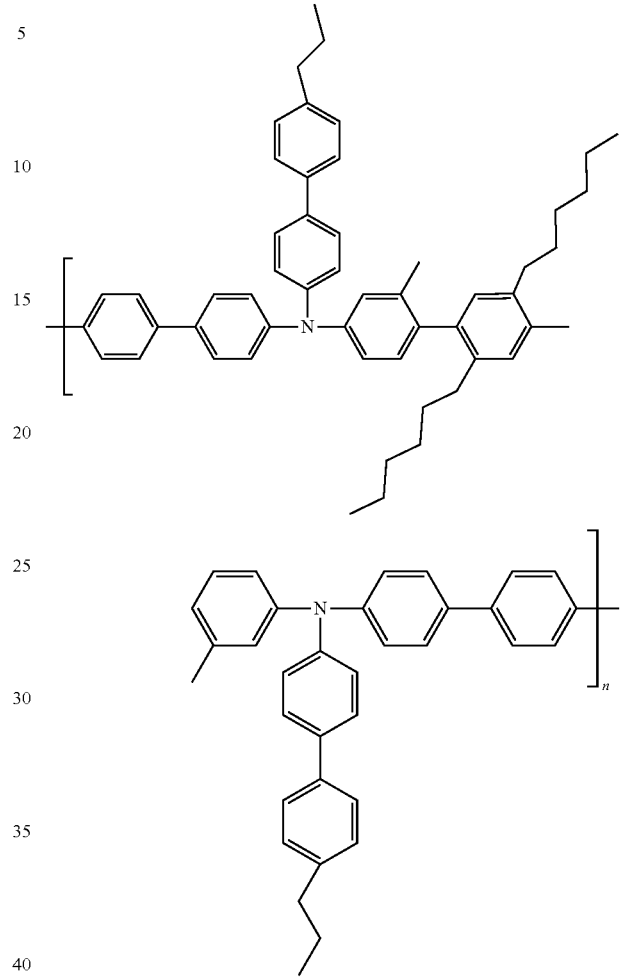

n is an integer greater than 0.

3. An organic electronic device comprising a first electrical contact layer, a second electrical contact layer and an active layer therebetween, wherein the active layer comprises the compound of claim 2.

4. The device of claim 3, wherein the active layer is a hole transport layer.

5. The device of claim 3, wherein the active layer is an electroactive layer comprising a host compound comprising the compound of claim 2 and a dopant.

6. An organic electronic device comprising a first electrical contact layer, a second electrical contact layer and an active layer therebetween, wherein the active layer comprises a compound according to claim 1.

7. The device of claim 6, wherein the active layer is a hole transport layer.

8. The device of claim 6, wherein the active layer is an electroactive layer comprising a host compound comprising the compound of claim 2 and a dopant.

* * * * *